United States Patent
Chiu et al.

(10) Patent No.: US 10,502,733 B2
(45) Date of Patent: Dec. 10, 2019

(54) HYBRID SEMICONDUCTING POLYMER NANOPARTICLES AS POLARIZATION-SENSITIVE FLUORESCENT PROBES

(71) Applicant: University of Washington through its Center for Commercialization, Seattle, WA (US)

(72) Inventors: Daniel T. Chiu, Seattle, WA (US); Maxwell Zeigler, Seattle, WA (US)

(73) Assignee: University of Washington Through Its Center For Commercialization, Seattle, WA (US)

( * ) Notice: Subject to any disclaimer, the term of this patent is extended or adjusted under 35 U.S.C. 154(b) by 32 days.

(21) Appl. No.: 14/903,801

(22) PCT Filed: Jul. 8, 2014

(86) PCT No.: PCT/US2014/045825
§ 371 (c)(1),
(2) Date: Jan. 8, 2016

(87) PCT Pub. No.: WO2015/006374
PCT Pub. Date: Jan. 15, 2015

(65) Prior Publication Data
US 2016/0161475 A1    Jun. 9, 2016

Related U.S. Application Data

(60) Provisional application No. 61/843,796, filed on Jul. 8, 2013.

(51) Int. Cl.
*C09K 11/06* (2006.01)
*G01N 33/543* (2006.01)

(52) U.S. Cl.
CPC ........ *G01N 33/54346* (2013.01); *C09K 11/06* (2013.01); *C09K 2211/1416* (2013.01); *C09K 2211/1425* (2013.01)

(58) Field of Classification Search
CPC combination set(s) only.
See application file for complete search history.

(56) References Cited

U.S. PATENT DOCUMENTS 6,080,516 A * 6/2000 Devlin ................ C07D 487/04
                                                   106/494
7,846,412 B2   12/2010 Nie et al.
(Continued)

FOREIGN PATENT DOCUMENTS

CN      1252085 A     5/2000
CN    102791827 A    11/2012
(Continued)

OTHER PUBLICATIONS

Jin et al., Generation of Functionalized and Robust Semiconducting Polymer Dots with Polyelectrolytes. Chem Comm (Camb). Mar. 28, 2012; 48(26):1-9.*
(Continued)

*Primary Examiner* — Christopher M Babic
*Assistant Examiner* — Arthur S Leonard
(74) *Attorney, Agent, or Firm* — Christensen O'Connor Johnson Kindness PLLC

(57) ABSTRACT

Compositions of, methods of making, and methods of using hybrid nanoparticles comprise at least one semiconducting polymer and at least one nonsemiconducting polymer. Compositions of, methods of making and methods of using hybrid nanoparticles comprise at least one semiconducting polymer and non-semiconducting polymers wherein the non-semiconducting polymer comprises more than one non-semiconducting polymer such that at least one non-semi-
(Continued)

conducting polymer is functionalized for bioconjugation. The hybrid nanoparticles are polarization-sensitive and have low mass ratios with large fluorescence.

24 Claims, 10 Drawing Sheets

(56) References Cited

U.S. PATENT DOCUMENTS

| | | | |
|---|---|---|---|
| 8,147,714 | B2 | 4/2012 | Iftime et al. |
| 8,390,913 | B2 | 3/2013 | Naitou et al. |
| 9,382,473 | B2* | 7/2016 | Chiu .................. B82Y 30/00 |
| 2009/0221099 | A1 | 9/2009 | Rotello et al. |
| 2010/0016512 | A1 | 1/2010 | Wang et al. |
| 2011/0207614 | A1 | 8/2011 | Glyczynski et al. |
| 2011/0266492 | A1 | 11/2011 | Stayton et al. |
| 2011/0269901 | A1 | 11/2011 | Chun et al. |
| 2012/0282632 | A1 | 11/2012 | Chiu et al. |
| 2013/0064776 | A1 | 3/2013 | El Harrak et al. |
| 2014/0004049 | A1* | 1/2014 | Rao .................. A61K 49/0093 424/9.6 |

FOREIGN PATENT DOCUMENTS

| | | |
|---|---|---|
| WO | WO-2010060454 A1 | 6/2010 |
| WO | WO-2011042564 A1 | 4/2011 |
| WO | WO 2011/057295    * | 5/2011 |
| WO | WO 2011/057295 A2 | 5/2011 |
| WO | WO 2012/054525 A2 | 4/2012 |
| WO | WO 2013/101902 A2 | 7/2013 |
| WO | WO-2014017983 A1 | 1/2014 |
| WO | WO-2014058903 A2 | 4/2014 |

OTHER PUBLICATIONS

Ishida et al., A combinatorial approach to producing sterically stabilized (Stealth) immunoliposomal drugs. FEBS Letters 460 (1999) 129-133 (Year: 1999).*
Baier, et al. Fluorescent conjugated polymer nanoparticles by polymerization in miniemulsion. J Am Chem Soc. Oct. 14, 2009;131(40):14267-73. doi: 10.1021/ja905077c.
Ding, et al. Conjugated polymer amplified far-red/near-infrared fluorescence from nanoparticles with aggregation-induced emission characteristics for targeted in vivo imaging. Adv Healthc Mater. Mar. 2013;2(3):500-7. doi: 10.1002/adhm.201200243. Epub Nov. 26, 2012.
Zeigler, et al. Hybrid semiconducting polymer nanoparticles as polarization-sensitive fluorescent probes. J Am Chem Soc. Aug. 7, 2013;135(31):11453-6. doi: 10.1021/ja404719f. Epub Jul. 29, 2013.
Chan, et al. Hybrid semiconducting polymer dot-quantum dot with narrow-band emission, near-infrared fluorescence, and high brightness. J Am Chem Soc. May 2, 2012;134(17):7309-12. doi: 10.1021/ja3022973. Epub Apr. 23, 2012.
Chretien, et al. New data on the microtubule surface lattice. Biol Cell. 1991;71(1-2):161-74.
Hashim, et al. Luminescent quantum-dot-sized conjugated polymer nanoparticles—nanoparticle formation in miniemulsion system. Journal of Materials Chemistry. 2011; 21: 1797-1803.
Huser, et al. Single chain spectroscopy of conformational dependence of conjugated polymer photophysics. Proc Natl Acad Sci USA. Oct. 10, 2000;97(21):11187-91.
International search report and written opinion dated Oct. 16, 2014 for PCT/US2014/045825.
Jakubiak, et al. Aggregation quenching of luminescence in electroluminescent conjugated polymers. J. Phys. Chem. A, 1999; 103(14):2394-2398.
Jin, et al. Near-infrared fluorescent dye-doped semiconducting polymer dots. ACS Nano. Feb. 22, 2011;5(2):1468-75. doi: 10.1021/nn103304m. Epub Jan. 31, 2011.

Klarner, et al.Exciton migration and trapping in copolymers based on dialkylfluorenes. Adv. Mater. 1999; 11:115-119.
Lee, et al. Photoluminescence study on exciton migration and trapping in a copolymer based on poly(fluorene). J. Mater. Chem. 2000; 10:1547-1550.
Medina, et al. Nanoparticles: pharmacological and toxicological significance. Br J Pharmacol. Mar. 2007;150(5):552-8. Epub Jan. 22, 2007.
Nguyen, et al. Conjugated polymer aggregates in solution: control of interchain interactions. J. Chem. Phys. 1999; 110:4068-4078.
Petkau, et al. Pre- and postfunctionalized self-assembled π-conjugated fluorescent organic nanoparticles for dual targeting. J Am Chem Soc. Oct. 26, 2011;133(42):17063-71. doi: 10.1021/ja2075345. Epub Sep. 30, 2011.
Ray, et al. Kinesin follows the microtubule's protofilament axis. J Cell Biol. Jun. 1993;121(5):1083-93.
Rong, et al. Multicolor fluorescent semiconducting polymer dots with narrow emissions and high brightness. ACS Nano. Jan. 22, 2013;7(1):376-84. doi: 10.1021/nn304376z. Epub Jan. 2, 2013.
Schwartz, et al. Interchain and intrachain exciton transport in conjugated polymers: ultrafast studies of energy migration in aligned MEH-PPV/mesoporous silica composites. Synthetic Metals. 2001; 116:35-40.
Wang, et al. Resolving rotational motions of nano-objects in engineered environments and live cells with gold nanorods and differential interference contrast microscopy. J Am Chem Soc. Nov. 24, 2010;132(46):16417-22. doi: 10.1021/ja106506k. Epub Nov. 2, 2010.
Wu, et al. Bioconjugation of ultrabright semiconducting polymer dots for specific cellular targeting. J Am Chem Soc. Nov. 3, 2010;132(43):15410-7. doi: 10.1021/ja107196s.
Wu, et al. Design of highly emissive polymer dot bioconjugates for in vivo tumor targeting. Angew Chem Int Ed Engl. Apr. 4, 2011;50(15):3430-4. doi: 10.1002/anie.201007461. Epub Mar. 4, 2011.
Wu, et al. Highly fluorescent semiconducting polymer dots for biology and medicine. Angew Chem Int Ed Engl. Mar. 11, 2013;52(11):3086-109. doi: 10.1002/anie.201205133. Epub Jan. 10, 2013.
Wu, et al. Multicolor conjugated polymer dots for biological fluorescence imaging. ACS Nano. Nov. 25, 2008;2(11):2415-23. doi: 10.1021/nn800590n.
Wu, et al. Ultrabright and bioorthogonal labeling of cellular targets using semiconducting polymer dots and click cAngew Chem Int Ed Engl. Dec. 3, 2010;49(49):9436-40. doi: 10.1002/anie.201004260. hemistry.
Yu, et al. Nanoscale 3D tracking with conjugated polymer nanoparticles. J Am Chem Soc. Dec. 30, 2009;131(51):18410-4. doi: 10.1021/ja907228q.
Yu, et al. Unmasking electronic energy transfer of conjugated polymers by suppression of O(2) quenching. Science. Aug. 25, 2000;289(5483):1327-30.
Zeigler, et al. Probing rotational viscosity in synaptic vesicles. Biophys J. Jun. 8, 2011;100(11):2846-51. doi: 10.1016/j.bpj.2011. 04.042.
Zhang, et al. Importance of having low-density functional groups for generating high-performance semiconducting polymer dots. ACS Nano. Jun. 26, 2012;6(6):5429-39. doi: 10.1021/nn301308w. Epub May 24, 2012.
Zhou, et al. Fluorescent chemosensors based on energy migration in conjugated polymers: the molecular wire approach to increased sensitivity. J. Am. Chem. Soc. 1995; 117(50):12593-12602.
Extend European search report and supplemental search report dated Feb. 3, 2017 for EP Application No. 14823695.3.
Feng, et al., Conjugated polymer nanoparticles: preparation, properties, functionalization and biological applications, chemical society reviews, Jun. 7, 2013, 42(6): 6620-33.
Geng, et al., Conjugated Polymer and Gold Nanoparticle Co-loaded PLGA Nanocomposites with Eccentric Internal Nanostructure for Dual-modal Targeted Cellular Imaging, Small, Aug. 6, 2012, 8(15):2421-29.
Li, et al., Generic Strategy of Preparing Fluorescent Conjugated-Polymer-Loaded Poly(DL-lactide-co-Glycolide) Nanoparticles for

(56) References Cited

OTHER PUBLICATIONS

Targeted Cell Imaging, Advanced Functional Materials, Nov. 23, 2009,19(22):3535-42. XP001549683.

Maxwell, et al., Hybrid Semiconducting Polymer Nanoparticles as Polarization-Sensitive Fluorescent Probes, J. Amer. Chem. society, Aug. 7, 2013, 135(31):11453-56.

Yu, et al., Stable Functionalization of Small Semiconducting Polymer Dots via Covalent Cross-Linking and Their Application for Specific Cellular Imaging, Advanced Materials, Jul. 10, 2012.

Zhang, et al., Highly luminescent, fluorinated semiconducting polymer dots for cellular imaging and analysis, Chemical Communications-Chemco., Aug. 8, 2013, 49(78):8256-58. XP055152162.

Jin, et al. Generation of functionalized and robust semiconducting polymer dots with polyelectrolytes. Chem Commun (Camb). Mar. 28, 2012;48(26):3161-3. doi: 10.1039/c2cc17703j. Epub Feb. 20, 2012.

Office action dated Jul. 25, 2017 for CN Application No. 201480049490.2.

Jin, et al., Generation of functionalized and robust semiconducting polymer dots with polyelectrolytes, Chem. Commun (Camb), Mar. 28, 2012, 48(26):1-8. Doi: 10.1039/c2cc17703j.

"CN 201480049490.2 Second Office Action dated Apr. 23, 2018 (w/ English translation)", p. 1-20.

China National Intellectual Property Administration: Notice on the Third Office Action dated Mar. 28, 2019, issued in corresponding Chinese Application No. 201480049490.2, filed Jul. 8, 2014, 15 pages.

* cited by examiner

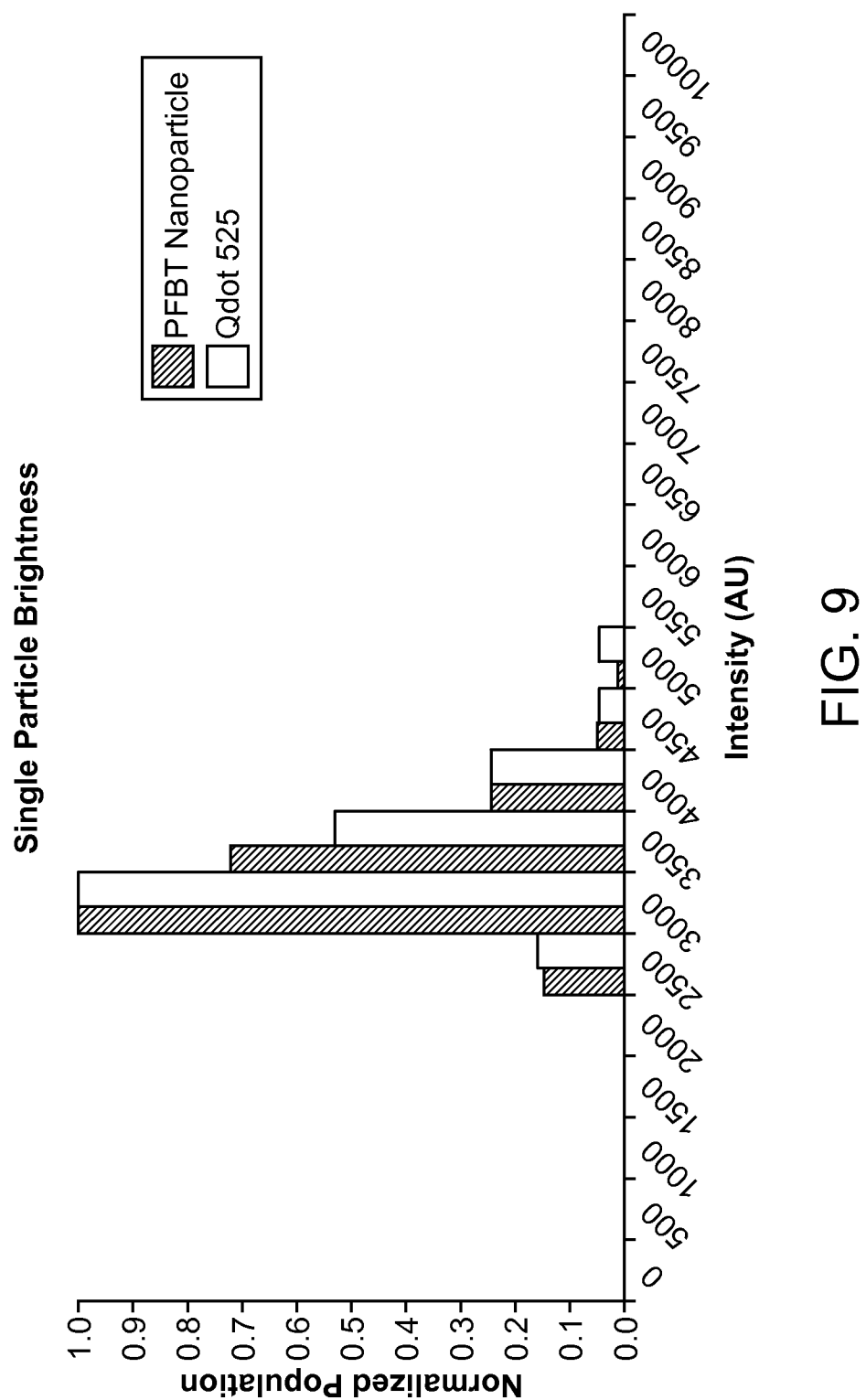

HYBRID SEMICONDUCTING POLYMER NANOPARTICLES AS POLARIZATION-SENSITIVE FLUORESCENT PROBES

CROSS-REFERENCE

This application is a U.S. National Phase Application under 35 U.S.C. § 371 of International Application No. PCT/US2014/045825, filed Jul. 8, 2014, which claims the benefit of U.S. Provisional Application No. 61/843,796, filed Jul. 8, 2013, which application is incorporated herein by reference in its entirety for all purposes.

BACKGROUND

Advances in understanding biological systems have relied on applications of fluorescence microscopy, flow cytometry, versatile biological assays, and biosensors. There has been considerable interest in developing brighter and more photostable fluorescent probes for use as detection agents for these and other platforms. Semiconducting polymers continue to be explored for such uses.

SUMMARY

In various aspects, the present disclosure provides polarization-sensitive nanoparticles comprising: a chromophoric polymer; a first matrix polymer; and a second matrix polymer, wherein the polarization-sensitive nanoparticle has at least one critical dimension of 1 nm to 1000 nm.

In various aspects, the present disclosure provides particles comprising a polarization-sensitive nanoparticle of the present disclosure, wherein the particle is a quantum dot, a gold nanoparticle or an iron nanoparticle.

In various aspects, the present disclosure provides compositions comprising a plurality of the polarization-sensitive nanoparticles of the present disclosure in a solution, wherein the composition is a monodispersion.

In various aspects, the present disclosure provides methods of analyzing a target, the method comprising binding any one of the polarization-sensitive nanoparticles of the present disclosure to the target; illuminating the nanoparticle with electromagnetic radiation sufficient to produce a florescence signal; and detecting the fluorescence signal.

In various aspects, the present disclosure provides methods of analyzing a target, the method comprising binding any one of the polarization-sensitive nanoparticles of the present disclosure to the target; illuminating the nanoparticle with polarized electromagnetic radiation sufficient to produce a florescence signal; and detecting the fluorescence signal.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 9 shows the single particle brightness histogram comparing polarization-sensitive nanoparticles and Qhybrid nanoparticle 525 according to an aspect of the present disclosure.

DETAILED DESCRIPTION

Figure 1:
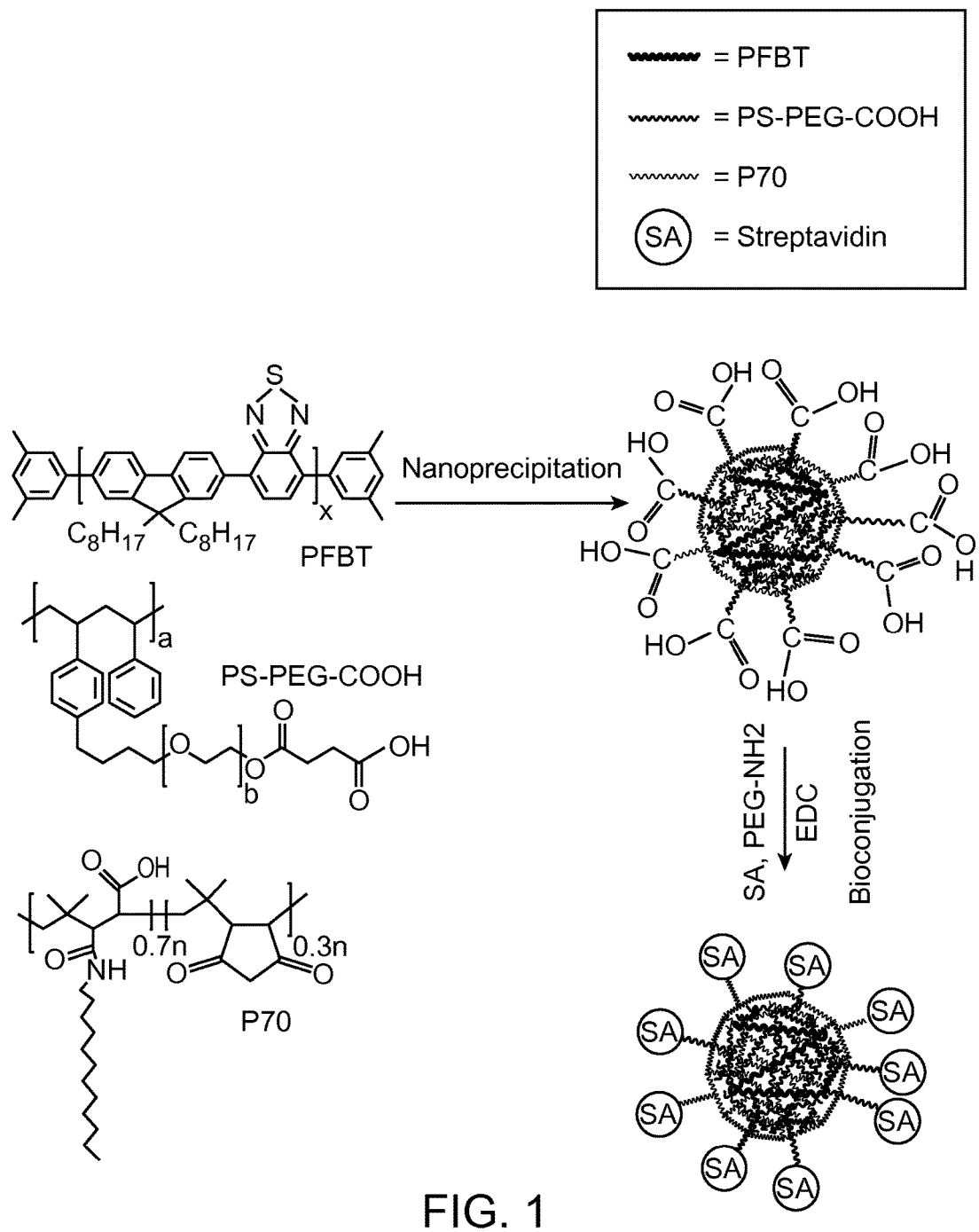
FIG. 1 is a schematic showing the preparation of polymer hybrid nanoparticle using nanoprecipitation and subsequent bioconjugation.

Semiconducting polymer nanoparticles offer many advantages as fluorescent tags (Wu, C., Chem. Int. Edit. 2013, 52, 3086-3109). They are bright (Wu, C., J. Am. Chem. Soc. 2010, 132, 15410-15417), emitting enough photons to be tracked with nanometer accuracy (Yu, J., J. Am. Chem. Soc. 2009, 131, 18410-18414). In some aspects, semiconducting polymer nanoparticles are made using the nanoprecipitation method from a wide range of fluorescent polymers (Hashim, Z., J. Mater. Chem. 2011, 21, 1797-1803; Zhang, X., ACS Nano. 2012, 6, 5429-5439), so that the absorption and emission spectra are tailored to the specific application (Rong, Y., ACS Nano. 2013, 7, 376-384). The small size and close packing of polymers allow for efficient energy transfer to doped dyes (Jin, Y., ACS Nano. 2011, 5, 1468-1475). In some aspects, the hybrid nanoparticles possess flexible surface chemistry. In certain aspects, the hybrid nanoparticles are functionalized with antibodies and other proteins (Jin, Y., ACS Nano. 2011, 5, 1468-1475; Wu, C., Chem. Int. Ed. 2010, 49, 9346-9440; Wu, C., Chem. Int. Ed. 2011, 50, 3430-3434; Petkau, K., J. Am. Chem. Soc. 2011, 133, 17063-17071) to bind a wide array of targets with a high degree of specificity. In some aspects, they are also incorporated with other hybrid nanoparticles, such as quantum dots or gold or iron hybrid nanoparticles (Chan, Y., J. Am. Chem. Soc. 2012, 134, 7309-7312). A variety of the polymers used in semiconducting hybrid nanoparticle formation have been shown to be biocompatible and available for use according to the present disclosure (Medina, C., J. Pharmacol. 2007, 150, 552-558).

Electronically excited conjugated polymers in hybrid nanoparticles undergo excitation energy transfer (EET) along5re the polymer chain (Zhou, Q., J. Am. Chem. Soc. 1995, 117, 12593-12602) and transfer-absorbed energy to segments where light emission takes place (Klärner, G., Adv. Mater. 1999, 11, 115-119). This occurs by transferring energy from local regions on a semiconducting polymer chain of higher energy to lower energy regions where emission is preferred (Nguyen, T., J. Chem. Phys. 1999, 110, 4068-4078; Jakubiak, R., J. Phys. Chem. A. 1999, 103, 2394-2398; Yu, J., Science. 2000, 289, 1327-1330).

Certain embodiments of the present disclosure relate to a novel class of hybrid semiconducting, polarization-sensitive nanoparticles that comprise both a semiconducting polymer and a non-semiconducting polymer, which is also referred to herein as a "matrix polymer." In some aspects, the polarization-sensitive nanoparticles are modified with a functional group and/or biomolecular conjugates for a variety of applications, including but not limited to flow cytometry, fluorescence activated sorting, immunofluorescence, immunohistochemistry, fluorescence multiplexing, single molecule imaging, single particle tracking, protein folding, protein rotational dynamics, DNA and gene analysis, protein analysis, metabolite analysis, lipid analysis, FRET based sensors, high throughput screening, cellular imaging, in vivo imaging, bioorthogonal labeling, click reactions, fluorescence-based biological assays such as immunoassays and enzyme-based assays, and a variety of fluorescence techniques in biological assays and measurements.

While not wishing to be limited to any particular theory or concept, the present disclosure is based in part on the concept that hybrid nanoparticle formation from a polymer, for example, a semiconducting polymer, and.or a non-semiconducting polymer, is driven in large part by intramolecular and/or intermolecular polymer interactions. For example, polarization-sensitive nanoparticles are formed due to intramolecular and/or intermolecular hydrophobic interactions that cause a single polymer molecule or several polymer molecules to form a polarization-sensitive nanoparticle. In some aspects, hydrophilic groups on a polymer, such as those on side chains, interfere with hybrid nanoparticle stability and photophysical performance and cellular targeting. For example, the density and/or positioning of functional groups along the polymer can impact the formation and stability and performance of the hybrid semiconducting polymer nanoparticle. As described further herein, the present disclosure provides embodiments of hybrid, polarization-sensitive nanoparticles comprising semiconducting polymers that are optionally functionalized so as to provide favorable nanoparticle packing and internal structure, high fluorescence brightness, and low nonspecific binding of the polarization-sensitive nanoparticles in biological applications. Furthermore, the present disclosure provides compositions and methods for allowing bioconjugation of hybrid semiconducting polymer nanoparticles while also maintaining stability and performance. These embodiments, for example, relate to the location and/or density of functional groups in the hybrid semiconducting polymer nanoparticle, which are dependent on the hydrophilicity/hydrophobicity of the functional groups.

The present disclosure further describes blending fluorescent conjugated semiconducting polymers at low mass ratios with matrix polymers to create hybrid semiconducting polymer nanoparticles. In various aspects, the hybrid semiconducting polymer nanoparticles have immobilized chain segments with high fluorescence polarization anisotropy. In some aspects, the fluorescent conjugated semiconducting polymers of the present disclosure have a polarized fluorescence intensity. In some aspects, the polarized fluorescent intensity emitted from the nanoparticles of the present disclosure changes as a function of the rotation of the nanoparticles. In various aspects, the change in fluorescence intensity is measured. In other embodiments, changes in the polarized fluorescent intensity are inferred. In various aspects, the hybrid semiconducting polymer nanoparticles of the present disclosure are attached to a protein or other target of interest. In various aspects, the hybrid semiconducting polymer nanoparticles emit polarized light. In some aspects, observing a change in intensity of polarized light enables the determination of the location of a protein or other target of interest to which the hybrid semiconducting polymer nanoparticle is attached. For example, as the hybrid semiconducting polymer nanoparticles moves, a change in protein orientation as well as spatial information are obtained.

Where a range of values is provided, it is understood that each intervening value, to the tenth of the unit of the lower limit unless the context clearly dictates otherwise, between the upper and lower limit of that range, and any other stated or intervening value in that stated range, is encompassed within the disclosure provided herein. The upper and lower limits of these smaller ranges are independently included in the smaller ranges, and are also encompassed within the disclosure, subject to any specifically excluded limit in the stated range. Where the stated range includes one or both of the limits, ranges excluding either or both of those included limits are also included in the disclosure provided herein.

Unless defined otherwise, all technical and scientific terms used herein have the same meaning as commonly understood to one of ordinary skill in the art to which this disclosure belongs. Although any methods, devices and materials similar or equivalent to those described herein are used in the practice or testing of the disclosure, the preferred methods, devices and materials are now described.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Embodiments of the disclosure are modified, if necessary, to employ the systems, functions, and concepts of the above references and application to provide yet further embodiments of the disclosure. These and other changes are made to the disclosure in light of the detailed description.

Specific elements of any foregoing embodiments are combined or substituted for elements in other embodiments. Furthermore, while advantages associated with certain embodiments of the disclosure have been described in the context of these embodiments, other embodiments can also exhibit such advantages, and not all embodiments need necessarily exhibit such advantages to fall within the scope of the disclosure. Additional advantages and features of the disclosure will be set forth in part in the description which follows, and in part will be obvious from the description, or are learned by practice of the disclosure.

As used herein, the term "chromophoric hybrid nanoparticle" or "chromophoric polymer hybrid nanoparticle" refers to a structure comprising one or more polymers (e.g., chromophoric polymers) that have been collapsed into a stable sub-micron sized particle. The terms "hybrid nanoparticle," "polymer hybrid nanoparticle," "polarization-sensitive nanoparticle," "chromophoric hybrid nanoparticle," and "chromophoric polymer hybrid nanoparticle" are used interchangeably herein to refer to the nanoparticles of the present disclosure. The chromophoric polarization-sensitive nanoparticles provided herein are formed by any method known in the art for collapsing polymers, including without limitation, methods relying on precipitation (e.g., nanoprecipitation), methods relying on the formation of emulsions (e.g., mini or micro emulsion), and methods relying on condensation. In certain aspects, a chromophoric hybrid nanoparticle is formed by nanoprecipitation. As used herein, the term "chromophoric polymer" is a polymer in which at least a portion of the polymer comprises chromophoric units. The term "chromophore" is given its ordinary meaning in the art. A chromophore absorbs certain wavelength of light from UV to near infrared region. In some aspects, the chromophore is emissive.

Chromophoric polarization-sensitive nanoparticles are pi-conjugated species with luminescent properties. The chromophoric polarization-sensitive nanoparticles comprise polymers with one or more repeating units, which in some aspects, are combined in fixed, ordered, or random configurations and ratios. A repeating unit is a monomer or a chemical motif that occurs throughout the polymer, such as an aromatic or heterocyclic unit. In some aspects, the polymers are halogenated, for example, fluorinated, chlorinated, brominated, or iodinated. In certain aspects, a polymer, repeating unit, or monomer are halogenated at one or multiple sites. In some aspects, a halogenated polymer, for example, a fluorinated polymer, provides greater levels of fluorescence than a non-halogenated analogous polymer. In various aspects, chromophoric polymer hybrid nanoparticle comprise one or more conjugated polymers (e.g., semiconducting polymers) that have been collapsed into a stable sub-micron sized particle. In various aspects, the chromophoric polarization-sensitive nanoparticles comprise fluorescent hybrid nanoparticles having at least one condensed conjugated polymer.

As used herein, the term "polymer" is a molecule composed of at least two repeating structural units typically connected by covalent chemical bonds. In some aspects, the repeating structural unit is one type of monomer, and the resulting polymer is a homopolymer. In some aspects, the polymers comprise two different types of monomers, or three different types of monomers, or more types of monomers. Examples of monomers for synthesizing conjugated polymers include, but are not limited to, benzene, fluorene, benzothiadiazole; thiophen, BODIPY; porphyrin, peryene, squaraine, and their derivatives. One of ordinary skill in the art will appreciate that the different types of monomers can be distributed along a polymer chain in a variety of ways. For example, in some aspects, three different types of monomers are randomly distributed along the polymer. It will similarly be appreciated that the distribution of monomers along the polymer are represented in different ways. The number of repeating structural units (e.g., monomers) along the length of a polymer is, in some aspects, represented by "n." In some aspects, n can range, e.g., from at least 2, from at least 100, from at least 500, from at least 1000, from at least 5000, or from at least 10,000, or from at least 100,000, or higher. In certain embodiments, n can range from 2 to 10000, from 20 to 10000, from 20 to 500, from 50 to 300, from 100 to 1000, or from 500 to 5000.

Polymers generally have extended molecular structures comprising backbones that optionally contain pendant side groups. In various aspects, the polymers provided herein include, but are not limited to, linear polymers and branched polymers such as star polymers, comb polymers, brush polymers, ladders, and dendrimers. The polymers in certain aspects described herein include semiconducting polymers, some of which are generally known in the art. In certain embodiments, the polymers (e.g., semiconducting polymers) of the present disclosure include polymers that do not have triple bonds present along the polymer backbone, i.e., some polymers of the present disclosure are polymers having a backbone consisting of single bonds, double bonds, or a combination thereof. In some aspects, monomers along the polymer backbone will be connected by only single or double bonds (e.g., carbon bonds). In some aspects, the structural characteristics (e.g., rigidity) of the polymers affect whether the polymer folds into a compact hybrid nanoparticle. For example, in certain aspects, polymers that include repeating units of triple bonds are more rigid than those that include single and/or double bonds along the backbone. In certain aspects, this leads to complex packing and phase behavior in the hybrid nanoparticles, resulting in broadened emission spectra. (Wu, C., J. ACS Nano 2008, 2, 2415-2423.)

The present disclosure also provides for variants of polymers. In some aspects, a variant of a polymer is a conjugated polymer. In various aspects, conjugated chromophoric polarization-sensitive nanoparticles are referred to as chromophoric polarization-sensitive nanoparticles. In some aspects, halides (e.g., fluorine) are attached to or incorporated into the chromophoric polymer hybrid nanoparticle structure. The particle size of the chromophoric polarization-sensitive nanoparticles is comparable to that of a Qhybrid nanoparticle, for example, greater than 80% the size of a Qhybrid nanoparticle. In various aspects, the semiconducting polymers in chromophoric polarization-sensitive nanoparticles are present at a total mass percentage that is at least 50% of the total nanoparticle composition. In other aspects, the mass percentage of the semiconducting polymer is at least 80% of the total nanoparticle composition. In various aspects, the chromophoric polarization-sensitive nanoparticles comprise a hydrophobic polymer interior. In some aspects, a chromophoric polymer hybrid nanoparticle has a halide (e.g., fluorine) content of less than 50% by mass. In some aspects, the mass percentage of the semiconducting polymer in the polarization-sensitive nanoparticles is greater than 40%, 50%, 60%, 70%, 80%, 90% or 99%. In some aspects, the mass percentage of the semiconducting polymer in the polarization-sensitive nanoparticles is about 40%, about 50%, about 60%, about 70%, about 80%, about 90% about or about 99%. In some aspects, the mass percentage of the semiconducting polymer in the polarization-sensitive nanoparticles is in the range of 40%-50%, 45%-55%, 50%-60%, 55%-65%, 60%-70%, 65%-75%, 70%-80%, 75%-85%, 80%-90%, 85%-95% or 90%-100%. In some aspects, the mass percentage of the semiconducting polymer in the polarization-sensitive nanoparticles is the range of about 40%-50%, about 45%-55%, about 50%-60%, about 55%-65%, about 60%-70%, about 65%-75%, about 70%-80%, about 75%-85%, about 80%-90%, about 85%-95% or about 90%-100%.

As used herein, a "chromophoric copolymer" is represented by writing the identity of the major chromophoric species. For example, PFBT is a chromophoric polymer containing fluorene and benzothiazole units at a certain ratio. In some aspects, a dash is used to indicate the percentage of the minor chromophoric species and then the identity of the minor chromophoric species. For example, PF-0.1 BT is a chromophoric copolymer containing 90% PF and 10% BT.

A "chromophoric unit" in this disclosure includes, but is not limited to, a unit of structures with delocalized pi-electrons, a unit of small organic dye molecules, and/or a unit of metal complexes. Examples of chromophoric polymers include polymers comprising units of structures with delocalized pi-electrons such as semiconducting polymers, polymers comprising units of small organic dye molecules, polymers comprising units of metal complexes, and polymers comprising units of any combinations thereof.

As used herein the term "functional group" refers to any chemical unit that is capable of attachment to a reference compound, such as by any stable physical or chemical association, to the chromophoric polymer, thereby rendering the surface of the chromophoric polymer hybrid nanoparticle available for conjugation. A functional group is also referred to herein as a "reactive functional group" or a "functionalization moiety."

In various aspects, the polymers of the present disclosure are capable of being functionalized with a functional group, including without limitation, the chromophoric polymers, the first matrix polymers and/or the second matrix polymers. One or all of the polymers contained within the polarization-sensitive nanoparticles are independently capable of being functionalized with a functional group.

As used herein, the term "hydrophilic moiety" refers to a chemical unit that increases the hydrophilicity of a polymer. In some aspects, hydrophilic moieties include hydrophilic functional groups. In certain embodiments, hydrophilic moieties include non-reactive hydrophilic moieties that are distinct from hydrophilic functional groups. For example, in some aspects, non-reactive hydrophilic moieties include nonionic, non-reactive hydrophilic moieties, such as water soluble polymers (e.g., polyethylene glycol (PEG)). In further aspects, non-reactive hydrophilic moieties also include ionic, non-reactive hydrophilic moieties, such as positive ionic species, negative ionic species, and zwitterionic species, or combinations thereof.

As used herein, the term "hydrophilic functional group" refers either to a functional group that is hydrophilic in nature or to a hydrophobic functional group that is attached to a hydrophilic side chain or hydrophilic moiety, which renders the hydrophobic functional group more hydrophilic in nature and which facilitate the arrangement of the hydrophobic functional groups on the chromophoric polymer hybrid nanoparticle particle surface rather than getting buried inside the hydrophobic core of the chromophoric polymer hybrid nanoparticle. Examples of hydrophobic functional groups that are rendered more hydrophilic by attachment to hydrophilic side chains or moieties include but not limited to alkyne, strained alkyne, azide, diene, alkene, cyclooctyne, and phosphine groups (for click chemistry) attached to a hydrophilic side chain such as PEG (polyethylene glycol) or to any other hydrophilic side chains. As described herein, a hydrophobic functional group that is attached to a hydrophilic side chain or hydrophilic moiety is attached to the polymer before particle formation, i.e., pre-functionalized. In some aspects, a hydrophobic functional group that is attached to a hydrophilic side chain or hydrophilic moiety is suitable for bioconjugation.

In certain embodiments, a functional group includes a hydrophilic functional group that is hydrophilic in nature and is attached to the polymer (e.g., on the side chain). In some aspects, hydrophilic functional groups include, carboxylic acid or salts thereof, amino, mercapto, azido, aldehyde, ester, hydroxyl, carbonyl, sulfate, sulfonate, phosphate, cyanate, succinimidyl ester, substituted derivatives thereof. In certain embodiments, hydrophilic functional groups include carboxylic acid or salts thereof, amino, mercapto, azido, aldehyde, ester, hydroxyl, carbonyl, sulfate, phosphate, cyanate, succinimidyl ester, and substituted derivatives thereof. In certain embodiments, the hydrophilic functional groups are suitable for bioconjugation. In some aspects, the hydrophilic functional groups are suitable for bioconjugation and also stable in aqueous solution (e.g., the groups do not hydrolyze). Such functional groups can be found by one of ordinary skill in the art, for example in Bioconjugate Techniques (Academic Press, New York, 1996 or later versions) the content of which is herein incorporated by reference in its entirety for all purposes. Some hydrophilic functional groups suitable for bioconjugation include carboxylic acid or salts thereof, amino, mercapto, azido, aldehyde, ester, hydroxyl, carbonyl, phosphate, cyanate, succinimidyl ester, and substituted derivatives thereof. In some aspects, hydrophilic functional groups suitable for conjugation include carboxylic acid or salts thereof, amino groups, mercapto, succinimidyl ester, and hydroxyl. A non-limiting list of hydrophilic functional group pairs is provided below in Table 1.

TABLE 1

Exemplary hydrophilic functional group pairs for conjugation chemistry.

| Functional Groups | Reacts With |
| --- | --- |
| Ketone and aldehyde groups | Amino, hydrazido and aminooxy |
| Imide | Amino, hydrazido and aminooxy |
| Cyano | Hydroxy |
| Alkylating agents (such as haloalkyl groups and maleimido derivatives) | Thiol, amino, hydrazido, aminooxy |
| Carboxyl groups (including activated carboxyl groups) | Amino, hydroxyl, hydrazido, aminooxy |

In some aspects, a functional group includes a hydrophobic functional group that is attached to a hydrophobic polymer (e.g., on a hydrophobic side chain). In some aspects, hydrophobic functional groups generally include, but are not limited to, alkynes, alkenes, and substituted alkyl derivatives that are suitable for conjugation. The present disclosure provides polymers that include hydrophobic functional groups for compact hybrid nanoparticle formation (e.g., pre-functionalization). After formation, some of the hydrophobic functional groups are chemically modified to form hydrophilic functional groups used for bioconjugation (e.g., post-functionalization). In certain embodiments, hydrophobic functional groups attached to a hydrophobic polymer are suitable for bioconjugation. For example, in some aspects, the hydrophobic functional groups include without limitation those used for click chemistry, such as alkyne, strained alkyne, azide, diene, alkene, cyclooctyne, and phosphine groups. In some aspects, these hydrophobic functional groups are, e.g., be used for bioconjugation reactions that covalently couple the polarization-sensitive nanoparticles to a biologically relevant molecule (e.g., an antibody).

In various aspects, the functional groups are capable of being attached to the chromophoric polarization-sensitive nanoparticles in a variety of ways. For example, in certain aspects, the polymers are chemically modified to include functional groups prior to particle formation, described herein as "pre-functionalization." Pre-functionalization includes embodiments in which the monomers include the functional groups prior to formation of the polymers, as well as reacting an already formed polymer to include functional groups along the backbone of monomers. Alternatively, in other aspects, a chromophoric polymer hybrid nanoparticle is modified after particle formation to attach a functional group, e.g., on the surface of the polymer hybrid nanoparticle, described herein as "post-functionalization." One of ordinary skill in the art will appreciate that pre- and post-functionalization can be carried out in a variety of orders to form a functionalized polymer. For example, in some aspects, a polymer is pre-functionalized with functional groups, e.g., hydrophobic functional groups. In further aspects, the hydrophobic pre-functionalized polymer is condensed into a hybrid nanoparticle, and then post-functionalized with a functional group, e.g., a hydrophilic functional group suitable for bioconjugation. Alternatively, in other aspects, both pre- and post-functionalization steps include functionalization with hydrophilic groups or hydrophobic groups.

As described herein, some of the functional groups are "suitable for bioconjugation," which is used of refer to a functional group that is covalently bonded to a biomolecule, such as an antibody, protein, nucleic acid, streptavidin, or other molecule of biological relevance. Such functional groups can be found by one of ordinary skill in the art, for example in Bioconjugate Techniques (Academic Press, New York, 1996 or later versions) the content of which is herein incorporated by reference in its entirety for all purposes. In some aspects, functional groups suitable for bioconjugation include functional groups that are capable of being conjugated to a biomolecule under a variety of conditions, such as, e.g., in polar or non-polar solvents. In certain embodiments, functional groups suitable for bioconjugation include functional groups that are conjugated to a biomolecule in an aqueous solution. In some aspects, functional groups suitable for bioconjugation can include functional groups that are conjugated to a biomolecule in an aqueous solution in which the biomolecule retains its biological activity (e.g., monoclonal binding specificity for an antibody). In certain embodiments, functional groups suitable for bioconjugation can include functional groups that are covalently bonded to a biomolecule. For example, typical covalent bonding attachments of functional groups to biomolecules can include, e.g., a carboxyl functional group reacting with an amine on a biomolecule to form an amide bond, a sulfhydryl functional group reacting with a sulfhydryl group on a biomolecule to form a cysteine bond, or an amino functional group reacting with a carboxyl group on a biomolecule to form an amide bond. In some aspects, the specific reactions of bioconjugations can include the functional group pairs in Table 1.

As used herein, the term "rationally functionalized" refers to the modification of a chromophoric polymer or hybrid nanoparticle by the attachment of a pre-defined number of reactive functional groups. For example, the polymers are chemically modified to include functional groups prior to particle formation (pre-functionalization). Alternatively, a chromophoric polymer hybrid nanoparticle are modified after formation to attach a functional group, e.g., on the surface of the polymer hybrid nanoparticle (post-functionalization). In one case, a plurality of rationally functionalized hybrid nanoparticles will each have a single functional group attached to their surface. In other embodiments, a plurality of functionalized hybrid nanoparticles will each have exactly two functional groups attached to their surface. In yet other embodiments, a plurality of functionalized hybrid nanoparticles will each have exactly 3, 4, 5, 6, 7, 8, 9, 10, or more functional groups attached to their surface. The rational functionalization of chromophoric polymers and/or hybrid nanoparticles is achieved in various fashions. For example, in one case a pre-defined number of reactive functional groups are attached to a chromophoric polymer, which is then collapsed into a hybrid nanoparticle. In a second case, a pre-formed chromophoric hybrid nanoparticle, in which the number of reactive functional groups on the surface of the particle has not been pre-defined, are treated by some methods to form a chromophoric particle with a defined number of functional group. Examples of such methods such as solvent washing or surface passivation are provided herein to render the hybrid nanoparticle rationally functionalized.

Nonionic and non-reactive hydrophilic moieties are added to the polymers to achieve certain characteristics, such as to reduce nonspecific adsorption in biological applications. A variety of polymers, such as polyethylene glycol (PEG), are well known in the art to reduce non-specific absorption. Nonionic hydrophilic moieties are linked to a chromophoric polymer prior to particle formation (pre-functionalization). Alternatively, nonionic hydrophilic moieties are linked to a chromophoric polymer hybrid nanoparticle after hybrid nanoparticle formation, e.g., on the surface of the polymer hybrid nanoparticle (post-functionalization). In some aspects, nonionic hydrophilic moieties are attached via both pre- and post-functionalization. For pre-functionalization, the density of hydrophilic moieties, such as PEG groups in the chromophoric polymer, can affect the formation, stability, internal structure, and fluorescence brightness of the polarization-sensitive nanoparticles. As described further herein, the density of PEG groups should be sufficiently low so that they do not adversely affect the stability and performance of the polarization-sensitive nanoparticles. For post-functionalization, the density of PEG groups on the surface of the chromophoric polymer hybrid nanoparticle are high because the hybrid nanoparticles are already formed and the PEG groups do not adversely affect the formation, stability, internal structure, and fluorescence brightness of the polarization-sensitive nanoparticles, but can reduce nonspecific interactions.

Ionic and non-reactive hydrophilic moieties are linked to chromophoric polymers to achieve certain properties for the resulting polarization-sensitive nanoparticles, such as increasing surface zeta potential by highly charged species, and/or yielding zwitterionic surfaces by zwitterionic species. In some aspects, nonionic hydrophilic moieties are attached via pre-functionalization, post-functionalization, or a combination of both. For pre-functionalization, the density of ionic hydrophilic moieties in the chromophoric polymer can affect the formation, stability, internal structure, and fluorescence brightness of the polarization-sensitive nanoparticles. Therefore, the density of ionic moieties should be sufficiently low so that they do not adversely affect the stability and performance of the polarization-sensitive nanoparticles. In some aspects, post-functionalization of the nanoparticle is used, in which case, the density of ionic moieties on the surface of the chromophoric polymer hybrid nanoparticle are capable of being high because the hybrid nanoparticles are already formed and the ionic moieties do not adversely affect the formation, stability, internal structure, and fluorescence brightness of the polarization-sensitive nanoparticles, but can provide certain properties such as high surface zeta potential and/or zwitterionic surfaces.

In some aspects, a reactive functional group is attached to the surface of the hybrid nanoparticle via a linker moiety. A variety of linker moieties are generally well known in the art and can be found by one of ordinary skill in the art, for example in Bioconjugate Techniques (Academic Press, New York, 1996 or later versions) the content of which is herein incorporated by reference in its entirety for all purposes. In certain embodiments, the linker moieties include a water soluble polymer. In some aspects, the chromophoric polarization-sensitive nanoparticles also include polymers having non-reactive chemical groups. In certain embodiments, non-reactive chemical groups also include, e.g., a water soluble polymer. Suitable water soluble polymers for the present disclosure include, but are not limited to, polyethylene glycol.

As used herein, the "density" of functional groups and moieties attached to a polymer, for example at one or more side chains or termini of the polymer, refers to the number of monomers with attached functional groups or moieties expressed as a percentage of the monomeric units of the polymer. For example, if half of the monomeric units of a particular polymer have a functional group attached, the density of the functional groups is 50%. In some aspects, the polymers (e.g., semiconducting polymers) in the chromophoric polarization-sensitive nanoparticles are designed to include ranges of functional group or moiety densities. In certain embodiments, density of the hydrophobic functional groups on a polymer (e.g., a semiconducting polymer) are less than about 100%, less than about 90%, less than about 80%, less than about 70%, less than about 60%, less than about 50%, less than about 40%, less than about 30%, less than about 20%, or less than about 10%. When pre-functionalization is used, the density of hydrophilic functional groups and moieties in the chromophoric polymer can affect the formation, stability, internal structure, and fluorescence brightness of the polarization-sensitive nanoparticles. Therefore, the density of hydrophilic functional groups and moieties on a chromophoric polymer should be sufficiently low so that they do not adversely affect the stability and performance of the polarization-sensitive nanoparticles. In some aspects, density of the hydrophilic functional groups and moieties on a polymer (e.g., a semiconducting polymer) are less than about 50%, less than about 40%, less than about 30%, less than about 20%, less than about 10%, or less than about 5%. In some aspects involving post-functionalization, hydrophilic functional groups and moieties are linked to the surface of a chromophoric hybrid nanoparticle, in which the density of functionalization is high (e.g., greater than about 50%) because the hybrid nanoparticles are already formed and the hydrophilic moieties do not adversely affect the formation, stability, internal structure, and fluorescence brightness of the polarization-sensitive nanoparticles, but can provide certain properties such as reducing nonspecific interactions by PEG groups, and/or generating high surface zeta potential by highly charged species and/or creating zwitterionic surfaces by zwitterionic moieties. In certain embodiments, the polymers include both hydrophobic and hydrophilic functional groups at a percentage listed above. In some aspects, the polymers described herein will include at least 50% hydrophobic functional groups. It will be appreciated by one of ordinary skill in the art that the locations of the side-chain functional groups are randomly distributed along the length of a polymer. For example, if a polymer has a length n of 100 monomers, then the side chains substituted with functional groups (e.g., carboxyl groups) are randomly located along the length of the polymer. Some functional groups are located on immediately adjacent monomers or farther down the polymer, e.g., two or three monomers in one direction. In certain embodiments, the functional groups are functional groups suitable for bioconjugation, as described further herein. Densities are determined using a variety of spectroscopic techniques, such as nuclear magnetic resonance (NMR).

The present disclosure provides for methods and compositions using polymers. A polymer is a molecule composed of at least two repeating structural units typically connected by covalent chemical bonds. The repeating structural units are one type of monomer, and the resulting polymer is a homopolymer. In some aspects, the polymers include two different types of monomers, or three different types of monomers, or more types of monomers.

A polymer of the present disclosure can have a range of subunits, such as monomers or repeat units. In some aspects, the number of subunits in a polymer is, for example, about 2 to about 100,000, about 2 to about 10,000, about 2 to about 1,000, about 2 to about 100, about 10 to about 100,000, about 10 to about 10,000, about 10 to about 1,000, about 100 to about 100,000, or about 100 to about 10,000. In some aspects, the number of subunits in a polymer is, for example, 2 to 100,000, 2 to 10,000, 2 to 1,000, 2 to 100, 10 to 100,000, 10 to 10,000, 10 to 1,000, 100 to 100,000, or 100 to 10,000. In some aspects, the number of subunits in a polymer is, for example, greater than 2, greater than 10, greater than 100, greater than 1,000, greater than 10,000; or greater than 100,000. In some aspects, the number of subunits in a polymer is, for example, less than 2, less than 10, less than 100, less than 1,000, less than 10,000; or less than 100,000. In some aspects, the number of subunits in a polymer is, for example, about 2, about 10, about 100, about 1,000, about 10,000; or about 100,000. In some aspects, the number of subunits in a polymer is, for example, 2, 10, 100, 1,000, 10,000; or 100,000.

A polymer of the disclosure can have different kinds of subunits, for example, 2, 3, 4, 5, 6, 7, 8, 9, or 10 different kinds of subunits. In various aspects, the present disclosure provides polarization-sensitive nanoparticles having a chromophoric nanoparticle, a first matrix polymer, and a second matrix polymer. Within each of those polymers, there can be further individual subunits. An individual subunit can provide as percentage of the overall mass or a percentage of the number of units or monomers of the polymer, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. An individual subunit can provide as percentage of the overall mass or a percentage of the number of units or monomers of the polymer, for example, greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or greater than 100%. An individual subunit can provide as percentage of the overall mass or a percentage of the number of units or monomers of the polymer, for example, less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, less than 95%, or less than 100%. An individual subunit can provide as percentage of the overall mass or a percentage of the number of units or monomers of the polymer, for example, 5%, 10%, 15%, 20%, 25%, 30%, 35%, 40%, 45%, 50%, 55%, 60%, 65%, 70%, 75%, 80%, 85%, 90%, 95%, or 100%.

In some aspects, conjugated polymers are synthesized. Examples of monomers for synthesizing conjugated polymers include, but not limit to, benzene, fluorene, benzothiadiazole; thiophen, BODIPY; porphyrin, peryene, squaraine, and their derivatives. In some aspects, polymers are chromophoric polymers and form hybrid nanoparticles using the methods described herein.

The chromophoric polarization-sensitive nanoparticles of the present disclosure are formed using a variety of polymers including semiconducting polymers and non-semiconducting polymers.

Chromophoric Polymers

In various aspects, the present disclosure provides polarization-sensitive nanoparticles comprising: a chromophoric polymer; a first matrix polymer; and a second matrix polymer, wherein the polarization-sensitive nanoparticle has at least one critical dimension of 1 nm to 1000 nm.

In certain aspects, the chromophoric polymer is a semiconducting polymer. In some aspects, the chromophoric polymer is a short-chain polymer. In further aspects, the chromophoric polymer is hydrophobic.

In certain aspects, the polarization-sensitive nanoparticles comprise a chromophoric polymer selected from poly(9,9-dihexylfluorenyl-2,7-diyl) (PDHF), poly(9,9-dioctylfluorenyl-2,7-diyl) (PFO)), (poly[{9,9-dioctyl-2,7-divinylene-fluorenylene}-alt-co-{2-methoxy-5-(2-ethylhexyloxy)-1,4-phenylene}] (PFPV), poly[(9,9-dioctylfluorenyl-2,7-diyl)-co-(4,7-Di-2-thienyl-2,1,3-benzothiadiazole)] (PFTBT), poly[(9,9-dioctylfluorenyl-2,7-diyl)-9-co-(4,7-di-2-thienyl-2,1,3-benzothiadiazole)] (PF-0.1TBT)), poly[(9,9-dioctyl-fluorenyl-2,7-diyl)-alt-co-(1,4-benzo-(2,1',3)-thiadiazole)] (PFBT), poly[(9,9-di(2-ethylhexyl)fluorenyl-2,7-diyl)-alt-2,5-difluoro-1,4-benzene] (PFDFB), poly[(9,9-di(2-ethylhexyl)fluorenyl-2,7-diyl)-alt-1,4-benzene] (PFB), poly[(9,9-di(2-ethylhexyl)fluorenyl-2,7-diyl)-alt-4,4'-diphenyl-5,6-difluoro-1,4-benzo-(2,1,3)-thiadiazole] (PFDPDFBT), poly[(9,9-di(2-ethylhexyl)fluorenyl-2,7-diyl)-alt-4,4'-diphenyl-1,4-benzo-(2,1,3)-thiadiazole] (PFDPBT), (poly[(9,9-di(2-ethylhexyl)fluorenyl-2,7-diyl)-alt-4,4'-diphenyl-5-fluoro-1,4-benzo-(2,1,3)-thiadiazole] (PFDPFBT), poly[2-methoxy-5-(2-ethylhexyloxy)-1,4-phenylenevinylene] (MEH-PPV)), poly[2-methoxy-5-(2-ethylhexyloxy)-1,4-(1-cyanovinylene-1,4-phenylene)] (CN-PPV), BODIPY, a BODIPY derivative or a combination thereof As used herein, the term "alkyl" refers to a straight or branched, saturated, aliphatic radical having the number of carbon atoms indicated. For example, C1-C6 alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but is divalent, such as when the alkyl group links two moieties together.

As used herein, the term "heteroalkyl" refers to a straight or branched, saturated, aliphatic radical of carbon atoms, where at least one of the carbon atoms is replaced with a heteroatom, such as N, O or S. Additional heteroatoms are also contemplated, including, but not limited to, B, Al, Si and P.

As used herein, the term "lower" in connection with organic radicals or compounds defines a compound or radical that is branched or unbranched and saturated or unsaturated with up to and including seven carbon atoms and as few as one carbon atom. Also contemplated are organic radicals or compounds having a range of carbon atoms from one carbon atom to seven carbon atoms. Also contemplated are organic radicals or compounds having one carbon atom, two carbon atoms, three carbon atoms, four carbon atoms, five carbon atoms, six carbon atoms, and/or seven carbon atoms alone or in any combination with one another. In certain aspects, "lower" in connection with organic radicals or compounds defines a compound or radical that is branched or unbranched and saturated or unsaturated with up to and including four carbon atoms and as few as one carbon atom. Exemplary lower alkyls include, without limitation, methyl, ethyl, propyl, butyl, amyl, hexyl, heptyl, and isomeric forms thereof.

As used herein, the term "alkylene" refers to an alkyl group, as defined above, linking at least two other groups, i.e., a divalent hydrocarbon radical. The two moieties linked to the alkylene are linked to the same atom or different atoms of the alkylene. For instance, a straight chain alkylene are the bivalent radical of $-(CH_2)_n-$, where n is 1, 2, 3, 4, 5 or 6. Alkylene groups include, but are not limited to, methylene, ethylene, propylene, isopropylene, butylene, isobutylene, sec-butylene, pentylene and hexylene.

The groups described herein are substituted or unsubstituted. Substituents for the alkyl and heteroalkyl radicals (including those groups in various aspects referred to as alkylene, alkenyl, heteroalkylene, heteroalkenyl, alkynyl, cycloalkyl, heterocycloalkyl, cycloalkenyl, and heterocycloalkenyl) can be a variety of groups, such as alkyl, aryl, cyano (CN), amino, sulfide, aldehyde, ester, ether, acid, hydroxyl or halide. Substituents can have a reactive group, such as but not limited to chloro, bromo, iodo, hydroxyl, or amino. Suitable substituents are selected from: —OR', =O, =NR', =N—OR', —NR'R", —SR', -halogen, —SiR'R"R'", —OC(O)R', —C(O)R', —CO$_2$R', —CONR'R," —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R," —CN and —NO$_2$ in a number ranging from zero to (2m'+1), where m' is the total number of carbon atoms in such radical. R', R" and R'" each independently refer to hydrogen, unsubstituted (C$_1$-C$_8$) alkyl and heteroalkyl, unsubstituted aryl, alkoxy or thioalkoxy groups, or aryl-(C$_1$-C$_4$)alkyl groups. When R' and R" are attached to the same nitrogen atom, they are combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

As used herein, the term "alkoxy" refers to an alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups are further substituted with a variety of substituents described within. For example, the alkoxy groups are substituted with halogens to form a "haloalkoxy" group.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

As used herein, the term "alkenylene" refers to an alkenyl group, as defined above, linking at least two other groups, i.e., a divalent hydrocarbon radical. The two moieties linked to the alkenylene are linked to the same atom or different atoms of the alkenylene. Alkenylene groups include, but are not limited to, ethenylene, propenylene, isopropenylene, butenylene, isobutenylene, sec-butenylene, pentenylene and hexenylene.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

As used herein, the term "alkynylene" refers to an alkynyl group, as defined above, linking at least two other groups, i.e., a divalent hydrocarbon radical. The two moieties linked to the alkynylene are linked to the same atom or different atoms of the alkynylene. Alkynylene groups include, but are not limited to, ethynylene, propynylene, isopropynylene, butynylene, sec-butynylene, pentynylene and hexynylene.

As used herein, the term "alkyl amine" refers to an alkyl groups as defined within, having one or more amino groups. The amino groups are primary, secondary or tertiary. The alkyl amine is further substituted with a hydroxy group. Alkyl amines can include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group.

As used herein, the term "halogen" or "halide" refers to fluorine, chlorine, bromine and iodine. As used herein, the term "haloalkyl" refers to alkyl as defined above where some or all of the hydrogen atoms are substituted with halogen atoms. In certain aspects, halogen (halo) is chloro or fluoro. In further aspects, halogen (halo) is chloro, fluro, bromo or iodo. As used herein, the term "halo-alkoxy" refers to an alkoxy group having at least one halogen. Halo-alkoxy is as defined for alkoxy where some or all of the hydrogen atoms are substituted with halogen atoms. In certain aspects, the alkoxy groups are substituted with 1, 2, 3, or more halogens. When all the hydrogens are replaced with a halogen, for example by fluorine, the compounds are per-substituted, for example, perfluorinated. Halo-alkoxy includes, but is not limited to, trifluoromethoxy, 2,2,2,-trifluoroethoxy, perfluoroethoxy, and the like.

As used herein, the term "cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, C3-8 cycloalkyl includes cyclopropyl, cyclobutyl, cyclopentyl, cyclohexyl, cyclooctyl, and norbornane.

As used herein, the term "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

As used herein, the term "heterocycloalkyl" refers to a ring system having from 3 ring members to about 20 ring members and from 1 to about 5 heteroatoms such as N, O and S. Additional heteroatoms are contemplated, including, but not limited to, B, Al, Si and P. In certain aspects, the heteroatoms are oxidized, such as, but not limited to, —S(O)— and —S(O)$_2$—.

As used herein, the term "heterocycloalkylene" refers to a heterocycloalkyl group, as defined above, linking at least two other groups. The two moieties linked to the heterocycloalkylene are linked to the same atom or different atoms of the heterocycloalkylene.

As used herein, the term "aryl" refers to a monocyclic or fused bicyclic, tricyclic or greater, aromatic ring assembly containing 6 to 16 ring carbon atoms. For example, aryl can be phenyl, benzyl, azulenyl or naphthyl. "Arylene" means a divalent radical derived from an aryl group. Aryl groups are mono-, di- or tri-substituted by one, two or three radicals selected from alkyl, alkoxy, aryl, hydroxy, halogen, cyano, amino, amino-alkyl, trifluoromethyl, alkylenedioxy and oxy-C$_2$-C$_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g., methylenedioxy or ethylenedioxy. Oxy-C$_2$-C$_3$-alkylene is also a divalent substituent attached to two adjacent carbon atoms of phenyl, e.g., oxyethylene or oxypropylene. An example for oxy-C$_2$-C$_3$-alkylene-phenyl is 2,3-dihydrobenzofuran-5-yl.

Aryl groups include, but are not limited to, naphthyl, phenyl or phenyl mono- or disubstituted by alkoxy, phenyl, halogen, alkyl or trifluoromethyl, phenyl or phenyl-mono- or disubstituted by alkoxy, halogen or trifluoromethyl, and in particular phenyl.

As used herein, the term "arylene" refers to an aryl group, as defined above, linking at least two other groups. The two moieties linked to the arylene are linked to different atoms of the arylene. Arylene groups include, but are not limited to, phenylene.

As used herein, the terms "alkoxy-aryl" or "aryloxy" refers to an aryl group, as defined above, where one of the moieties linked to the aryl is linked through an oxygen atom. Alkoxy-aryl groups include, but are not limited to, phenoxy (C$_6$H$_5$O$^-$). The present disclosure also includes alkoxy-heteroaryl or heteroaryloxy groups.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g., alkyl, nitro or halogen. Suitable groups for the present disclosure also include heteroarylene and heterarylene-oxy groups similar to the description above for arylene and arylene-oxy groups.

Similarly, aryl and heteroaryl groups described herein are substituted or unsubstituted. Substituents for the aryl and heteroaryl groups are varied, such as alkyl, aryl, CN, amino, sulfide, aldehyde, ester, ether, acid, hydroxyl or halide. In some aspects, a substituent is a reactive group, such as but not limited to chloro, bromo, iodo, hydroxyl, or amino. In certain aspects, a substituent is selected from: -halogen, —OR', —OC(O)R', —NR'R," —SR', —R', —CN, —NO$_2$, —CO$_2$R', —CONR'R," —C(O)R', —OC(O)NR'R," —NR"C(O)R', —NR"C(O)2R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R," —N$_3$, —CH(Ph)$_2$, in a number ranging from zero to the total number of open valences on the aromatic ring system; and where R', R" and R'" are independently selected from hydrogen, (C$_1$-C$_8$) alkyl and heteroalkyl, unsubstituted aryl and heteroaryl, (unsubstituted aryl)-(C$_1$-C$_4$) alkyl, and (unsubstituted aryl)oxy-(C$_1$-C$_4$) alkyl.

As used herein, the term "alkyl-aryl" refers to a radical having an alkyl component and an aryl component, where the alkyl component links the aryl component to the point of attachment. The alkyl component is as defined above, except that the alkyl component is at least divalent in order to link to the aryl component and to the point of attachment. In some aspects, the alkyl component is absent. The aryl component is as defined above. Examples of alkyl-aryl groups include, but are not limited to, benzyl. The present disclosure also includes alkyl-heteroaryl groups.

As used herein, the term "alkenyl-aryl" refers to a radical having both an alkenyl component and an aryl component, where the alkenyl component links the aryl component to the point of attachment. The alkenyl component is as defined above, except that the alkenyl component is at least divalent in order to link to the aryl component and to the point of attachment. The aryl component is as defined above. Examples of alkenyl-aryl include ethenyl-phenyl, among others. The present disclosure also includes alkenyl-heteroaryl groups.

As used herein, the term "alkynyl-aryl" refers to a radical having both an alkynyl component and an aryl component, where the alkynyl component links the aryl component to the point of attachment. The alkynyl component is as defined above, except that the alkynyl component is at least divalent in order to link to the aryl component and to the point of attachment. The aryl component is as defined above. Examples of alkynyl-aryl include ethynyl-phenyl, among others. The present disclosure also includes alkynyl-heteroaryl groups.

As will be appreciated by one of ordinary skill in the art, the various chemical terms defined herein are used for describing chemical structures of the polymers and monomers of the present disclosure. For example, in certain aspects, a variety of the monomer derivatives (e.g., BODIPY derivatives) include a variety of the chemical substituents and groups described herein. For example, in some aspects, derivatives of the various monomers are substituted with hydrogen, deuterium, alkyl, aralkyl, aryl, alkoxy-aryl, N-dialkyl-4-phenyl, N-diphenyl-4-phenyl, N-dialkoxyphenyl-4-phenyl, amino, sulfide, aldehyde, ester, ether, acid, and/or hydroxyl.

Non-limiting examples of semiconducting polymers include fluorene polymers (e.g., Poly(9,9-dihexylfluorenyl-2,7-diyl) (PDHF), Poly(9,9-dioctylfluorenyl-2,7-diyl) (PFO)), fluorene based copolymers (e.g., Poly[{9,9-dioctyl-2,7-divinylene-fluorenylene}-alt-co-{2-methoxy-5-(2-ethylhexyloxy)-1,4-phenylene}] (PFPV), Poly[(9,9-dioctyl-fluorenyl-2,7-diyl)-co-(1,4-benzo-{2,1,3}-thiadiazole)] (PFBT), Poly[(9,9-dioctylfluorenyl-2,7-diyl)-co-(4,7-Di-2-thienyl-2,1,3-benzothiadiazole)] (PFTBT), Poly[(9,9-dioctylfluorenyl-2,7-diyl)-9-co-(4,7-Di-2-thienyl-2,1,3-benzothiadiazole)] (PF-0.1TBT)), phenylene vinylene polymers (e.g., Poly[2-methoxy-5-(2-ethylhexyloxy)-1,4-phenylenevinylene] (MEH-PPV)), poly[2-methoxy-5-(2-ethylhexyloxy)-1,4-(1-cyanovinylene-1,4-phenylene)] (CN-PPV), BODIPY 570, BODIPY 590, BODIPY 690, and other polymers that are used to make narrow band chromophoric polarization-sensitive nanoparticles (e.g., BODIPY-based chromophoric polarization-sensitive nanoparticles) such as those described in PCT/US12/71767, which is herein incorporated by reference in its entirety).

The present disclosure can include polarization-sensitive nanoparticles, e.g., emissive chromophoric polarization-sensitive nanoparticles. For example, the present disclosure can include a homopolymer or heteropolymer including, for example, BODIPY and/or BODIPY derivative monomer, a squaraine and/or squaraine derivative, a metal complex and/or metal complex derivative monomer, a porphyrin and/or porphyrin derivative monomer, a phthalocyanine and/or phthalocynanine derivative monomer, a lanthanide complex and/or lanthanide complex derivative monomer, a perylene and/or perylene derivative monomer, a cyanine and/or cyanine derivative monomer, a rhodamine and/or rhodamine derivative monomer, a coumarin and/or coumarin derivative monomer, and/or a xanthene and/or xanthene derivative monomer.

In some aspects, the present disclosure provides polarization-sensitive nanoparticles comprising a BODIPY derivative having the structure of Formula (I):

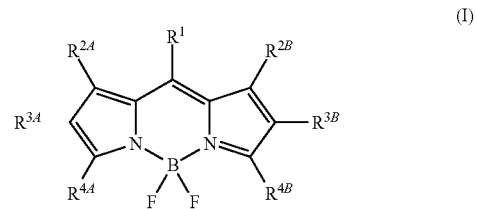

(I)

wherein each of $R^1$, $R^{2A}$, $R^{2B}$, $R^{3A}$, $R^{3B}$, $R^{4A}$ and $R^{4B}$ is independently selected from hydrogen, alkyl, aralkyl, aryl, or alkoxy-aryl, and wherein the BODIPY derivative is integrated into the chromophoric polymer by attachment to $R^1$, $R^{2A}$, $R^{2B}$, $R^{3A}$, $R^{3B}$, $R^{4A}$, $R^{4B}$ or a combination thereof.

BODIPY and a variety of BODIPY derivatives are used for the present disclosure. BODIPY and BODIPY derivatives are polymerized to form polymers (e.g., homopolymers or heteropolymers) and/or are attached (e.g., covalently attached) to a polymer backbone, sidechain and/or terminus. In some aspects, the chromophoric polarization-sensitive nanoparticles of the present disclosure can include a polymer that includes a monomer having the structure of Formula (I):

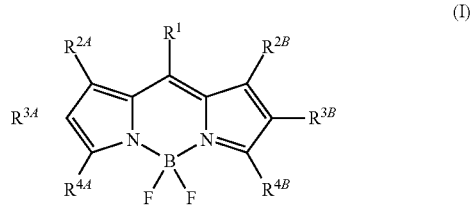

(I)

wherein each of $R^1$, $R^{2A}$, $R^{2B}$, $R^{3A}$, $R^{3B}$, $R^{4A}$ and $R^{4B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-) substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-) substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-) substituted benzooxadizolyl, benzothiadizolyl, alkyl-(alkoxy-, aryl-, fluoroalkyl-, fluoroaryl-) substituted benzothiadizolyl, fluorenyl, alkyl-(alkoxy-, aryl-, fluoroalkyl-, fluoroaryl-) substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The monomer are integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, $R^{3B}$, $R^{4A}$ and $R^{4B}$ or a combination thereof.

In some aspects, the chromophoric polarization-sensitive nanoparticles of the present disclosure can include a polymer that includes a monomer having the structure of Formula (II):

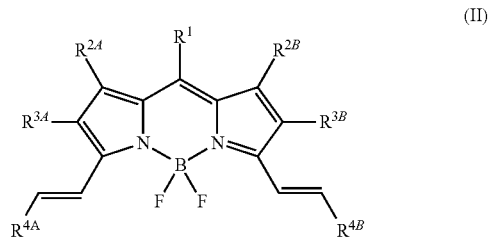

(II)

wherein each of $R^1$, $R^{2A}$, $R^{2B}$, $R^{3A}$, $R^{3B}$, $R^{4A}$ and $R^{4B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-) substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-) substituted benzooxadizolyl, benzothiadizolyl, alkyl-(alkoxy-, aryl-, fluoroalkyl-, fluoroaryl-) substituted benzothiadizolyl, fluorenyl, alkyl-(alkoxy-, aryl-, fluoroalkyl-, fluoroaryl-) substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl- 4-phenyl, and N-dialkoxyphenyl-4-phenyl. The monomer are integrated into a backbone of the polymer (e.g., polymerized in the polymer) and/or covalently attached to the backbone, a terminus, or a sidechain of the polymer through at least one attachment to R1, R2A, R2B, R3A, R3B, R4A, R4B or a combination thereof. The monomer can, for example, integrate with the backbone of the polymer by attachment to the R3A and R3B groups.

In some aspects, the chromophoric polarization-sensitive nanoparticles of the present disclosure can include a polymer that includes a monomer having the structure of Formula (III):

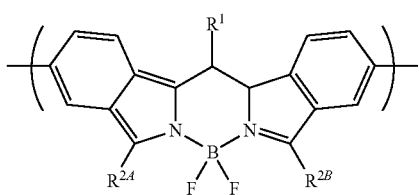

(III)

wherein each of $R^1$, $R^{2A}$ and $R^{2B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-) substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-) substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The monomer are integrated into a backbone of the polymer (e.g., polymerized in the polymer) and/or covalently attached to the backbone, a terminus, or a sidechain of the polymer through at least one attachment, e.g., to $R^1$, $R^{2A}$ and $R^{2B}$, or a combination thereof. The parentheses indicate points of attachment of the monomer to the backbone of the polymer.

In some aspects, the chromophoric polarization-sensitive nanoparticles of the present disclosure can include a polymer that includes a monomer having the structure of Formula (IV):

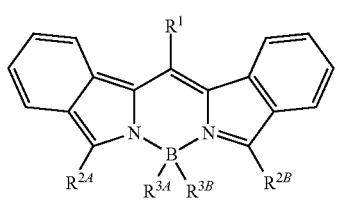

(IV)

wherein each of $R^1$, $R^{2A}$, $R^{2B}$, $R^{3A}$, $R^{3B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-) substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-) substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The monomer is integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, $R^{3B}$ or a combination thereof.

In some aspects, the chromophoric polarization-sensitive nanoparticles of the present disclosure can include a polymer that includes a monomer having the structure of Formula (V):

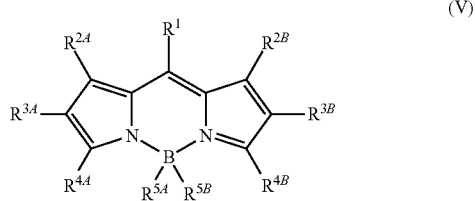

(V)

wherein each of $R^1$, $R^{2A}$, $R^{2B}$, $R^{3A}$, $R^{3B}$, $R^{4A}$, $R^{4B}$, $R^{5A}$ and $R^{5B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-) substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The monomer is integrated into a backbone of the polymer (e.g., copolymerized in the polymer) and/or covalently attached to the backbone, a terminus, or a sidechain of the polymer through at least one attachment to $R^1$, $R^{2A}$, $R^{2B}$, $R^{3A}$, $R^{3B}$, $R^{4A}$, $R^{4B}$, $R^{5A}$, $R^{5B}$, or a combination thereof. In certain embodiments, the monomers are integrated into the backbone by attachment to the $R^{5A}$ and $R^{5B}$ groups.

In some aspects, the chromophoric polarization-sensitive nanoparticles of the present disclosure can include a polymer that includes a monomer having the structure of Formula (VI):

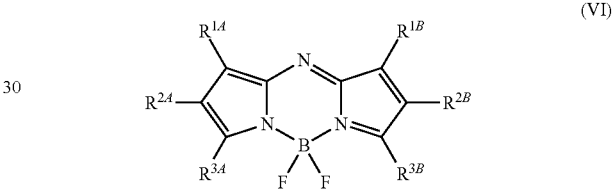

(VI)

wherein each of $R^1$, $R^{2A}$, $R^{2B}$, $R^{3A}$, $R^{3B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-) substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The monomer can be integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, $R^{3B}$ or a combination thereof.

In some aspects, the chromophoric polarization-sensitive nanoparticles of the present disclosure can include a polymer that includes a monomer having the structure of Formula (VII):

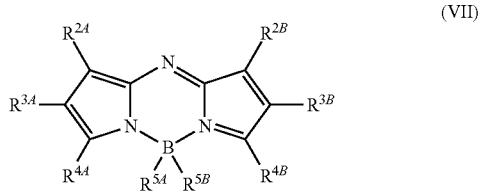

(VII)

wherein each of $R^{2A}$, $R^{2B}$, $R^{3A}$, $R^{3B}$, $R^{4A}$, $R^{4B}$, $R^{5A}$ and $R^{5B}$, is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-) substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-) substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-) substituted benzooxadizolyl, benzothiadizolyl, alkyl-(alkoxy-, aryl-, fluoroalkyl-, fluoroaryl-) substituted benzothiadizolyl, fluorenyl, alkyl-(alkoxy-, aryl-, fluoroalkyl-, fluoroaryl-) substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The monomer can be integrated into a backbone of the polymer (e.g., polymerized in the polymer) and/or covalently attached to the backbone, a terminus, or a sidechain of the polymer) through at least one attachment $R^{2A}$, $R^{2B}$, $R^{3A}$, $R^{3B}$, $R^{4A}$, $R^{4B}$, $R^{5A}$ and $R^{5B}$, or a combination thereof.

In some aspects, the chromophoric polarization-sensitive nanoparticles of the present disclosure can include a polymer that includes a monomer having the structure of formula (VIII):

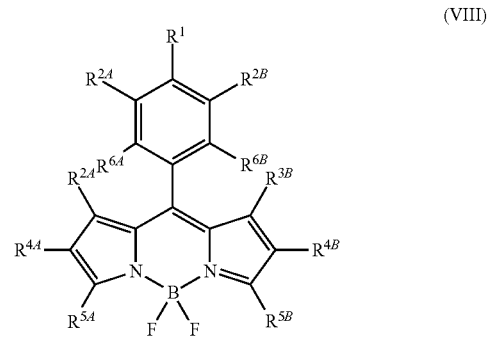

(VIII)

wherein each of $R^1$, $R^{2A}$, $R^{2B}$, $R^{3A}$, $R^{3B}$, $R^{4A}$, $R^{4B}$, $R^{5A}$, $R^{5B}$, $R^{6A}$ and $R^{6B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-) substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-) substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl, and wherein each of R5A, R5B, R6A and R6B are independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —(OCH$_2$CH$_2$)$_n$OH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-) substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-) substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The monomer can be integrated into a backbone of the polymer (e.g., copolymerized in the polymer) and/or covalently attached to the backbone, a terminus, or a sidechain of the polymer) through at least one attachment to R$^1$, R$^{2A}$, R$^{2B}$, R$^{3A}$, R$^{3B}$, R$^{4A}$, R$^{4B}$, R$^{5A}$, R$^{5B}$, R$^{6A}$, R$^{6B}$ or a combination thereof.

In some aspects, the chromophoric polarization-sensitive nanoparticles of the present disclosure can include a polymer that includes a monomer having the structure of Formula (IX):

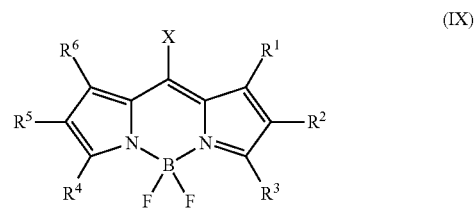

(IX)

wherein X has the structure of any one of Formulae (X), (XI), (XII), or (XIII) or their derivatives:

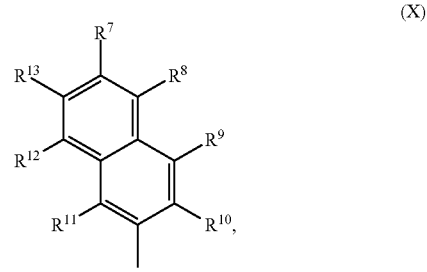

(X)

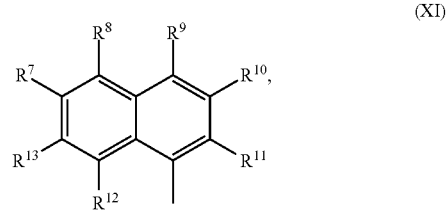

(XI)

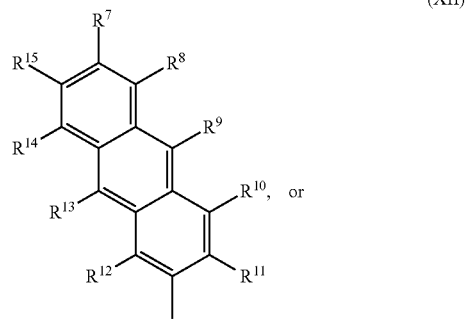

(XII)

-continued

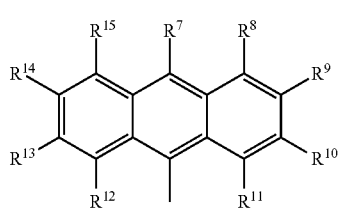

(XIII)

and wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ in Formulae (X), (XI), (XII), and (XIII) is independently selected from the group consisting of hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-) substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-) substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. When X represents naphthalene and its derivatives, the monomer are integrated into a backbone (e.g., polymerized in the polymer) and/or covalently attached to the backbone, a terminus, or a sidechain of the polymer) of the polymer through at least one attachment to $R^7$, $R^8$, $R^9$, $R^{10}$, $R^{11}$, $R^{12}$ or a combination thereof. When X represents anthracene and its derivatives, the monomer are integrated into a backbone of the polymer and/or covalently attached to the backbone, a terminus, or a sidechain of the polymer through at least one attachment to $R^7$, $R^8$, $R^9$, $R^{10}$, $R^{11}$, $R^{12}$, $R^{13}$, $R^{14}$, $R^{15}$ or a combination thereof.

In some aspects, the present disclosure provides polarization-sensitive nanoparticles comprising the chromophoric polymer, poly[(9,9-dioctylfluorenyl-2,7-diyl)-co-(4,7-di-2-thienyl-2,1,3-benzothiadiazole)] (PFTBT).

In some aspects of the present disclosure, chromophoric polarization-sensitive nanoparticles used for detection comprise the polymer, CN-PPV, which is a bright, compact, and orange-emitting semiconducting polymer hybrid nanoparticle also known as, poly[2-methoxy-5-(2-ethylhexyloxy)-1,4-(1-cyanovinylene-1,4-phenylene)]. CN-PPV has superior fluorescence properties, such as a large absorption cross-section, high quantum yield, and a fast emission rate.

In some aspects, the chromophoric polymer hybrid nanoparticle used for detecting proteins and peptides can comprises a polymer that consists essentially of CN-PPV. In some aspects, the hybrid nanoparticle includes CN-PPV and at least one other material. For example, the CN-PPV is mixed with a copolymer or other material that provides an additional functionality.

In some aspects, the polarization-sensitive nanoparticles used for the detection of proteins and peptides can include a semiconducting copolymer having at least two different chromophoric units. For example, a conjugated copolymer can contain both fluorene and benzothiazole chromophoric units present at a given ratio. Typical chromophoric units used to synthesize semiconducting copolymers include, but are not limited to fluorene unit, phenylene vinylene unit, phenylene unit, phenylene ethynylene unit, benzothiazole unit, thiophene unit, carbazole fluorene unit, boron-dipyrromethene unit, and derivatives thereof. The different chromophoric units are segregated, as in a block copolymer, or intermingled. As used herein, a chromophoric copolymer is represented by writing the identity of the major chromophoric species. For example, PFBT is a chromophoric polymer containing fluorene and benzothiazole units at a certain ratio. In some aspects, a dash is used to indicate the percentage of the minor chromophoric species and then the identity of the minor chromophoric species. For example, PF-0.1 BT is a chromophoric copolymer containing 90% PF and 10% BT.

In some aspects, chromophoric polarization-sensitive nanoparticles are pi-conjugated species with luminescent properties. The chromophoric polarization-sensitive nanoparticles may comprise polymers with one or more repeating units, which are combined in fixed, ordered, or random configurations and ratios. In some aspects, a repeating unit is a monomer or a chemical motif that occurs throughout the polymer, such as an aromatic or heterocyclic unit.

In some aspects, the polymers are halogenated, for example, fluorinated, chlorinated, brominated, or iodinated. In some aspects, a polymer, a repeating unit, or a monomer are halogenated at one or multiple sites. A halogenated polymer, for example, a fluorinated polymer, can provide greater levels of fluorescence than can a non-halogenated analogous polymer.

In some aspects, the chromophoric polymer hybrid nanoparticle comprises polymers bearing units of small organic dye molecules, metal complexes, photochotochromic dye, and any combinations thereof, for example, optically inactive polymers such as polystyrene covalently linked or grafted with small organic dye, metal complexes, photochromic dyes and any combination thereof. In some aspects, these dyes or metal complexes have sensing functions, such as oxygen sensing capability, ion sensing capability, glucose sensing capability, neurotransmitter sensing capability, drug sensing capability, metabolite sensing capability, protein sensing capability, signaling molecule sensing capability, toxin sensing capability, DNA and RNA sensing capability, and the like.

In some aspects, the chromophoric polymer hybrid nanoparticle comprises semiconducting polymers covalently linked with small organic dye molecules, metal complexes, photochromic dye, and any combinations thereof as emissive units. Such emissive units can tune the emission color, increase the quantum yield, and improve the photostability of the chromophoric polymer hybrid nanoparticle. In certain aspects, the small organic dyes, or metal complexes can have sensing functions, and therefore add additional functionalities to the chromophoric polymer hybrid nanoparticle, such as oxygen sensing capability, ion sensing capability, glucose sensing capability, neurotransmitter sensing capability, drug sensing capability, metabolite sensing capability, protein sensing capability, signaling molecule sensing capability, toxin sensing capability, DNA and RNA sensing capability, and the like.

In some aspects, the chromophoric polarization-sensitive nanoparticles also comprise semiconducting polymer, physically mixed or chemically cross-linked with other chromophoric polymer such as optically inactive polymer covalently linked or grafted with small organic dye, metal complexes, photochromic dyes and any combination thereof, to have additional functionalities such as oxygen sensing capability, ion sensing capability, glucose sensing capability, neurotransmitter sensing capability, drug sensing capability, metabolite sensing capability, protein sensing capability, signaling molecule sensing capability, toxin sensing capability, DNA and RNA sensing capability, and the like.

In some aspects, the chromophoric polymer hybrid nanoparticle also comprise semiconducting polymer, physically mixed or chemically cross-linked with other components including, e.g., fluorescent dye, inorganic luminescent materials, magnetic materials, metal materials, to tune emission color, improve quantum yield and photostability, and have additional functionalities such as magnetic functions, plasmon resonance functions, and the like.

Matrix Polymers

The First Matrix Polymer.

In various aspects, the present disclosure provides polarization-sensitive nanoparticles comprising: a chromophoric polymer; a first matrix polymer; and a second matrix polymer, wherein the polarization-sensitive nanoparticle has at least one critical dimension of 1 nm to 1000 nm.

In some aspects, the polarization-sensitive nanoparticle comprises a first matrix polymer that is a non-semiconducting polymer. In certain aspects, the first matrix polymer is an amphiphilic polymer.

In certain aspects, the first matrix polymer is selected from a poly((meth)acrylic acid)-based copolymer, a polydiene-based copolymer, a poly(ethylene oxide)-based copolymer, a polyisobutylene-based copolymer, a polystyrene-based copolymer, a polysiloxane-based copolymer, a poly(ferrocenyldimethylsilane)-based copolymer, a poly(2-vinyl naphthalene)-based copolymer, a poly (vinyl pyridine and N-methyl vinyl pyridinium iodide)-based copolymer, a poly (vinyl pyrrolidone)-based copolymer, a polyacrylamide-based copolymer, a poly(meth)acrylate-based copolymer, a polyphenylene-based copolymer, a polyethylene-based copolymer, a poly(ethylene glycol)-based copolymer, a polylactide-based copolymer, a polyurethane-based copolymer, or a combination thereof.

In further aspects, the first matrix polymer is selected from poly(acrylic acid-b-acrylamide), poly(acrylic acid-b-methyl methacrylate), poly(acrylic acid-b-N-isopropylacrylamide), poly(n-butylacrylate-b-acrylic acid), poly(sodium acrylate-b-methyl methacrylate), poly(methacrylic acid-b-neopentyl methacrylate), poly(methyl methacrylate-b-acrylic acid), poly(methyl methacrylate-b-methacrylic acid), poly(methyl methacrylate-b-N,N-dimethyl acrylamide), poly(methyl methacrylate-b-sodium acrylate), poly(methyl methacrylate-b-sodium methacrylate), poly(neopentyl methacrylate-b-methacrylic acid), polystyrene-graft-poly (ethylene oxide), poly(t-butyl methacrylate-b-ethylene oxide), poly(2-acrylamido-2-methylpropanesulfonic acid-b-acrylic acid), poly(butadiene(1,2 addition)-b-ethylene oxide), poly(butadiene(1,2 addition)-b-methylacrylic acid, poly(butadiene(1,4 addition)-b-acrylic acid), poly(butadiene (1,4 addition)-b-ethylene oxide, poly(butadiene(1,4 addition)-b-sodium acrylate), poly(butadiene(1,4 addition)-b-N-methyl 4-vinyl pyridinium iodide), poly(isoprene-b-ethylene oxide), poly(isoprene-b-ethylene oxide), and poly (isoprene-b-N-methyl 2-vinyl pyridinium iodide), poly (ethylene oxide-b-acrylic acid), poly(ethylene oxide-b-acrylamide), poly(ethylene oxide-b-butylene oxide), poly (ethylene oxide-b-c-caprolactone), poly(ethylene oxide-b-lactide), poly(ethylene oxide-b-lactide), poly(ethylene oxide-b-methacrylic acid), poly(ethylene oxide-b-methyl acrylate), poly(ethylene oxide-b-N-isopropylacrylamide), poly(ethylene oxide-b-methyl methacrylate), poly(ethylene oxide-b-nitrobenzyl methacrylate), poly(ethylene oxide-b-N,N-dimethylaminoethylmethacrylate), poly(ethylene oxide-b-propylene oxide), poly(ethylene oxide-b-t-butyl acrylate), poly(ethylene oxide-b-t-butyl methacrylate), poly (ethylene oxide-b-tetrahydrofurfuryl methacrylate), poly (ethylene oxide-b-2-ethyl oxazoline), poly(ethylene oxide-b-2-hydroxyethyl methacrylate), poly(ethylene oxide-b-2-methyl oxazoline), poly(isobutylene-b-acrylic acid), poly (isobutylene-b-ethylene oxide), poly(isobutylene-b-methacrylic acid), poly(styrene-b-acrylamide), poly (styrene-b-acrylic acid), poly(styrene-b-cesium acrylate), poly(styrene-b-ethylene oxide), poly(styrene-b-ethylene oxide) acid cleavable at the block junction, poly(styrene-b-methacrylic acid), poly(4-styrenesulfonic acid-b-ethylene oxide), poly(styrenesulfonic acid-b-methylbutylene), poly (styrene-b-N,N-dimethylacrylamide), poly(styrene-b-N-isopropyl acrylamide), poly(styrene-b-N-methyl 2-vinyl pyridinium iodide), poly(styrene-b-N-methyl-4-vinyl pyridinium iodide), poly(styrene-b-propylacrylic acid), poly (styrene-b-sodium acrylate)poly(styrene-b-sodium methacrylate), polyp-chloromethyl styrene-b-acrylamide), poly (styrene-co-p-chloromethyl styrene-b-acrylamide), poly (styrene-co-p-chloromethyl styrene-b-acrylic acid), poly (styrene-b-methylbutylene-co-isoprene sulfonate), poly (dimethylsiloxane-b-acrylic acid), poly(dimethylsiloxane-b-ethylene oxide), poly(dimethylsiloxane-b-methacrylic acid), poly(ferrocenyldimethylsilane-b-ethylene oxide), poly(-vinyl naphthalene-b-acrylic acid), poly(-vinyl pyridine-b-ethylene oxide), poly(-vinyl pyridine-b-methyl acrylic acid), poly(N-methyl 2-vinyl pyridinium iodide-b-ethylene oxide), poly(N-methyl 4-vinyl pyridinium iodide-b-methyl methacrylate), poly(-vinyl pyridine-b-ethylene oxide) PEO end functional OH, poly(vinyl pyrrolidone-b-D/L-lactide, 60% dodecyl-grafted-poly (isobutylene-alt-maleic anhydride) (P60), 70% dodecyl-grafted-poly (isobutylene-alt-maleic anhydride) (P70), 80% dodecyl-grafted-poly (isobutylene-alt-maleic anhydride) (P80), or a combination thereof.

In some aspects, the first matrix polymer is polystyrene-graft-poly(ethylene oxide).

In some aspects, first matrix polymer is a block copolymer, a random copolymer, or an alternating copolymer.

The Second Matrix Polymer.

In some aspects, the polarization-sensitive nanoparticle comprises a second matrix polymer that is a non-semiconducting polymer. In certain aspects, the first matrix polymer is an amphiphilic polymer.

In certain aspects, the second matrix polymer is selected from a poly((meth)acrylic acid)-based copolymer, a polydiene-based copolymer, a poly(ethylene oxide)-based copolymer, a polyisobutylene-based copolymer, a polystyrene-based copolymer, a polysiloxane-based copolymer, a poly(ferrocenyldimethylsilane)-based copolymer, a poly(-vinyl naphthalene)-based copolymer, a poly (vinyl pyridine and N-methyl vinyl pyridinium iodide)-based copolymer, a poly (vinyl pyrrolidone)-based copolymer, a polyacrylamide-based copolymer, a poly(meth)acrylate-based copolymer, a polyphenylene-based copolymer, a polyethylene-based copolymer, a poly(ethylene glycol)-based copolymer, a polylactide-based copolymer, a polyurethane-based copolymer, or a combination thereof.

In further aspects, the second matrix polymer is selected from poly(acrylic acid-b-acrylamide), poly(acrylic acid-b-methyl methacrylate), poly(acrylic acid-b-N-isopropylacrylamide), poly(n-butylacrylate-b-acrylic acid), poly(sodium acrylate-b-methyl methacrylate), poly(methacrylic acid-b-neopentyl methacrylate), poly(methyl methacrylate-b-acrylic acid), poly(methyl methacrylate-b-methacrylic acid), poly(methyl methacrylate-b-N,N-dimethyl acrylamide), poly(methyl methacrylate-b-sodium acrylate), poly(methyl methacrylate-b-sodium methacrylate), poly(neopentyl methacrylate-b-methacrylic acid), polystyrene-graft-poly (ethylene oxide), poly(t-butyl methacrylate-b-ethylene oxide), poly(2-acrylamido-2-methylpropanesulfonic acid-b-acrylic acid), poly(butadiene(1,2 addition)-b-ethylene oxide), poly(butadiene(1,2 addition)-b-methylacrylic acid, poly(butadiene(1,4 addition)-b-acrylic acid), poly(butadiene (1,4 addition)-b-ethylene oxide, poly(butadiene(1,4 addition)-b-sodium acrylate), poly(butadiene(1,4 addition)-b-N-methyl 4-vinyl pyridinium iodide), poly(isoprene-b-ethylene oxide), poly(isoprene-b-ethylene oxide), and poly (isoprene-b-N-methyl 2-vinyl pyridinium iodide), poly (ethylene oxide-b-acrylic acid), poly(ethylene oxide-b-acrylamide), poly(ethylene oxide-b-butylene oxide), poly (ethylene oxide-b-c-caprolactone), poly(ethylene oxide-b-lactide), poly(ethylene oxide-b-lactide), poly(ethylene oxide-b-methacrylic acid), poly(ethylene oxide-b-methyl acrylate), poly(ethylene oxide-b-N-isopropylacrylamide), poly(ethylene oxide-b-methyl methacrylate), poly(ethylene oxide-b-nitrobenzyl methacrylate), poly(ethylene oxide-b-N,N-dimethylaminoethylmethacrylate), poly(ethylene oxide-b-propylene oxide), poly(ethylene oxide-b-t-butyl acrylate), poly(ethylene oxide-b-t-butyl methacrylate), poly (ethylene oxide-b-tetrahydrofurfuryl methacrylate), poly (ethylene oxide-b-2-ethyl oxazoline), poly(ethylene oxide-b-2-hydroxyethyl methacrylate), poly(ethylene oxide-b-2-methyl oxazoline), poly(isobutylene-b-acrylic acid), poly (isobutylene-b-ethylene oxide), poly(isobutylene-b-methacrylic acid), poly(styrene-b-acrylamide), poly (styrene-b-acrylic acid), poly(styrene-b-cesium acrylate), poly(styrene-b-ethylene oxide), poly(styrene-b-ethylene oxide) acid cleavable at the block junction, poly(styrene-b-methacrylic acid), poly(4-styrenesulfonic acid-b-ethylene oxide), poly(styrenesulfonic acid-b-methylbutylene), poly (styrene-b-N,N-dimethylacrylamide), poly(styrene-b-N-isopropyl acrylamide), poly(styrene-b-N-methyl 2-vinyl pyridinium iodide), poly(styrene-b-N-methyl-4-vinyl pyridinium iodide), poly(styrene-b-propylacrylic acid), poly (styrene-b-sodium acrylate)poly(styrene-b-sodium methacrylate), polyp-chloromethyl styrene-b-acrylamide), poly (styrene-co-p-chloromethyl styrene-b-acrylamide), poly (styrene-co-p-chloromethyl styrene-b-acrylic acid), poly (styrene-b-methylbutylene-co-isoprene sulfonate), poly (dimethylsiloxane-b-acrylic acid), poly(dimethylsiloxane-b-ethylene oxide), poly(dimethylsiloxane-b-methacrylic acid), poly(ferrocenyldimethylsilane-b-ethylene oxide), poly(2-vinyl naphthalene-b-acrylic acid), poly(2-vinyl pyridine-b-ethylene oxide), poly(2-vinyl pyridine-b-methyl acrylic acid), poly(N-methyl 2-vinyl pyridinium iodide-b-ethylene oxide), poly(N-methyl 4-vinyl pyridinium iodide-b-methyl methacrylate), poly(4-vinyl pyridine-b-ethylene oxide) PEO end functional OH, poly(vinyl pyrrolidone-b-D/L-lactide, 60% dodecyl-grafted-poly(isobutylene-alt-maleic anhydride) (P60), 70% dodecyl-grafted-poly(isobutylene-alt-maleic anhydride) (P70), 80% dodecyl-grafted-poly(isobutylene-alt-maleic anhydride) (P80), or a combination thereof.

In some aspects, the second matrix polymer is polystyrene-graft-poly(ethylene oxide).

In some aspects, second matrix polymer is a block copolymer, a random copolymer, or an alternating copolymer.

In certain aspects, the second matrix polymer is P60, which is defined as an amphiphilic polymer of which 60% of the maleic anhydride rings in poly(isobutylene-alt-maleic anhydride) have been reacted with dodecylamine, leaving 40% of its anhydride rings. P60 is also known as 60% dodecyl-grafted-poly(isobutylene-alt-maleic anhydride).

In certain aspects, the second matrix polymer is P70, which is defined as an amphiphilic polymer of which 70% of the maleic anhydride rings in poly(isobutylene-alt-maleic anhydride) have been reacted with dodecylamine, leaving 30% of its anhydride rings. P70 is also known as 70% dodecyl-grafted-poly(isobutylene-alt-maleic anhydride).

In certain aspects, the second matrix polymer is P80, which is defined as an amphiphilic polymer of which 80% of the maleic anhydride rings in poly(isobutylene-alt-maleic anhydride) have been reacted with dodecylamine, leaving 20% of its anhydride rings. P80 is also known as 80% dodecyl-grafted-poly(isobutylene-alt-maleic anhydride).

The methods and compositions described herein further include polymers which are not semiconducting, for example, non-semiconducting polymers. In certain embodiments, a functionalized hybrid nanoparticle comprise a copolymer having one or more functionalized monomeric units, for example an amphiphilic polymer. As described herein, when designing a chromophoric hybrid nanoparticle containing an amphiphilic polymer, care should be taken to ensure the hydrophilic functional groups do not adversely affect the collapse of the polymer chain into a hybrid nanoparticle form or do not adversely affect the stability of the formed chromophoric polarization-sensitive nanoparticles. This is achieved, e.g., by adjusting the percentage of amphiphilic functionalization polymer relative to the chromophoric polymer.

Non-semiconducting polymers include any polymer which is used with the methods and compositions described herein that is not a semiconducting polymer, for example, a matrix polymer, a functionalization polymer or the like. In some aspects, a matrix polymer and a functionalization polymer are the same. In other embodiments, a matrix polymer and a functionalization polymer are different.

Other suitable polymers and chromophoric polarization-sensitive nanoparticles are provided, e.g., in WO2011/

057295, which is herein incorporated by reference in its entirety. As provided, e.g., in WO2011/057295, the polymers in the chromophoric polarization-sensitive nanoparticles are physically blended or chemically bonded (or chemically crosslinked). For example, the physically blended chromophoric polarization-sensitive nanoparticles can include polymers that are blended in the chromophoric polymer hybrid nanoparticle and held together by non-covalent interactions. Chemically bonded chromophoric polarization-sensitive nanoparticles can include polymers that are covalently attached to each other in the chromophoric polymer hybrid nanoparticle. In some aspects, the chemically bonded polymers are covalently attached to each other prior to formation of the chromophoric polarization-sensitive nanoparticles. In some aspects, the polymers and chromophoric polarization-sensitive nanoparticles can include those disclosed and claimed, e.g., in PCT/US11/56768. For example, the chromophoric polarization-sensitive nanoparticles can include those that are directly functionalized and/or have low density functionalization.

In some aspects, chromophoric polarization-sensitive nanoparticles are used that contain a comb-like polymer comprising carboxyl, amine, thiol, ester, succinimidyl ester, azide, alkyne, cyclooctyne, or phosphine groups. In some aspects, chromophoric polarization-sensitive nanoparticles are used that contain poly(methyl methacrylate) based comb-like polymers. Non-limiting examples of poly(methyl methacrylate) based comb-like polymers include, poly(methyl methacrylate) graft acrylic acid, poly(methyl methacrylate) graft ethylene oxide, and the like.

Blends of Polymers

In certain embodiments, the polarization-sensitive nanoparticles can include a blend of semiconducting polymers. The blends can include any combination of homopolymers, copolymers, and oligomers. Polymer blends used to form polarization-sensitive nanoparticles are selected in order to tune the properties of the resulting polarization-sensitive nanoparticles, for example, to achieve a desired excitation or emission spectra for the polymer hybrid nanoparticle.

In some aspects, the polarization-sensitive nanoparticles can include a blend of semiconducting polymers and non-semiconducting polymers. The blends can include any combination of homopolymers, copolymers, and oligomers. Polymer blends used to form polarization-sensitive nanoparticles are selected in order to tune the properties of the resulting polarization-sensitive nanoparticles, for example, to achieve a desired excitation or emission spectra for the polymer hybrid nanoparticle.

In various aspects, blends of polymers are performed such that the blend includes polymers at a ratio, for example, a mass ratio. In some aspects, the mass ratio is a low mass ratio, for example, where the mass of the semiconducting polymer is low relative to the mass of the non-semiconducting polymers. A low mass ratio is a ratio where the percent of semiconducting polymer mass in a hybrid nanoparticle is less than 50% of the total mass of the hybrid nanoparticle. In some aspects, the percent of semiconducting polymer mass in a hybrid nanoparticle is less than 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1% or 0.5%. In some aspects, the percent of semiconducting polymer mass in a hybrid nanoparticle is from 50%-45%, 45%-40%, 40%-35%, 35%-30%, 30%-25%, 25%-20%, 20%-19%, 19%-18%, 18%-17%, 17%-16%, 16%-15%, 15%-14%, 14%-13%, 13%-12%, 12%-11%, 11% 10%, 10%-9%, 9%-8%, 8%-7%, 7%-6%, 6%-5%, 5%-4%, 4%-3%, 3%-2%, 2%-1% or 1%-0.5%.

In some aspects, the total mass of a polymer are less than 20 kDa, 19 kDa, 18 kDa, 17 kDa, 16 kDa, 15 kDa, 14 kDa, 13 kDa, 12 kDa, 11 kDa, 10 kDa, 9 kDa, 8 kDa, 7 kDa, 6 kDa, 5 kDa, 4 kDa, 3 kDa, 2 kDa, 1 kDa or 0.5 kDa. In some aspects, the percent of semiconducting polymer mass in a hybrid nanoparticle is from 20 kDa-19 kDa, 19 kDa-18 kDa, 18 kDa-17 kDa, 17 kDa-16 kDa, 16 kDa-15 kDa, 15 kDa-14 kDa, 14 kDa-13 kDa, 13 kDa-12 kDa, 12 kDa-11 kDa, 11 kDa 10 kDa, 10 kDa-9 kDa, 9 kDa-8 kDa, 8 kDa-7 kDa, 7 kDa-6 kDa, 6 kDa-5 kDa, 5 kDa-4 kDa, 4 kDa-3 kDa, 3 kDa-2 kDa, 2 kDa-1 kDa or 1 kDa-0.5 kDa.

In some aspects, the blend of polymers may comprise 1, 2, 3, 4, 5, 6, 7, 8, 9, 10, 11, 12, 13, 14, 15, 16, 17, 18, 19 or less than 20 chains of a single polymer. In other embodiments, the blend of polymers may comprise 1 single chain of a single polymer. In various aspects, the single polymer chain in a blend of polymers is a single chain of a semiconducting polymer.

In some aspects, a blend of polymers is formed into a hybrid nanoparticle. The hybrid nanoparticle may comprise a blend includes polymers at a ratio, for example, a mass ratio. In some aspects, the mass ratio is a low mass ratio, for example, where the mass of the semiconducting polymer is low relative to the mass of the non-semiconducting polymers. A low mass ratio is a ratio where the percent of semiconducting polymer mass in a hybrid nanoparticle is less than 50% of the total mass of the hybrid nanoparticle. In some aspects, the percent of semiconducting polymer mass in a hybrid nanoparticle is less than 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1% or 0.5%. In some aspects, the percent of semiconducting polymer mass in a hybrid nanoparticle is from 50%-45%, 45%-40%, 40%-35%, 35%-30%, 30%-25%, 25%-20%, 20%-19%, 19%-18%, 18%-17%, 17%-16%, 16%-15%, 15%-14%, 14%-13%, 13%-12%, 12%-11%, 11% 10%, 10%-9%, 9%-8%, 8%-7%, 7%-6%, 6%-5%, 5%-4%, 4%-3%, 3%-2%, 2%-1% or 1%-0.5%.

In some aspects, a blend of polymers are formed into a hybrid nanoparticle where each polymer in the hybrid nanoparticle wherein the total mass of a polymer are less than 20 kDa, 19 kDa, 18 kDa, 17 kDa, 16 kDa, 15 kDa, 14 kDa, 13 kDa, 12 kDa, 11 kDa, 10 kDa, 9 kDa, 8 kDa, 7 kDa, 6 kDa, 5 kDa, 4 kDa, 3 kDa, 2 kDa, 1 kDa or 0.5 kDa. In some aspects, the percent of semiconducting polymer mass in a hybrid nanoparticle is from 20 kDa-19 kDa, 19 kDa-18 kDa, 18 kDa-17 kDa, 17 kDa-16 kDa, 16 kDa-15 kDa, 15 kDa-14 kDa, 14 kDa-13 kDa, 13 kDa-12 kDa, 12 kDa-11 kDa, 11 kDa 10 kDa, 10 kDa-9 kDa, 9 kDa-8 kDa, 8 kDa-7 kDa, 7 kDa-6 kDa, 6 kDa-5 kDa, 5 kDa-4 kDa, 4 kDa-3 kDa, 3 kDa-2 kDa, 2 kDa-1 kDa or 1 kDa-0.5 kDa.

In some aspects, the blend of polymers may form a hybrid nanoparticle and the hybrid nanoparticle may comprise 1, 2, 3, 4, 5, 6, 7, 8, 9, 10, 11, 12, 13, 14, 15, 16, 17, 18, 19 or less than 20 chains of a single polymer. In other embodiments, the blend of polymers may comprise 1 single chain of a single polymer. In various aspects, the single polymer chain in a blend of polymers is a single chain of a semiconducting polymer.

One case of the present disclosure provides functionalized chromophoric polymers that form stable hybrid nanoparticles. As used herein, the term "stable," can refer to chromophoric polarization-sensitive nanoparticles that do not aggregate and/or change substantially in size (as measured by electron microscopy, atomic force microscopy, or dynamic light scattering) when stored in an appropriate aqueous solution for an extended period of time. Aggregation or a change substantially in size of the polarization-sensitive nanoparticles can, for example, be characterized as an increasing number of aggregates including more than one polymer hybrid nanoparticle. Aggregates are detected visually by the eye, with imaging techniques, such as electron microscopy or atomic for microscopy, and/or by increased size measurements shown by dynamic light scattering. In some aspects, aggregation are characterized by at least about a 10% increase, at least about a 25% increase, at least about a 50% increase, at least about a 100% increase, at least about a 500% increase, or at least about a 1000% increase in measured particle diameter as compared to an original measurement of the chromophoric polarization-sensitive nanoparticles. For example, chromophoric polarization-sensitive nanoparticles may measure a median diameter of 15 nm on day one, and then measure a median diameter of 30 nm four months later, thereby showing a 100% increase in measured particle diameter (i.e., exhibiting aggregation). In certain embodiments, the chromophoric polarization-sensitive nanoparticles are stable when stored in an appropriate aqueous solution for at least about a month, preferably at least about 2 months, more preferably at least about 4 months. In certain embodiments, a stable chromophoric hybrid nanoparticle will not aggregate or change substantially in size for at least about 1, 2, 3, 4, 5, 6, 7, 8, 9, 10, 11, 12, 13, 14, 15, 16, 17, 18, 19, 20, 21, 22, 23, 24, 30, 36, 42, 48, or more months. In one case, a functionalized chromophoric hybrid nanoparticle as provided herein will remain stable in an appropriate aqueous solution for at least about 4 months. In another case, a functionalized chromophoric hybrid nanoparticle as provided herein will remain stable in an appropriate aqueous solution for at least about 6 months. In a yet another case, a functionalized chromophoric hybrid nanoparticle as provided herein will remain stable in an appropriate aqueous solution for at least about one year.

In some aspects, the term "stable" can refer to a chromophoric polymer hybrid nanoparticle resistance to dissociation of polymer molecules or dopants in the polymer hybrid nanoparticle. For example, chromophoric polarization-sensitive nanoparticles can include several polymer molecules and those polymer molecules can stay in the polymer hybrid nanoparticle for a period of time before leaching out into solution. Leaching of polymer molecules from polarization-sensitive nanoparticles are characterized, for example, by decreased photophysical properties of the polarization-sensitive nanoparticles. In some aspects, decreased stability of the chromophoric polarization-sensitive nanoparticles is characterized by decreasing emission intensity over time at a wavelength corresponding to the polymer hybrid nanoparticle emission. In certain embodiments, degradation of the polarization-sensitive nanoparticles is detected by increasing emission intensity over time at a particular wavelength corresponding to polymer emission. In addition to measuring polymer emission, the polarization-sensitive nanoparticles are designed to incorporate fluorescent dyes that are in solution during hybrid nanoparticle formation. As the polarization-sensitive nanoparticles degrade, the dye can leach out and are detected over time.

The majority of organic polymers used for chromophoric polarization-sensitive nanoparticles are insulators. When organic polymers have pi-conjugated structures, electrons can move along the polymer backbone through overlaps in pi-electron clouds by hopping, tunneling, and related mechanisms. In some aspects, these pi-conjugated polymers include wide-bandgap semiconductors, for example, semiconducting polymers.

In some aspects, the chromophoric polymer hybrid nanoparticle used comprises polymers bearing units of small organic dye molecules, metal complexes, photochotochromic dye, and any combinations thereof, for example, optically inactive polymers such as polystyrene covalently linked or grafted with small organic dye, metal complexes, photochromic dyes and any combination thereof. These dyes or metal complexes may have protein sensing capability.

A wide variety of polarization-sensitive nanoparticles are used, such as the examples described herein as well as others that are disclosed, e.g., in WO2011/057295 and WO2013/101902, each of which is incorporated by reference herein it its entirety and specifically with regard to the particular chromophoric polymer hybrid nanoparticle compositions and the respective methods of making them as described therein. As provided, e.g., in WO2011/057295, the polymers in the polarization-sensitive nanoparticles are physically blended or chemically bonded (or chemically crosslinked). For example, the physically blended polarization-sensitive nanoparticles can include polymers that are blended in the polymer hybrid nanoparticle and held together by non-covalent interactions. Chemically bonded polarization-sensitive nanoparticles can include polymers that are covalently attached to each other in the polymer hybrid nanoparticle. The chemically bonded polymers are covalently attached to each other prior to formation of the polarization-sensitive nanoparticles.

For example, the polarization-sensitive nanoparticles can include those that are directly functionalized and/or have low density functionalization.

In some aspects, the first matrix polymer and the second matrix polymer are the same. In other aspects, the first matrix polymer and the second matrix polymer are different.

Functionalized Polymers

In some aspects, chromophoric polarization-sensitive nanoparticles are used that contain a polymer functionalized on the terminal monomeric unit, for example with a carboxyl, amine, thiol, ester, succinimidyl ester, azide, alkyne, cyclooctyne, phosphine, or similar functional group. Examples of polymers that are used include, without limitation, poly(meth)acrylate polymers, polyacrylamide polymers, polyisobutylene, polydiene, polyphenylene, polyethylene, poly(ethylene glycol), polylactide, polystyrene, polysiloxane, poly(vinyl pyridine), poly(vinylpyrrolidone), polyurethane, a block copolymer thereof, a random or alternating copolymer thereof, and the like.

In some aspects, chromophoric polarization-sensitive nanoparticles are used that contain a copolymer having one or more functionalized monomeric units, for example an amphiphilic polymer, including but not limited to: poly((meth)acrylic acid)-based copolymers such as: poly(acrylic acid-b-acrylamide), poly(acrylic acid-b-methyl methacrylate), poly(acrylic acid-b-N-isopropylacrylamide), poly(n-butylacrylate-b-acrylic acid), poly(sodium acrylate-b-methyl methacrylate), poly(methacrylic acid-b-neopentyl methacrylate), poly(methyl methacrylate-b-acrylic acid), poly(methyl methacrylate-b-methacrylic acid), poly(methyl methacrylate-b-N,N-dimethyl acrylamide), poly(methyl methacrylate-b-sodium acrylate), poly(methyl methacrylate-b-sodium methacrylate), poly(neopentyl methacrylate-b-methacrylic acid), poly(t-butyl methacrylate-b-ethylene oxide), poly(2-acrylamido-2-methylpropanesulfonic acid-b-acrylic acid); polydiene-based copolymers such as: poly(butadiene(1,2 addition)-b-ethylene oxide), poly(butadiene (1,2 addition)-b-methylacrylic acid, poly(butadiene(1,4 addition)-b-acrylic acid), poly(butadiene(1,4 addition)-b-ethylene oxide, poly(butadiene(1,4 addition)-b-sodium acrylate), poly(butadiene(1,4 addition)-b-N-methyl 4-vinyl pyridinium iodide), poly(isoprene-b-ethylene oxide), poly(isoprene-b-ethylene oxide), and poly(isoprene-b-N-methyl 2-vinyl pyridinium iodide); poly(ethylene oxide)-based copolymers such as: poly(ethylene oxide-b-acrylic acid), poly(ethylene oxide-b-acrylamide), poly(ethylene oxide-b-butylene oxide), poly(ethylene oxide-b-c-caprolactone), poly(ethylene oxide-b-lactide), poly(ethylene oxide-b-lactide), poly(ethylene oxide-b-methacrylic acid), poly(ethylene oxide-b-methyl acrylate), poly(ethylene oxide-b-N-isopropylacrylamide), poly(ethylene oxide-b-methyl methacrylate), poly(ethylene oxide-b-nitrobenzyl methacrylate), poly(ethylene oxide-b-N,N-dimethylaminoethylmethacrylate), poly(ethylene oxide-b-propylene oxide), poly(ethylene oxide-b-t-butyl acrylate), poly(ethylene oxide-b-t-butyl methacrylate), poly(ethylene oxide-b-tetrahydrofurfuryl methacrylate), poly(ethylene oxide-b-2-ethyl oxazoline), poly(ethylene oxide-b-2-hydroxyethyl methacrylate), poly(ethylene oxide-b-2-methyl oxazoline); polyisobutylene-based copolymers such as poly(isobutylene-b-acrylic acid), poly(isobutylene-b-ethylene oxide), poly(isobutylene-b-methacrylic acid); polystyrene based copolymers such as poly(styrene-b-acrylamide), poly(styrene-b-acrylic acid), poly(styrene-b-cesium acrylate), poly(styrene-b-ethylene oxide), poly(styrene-b-ethylene oxide) acid cleavable at the block junction, poly(styrene-b-methacrylic acid), poly(-styrenesulfonic acid-b-ethylene oxide), poly(styrenesulfonic acid-b-methylbutylene), poly(styrene-b-N,N-dimethylacrylamide), poly(styrene-b-N-isopropyl acrylamide), poly(styrene-b-N-methyl 2-vinyl pyridinium iodide), poly(styrene-b-N-methyl-4-vinyl pyridinium iodide), poly(styrene-b-propylacrylic acid), poly(styrene-b-sodium acrylate)poly(styrene-b-sodium methacrylate), polyp-chloromethyl styrene-b-acrylamide), poly(styrene-co-p-chloromethyl styrene-b-acrylamide), poly(styrene-co-p-chloromethyl styrene-b-acrylic acid), poly(styrene-b-methylbutylene-co-isoprene sulfonate); polysiloxane-based copolymers such as poly(dimethylsiloxane-b-acrylic acid), poly(dimethylsiloxane-b-ethylene oxide), poly(dimethylsiloxane-b-methacrylic acid); poly(ferrocenyldimethylsilane) based copolymers such as poly(ferrocenyldimethylsilane-b-ethylene oxide); poly(-vinyl naphthalene)-based copolymers such as poly(-vinyl naphthalene-b-acrylic acid), poly (vinyl pyridine and N-methyl vinyl pyridinium iodide)-based copolymers such as poly(-vinyl pyridine-b-ethylene oxide), poly(-vinyl pyridine-b-methyl acrylic acid), poly(N-methyl 2-vinyl pyridinium iodide-b-ethylene oxide), poly(N-methyl 4-vinyl pyridinium iodide-b-methyl methacrylate), poly(-vinyl pyridine-b-ethylene oxide) PEO end functional OH; and poly(vinyl pyrrolidone)-based copolymers such as poly(vinyl pyrrolidone-b-D/L-lactide); and the like.

Functionalized Hybrid Nanoparticles

The present disclosure describes compositions of, methods of making and methods of using nanoparticles comprising more than one polymer and as such, are hybrid nanoparticles. In some aspects, hybrid nanoparticles comprise a semiconducting polymer and at least one type of non-semiconducting polymer which includes a functionalized non-semiconducting polymer and/or a matrix non-semiconducting polymer.

In some aspects, the first matrix polymer comprises a first functional group capable of conjugation. In certain aspects, the first functional group is selected from an aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, or a combination thereof. In certain aspects, the first functional group is a carboxyl.

In some aspects, the second matrix polymer comprises a second functional group capable of conjugation. In certain aspects, the second functional group is selected from an aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, or a combination thereof. In certain aspects, the second functional group is a carboxyl.

In some aspects, the chromophoric polymer is conjugated at the first functional group, the second functional group, or a combination thereof. In further aspects, the polarization-sensitive nanoparticle is conjugated to a binding moiety and wherein the binding moiety is configured to bind to a target. In certain aspects, the target is a biomolecule. In further aspects, the target is a biomarker. In further aspects, the target is selected from an antibody, an antigen, a cell, a nucleic acid, an enzyme, a substrate for an enzyme, a protein, a lipid, a carbohydrate, or a combination thereof.

In certain aspects, the first functional group, the second functional group, or a combination thereof are suitable for bioconjugation. In further aspects, the polarization-sensitive nanoparticle is bioconjugated to streptavidin. In other aspects, the polarization-sensitive nanoparticle is bioconjugated to a protein, an antibody, a nucleic acid molecule, a lipid, a peptide, an aptamer, a drug, or a combination thereof. In further aspects, the polarization-sensitive nanoparticle is conjugated to polyethylene glycol.

In other aspects, the polarization-sensitive nanoparticles comprise a functional group, wherein the functional group inhibits the polarization-sensitive nanoparticle from aggregating with other polarization-sensitive nanoparticles. In other aspects, the functional group inhibits non-specific adsorption at the polarization-sensitive nanoparticle.

Advantages can in various aspects arise from using polarization-sensitive nanoparticles that include a single polymer molecule having at least one functional group at a terminal unit. For example, the attachment of only one functional group to a terminal unit of a chromophoric polymer is well controlled in polymer synthesis. For example, a chemical unit comprising a functional group can serve as a polymerization initiator as well as a growth catalyst in polymer synthesis, and in this way each polymer molecule includes just one functional group at the terminus. Attachment of functional groups only to the two terminal units of a linear chromophoric polymer is well controlled in polymer synthesis. For example, a chemical unit comprising a functional group is used as a capping agent to terminate the polymer growth in polymer synthesis, thereby resulting in each linear polymer molecule including only two functional groups in the two terminal units. Similarly, the attachment of functional groups for multivalent polarization-sensitive nanoparticles is well controlled in polymer synthesis, e.g., functional groups can only be added to the three terminal units of a three-arm branched polymer. Any polymer, for example a semiconducting or a non-semiconducting polymer, are functionalized as described herein.

In various embodiments, the present disclosure provides for the use of "functionalized" polarization-sensitive nanoparticles, and particularly as a means for modifying a surface of the chromophoric polymer hybrid nanoparticle. As used herein, the term "functionalized" in the context of chromophoric polarization-sensitive nanoparticles refers to chromophoric polarization-sensitive nanoparticles that are linked (e.g., covalently bonded) to one or more functional groups. As used herein, the term "functional group" refers to any chemical unit that are attached, such as by any stable physical or chemical association, to the chromophoric polymer, thereby altering the surface of the chromophoric polymer hybrid nanoparticle, e.g., rendering the surface available for conjugation (e.g., bioconjugation). The functional group can be covalently linked to a backbone, side chain, or one of the terminating units of the chromophoric polymer. The functional group are, without limitation, any the following: an aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, or a combination thereof. In general, any other functional groups that are suitable for bioconjugation are used. Such functional groups could be found by one of ordinary skill in the art, for example in Bioconjugate Techniques (Academic Press, New York, 1996 or later versions), which is herein incorporated by reference in its entirety for all purposes.

In some aspects, functional groups of the present disclosure are selected from aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, or a combination thereof.

In various embodiments, the polymer hybrid nanoparticle comprises a functional group attached to the polymer hybrid nanoparticle. In certain embodiments, the functional group is selected from a hydrophobic functional group, a hydrophilic functional group, or a combination thereof. In some aspects, the functional group is suitable for bioconjugation.

In certain embodiments, the functional group is selected from aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, or a combination thereof.

The present disclosure also provides, in one case, a chromophoric polymer hybrid nanoparticle and only one functional group. The chromophoric polymer hybrid nanoparticle contains at least one chromophoric polymer. The "monovalent" as that term is used herein refers to just one functional group that is attached to the chromophoric polarization-sensitive nanoparticles. The functional group are attached to the chromophoric polymer hybrid nanoparticle by any stable physical association or chemical bonding, and provides only one reactive site on the surface of chromophoric polymer hybrid nanoparticle for bioconjugation.

The present disclosure provides, in another case, a chromophoric polymer hybrid nanoparticle and only two functional groups. The chromophoric polymer hybrid nanoparticle contains at least one chromophoric polymer. The "bivalent" as that term is used herein refers to just two functional groups that are attached to each chromophoric polymer hybrid nanoparticle. The functional groups are attached to the chromophoric polymer hybrid nanoparticle by any stable physical association or chemical bonding, and provides only two reactive sites on the surface of chromophoric polymer hybrid nanoparticle for bioconjugation. The two reactive sites can have different reactivity (e.g., via two different types of function groups) or same reactivity.

In some aspects, the chromophoric polarization-sensitive nanoparticles can include at least one semiconducting polymer. In certain embodiments, the chromophoric polarization-sensitive nanoparticles can include luminescent semiconducting polymer with delocalized pi-electrons. The term "semiconducting polymer" is recognized in the art. Typical luminescent semiconducting polymers include, but are not limited to fluorene polymers, phenylene vinylene polymers, phenylene polymers, benzothiazole polymers, thiophene polymers, carbazole fluorene polymers, boron-dipyrromethene polymer and related copolymers. In certain embodiments, the semiconducting polymers of the present disclosure include polymers that do not have triple bonds present along the polymer backbone. In some aspects, the chromophoric polarization-sensitive nanoparticles can include a single molecule semiconducting polymer. In certain embodiments, the chromophoric polarization-sensitive nanoparticles can include several molecules of a semiconducting polymer wherein the molecules of the semiconducting polymer are the same or are different. The several molecules can, e.g., be the same type of semiconducting polymer or a blend of different polymers (e.g., semiconducting polymers and/or non-semiconducting polymers). The present disclosure provides, in one case, functionalized chromophoric polymers, where the hydrophilic functional groups are introduced into the side chains of the polymer at a sufficiently low density where the functional groups do not adversely affect the collapse of the polymer chain into a hybrid nanoparticle form, and/or do not adversely affect the stability and performance of the formed chromophoric polarization-sensitive nanoparticles, and/or do not adversely loosen the compact internal structure, and/or do not adversely reduce fluorescence brightness, and/or do not adversely increase nonspecific labeling. As provided herein, the degree of hydrophilicity of the functional groups can affect what constitutes a sufficiently low density that gives desired characteristics for the polarization-sensitive nanoparticles. In some aspects, the density of the functional groups on the side chains is less than about 50%. In some aspects, the density of the functional groups on the side chains is less than about 40%. In some aspects, the density of the functional groups on the side chains is less than about 30%. In some aspects, the density of the functional groups on the side chains is less than about 25%. In another case, the density of the functional groups on the side chains is less than about 20%. In another case, the density of the functional groups on the side chains is less than about 15%. In another case, the density of the functional groups on the side chains is less than about 10%. In yet another case, the density of the functional groups on the side chains is less than about 5%. In certain embodiments, the density of the functional groups on the side chains is less than about 25%, or less than about 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or less. In certain example embodiments, after hybrid nanoparticle formation (post-functionalization), the density of the functional groups on the surface of a chromophoric hybrid nanoparticle are increased by surface modifications because the hybrid nanoparticles are already formed and the hydrophilic moieties do not adversely affect the formation, stability, internal structure, and fluorescence brightness of the polarization-sensitive nanoparticles. Moreover, the hydrophilic moieties can provide certain properties such as reducing nonspecific interactions by PEG groups, and/or generating high surface zeta potential by highly charged species and/or creating zwitterionic surfaces by zwitterionic moieties.

The present disclosure provides, in another case, functionalized chromophoric polymers, where hydrophilic functional groups are introduced into only the terminal groups of the main chain of the polymer where the functional groups do not adversely affect the collapse of the polymer chain into a hybrid nanoparticle form, and/or do not adversely affect the stability of the formed chromophoric polarization-sensitive nanoparticles, and/or do not adversely loosen the compact internal structure, and/or do not adversely reduce fluorescence brightness, and/or do not adversely increase nonspecific labeling. In yet another case, the hydrophilic functional groups are introduced into both the terminal groups of the main chain of the polymer and also the side chains of the polymer but at a sufficiently low density where the functional groups do not adversely affect the collapse of the polymer chain into a hybrid nanoparticle form, or do not adversely affect the stability of the formed chromophoric polarization-sensitive nanoparticles, or do not adversely loosen the compact internal structure, or do not adversely reduce fluorescence brightness, or do not adversely increase nonspecific labeling. The degree of hydrophilicity of the functional groups can affect what constitutes a sufficiently low density that gives desired characteristics for the polarization-sensitive nanoparticles. In certain example embodiments, after the hybrid nanoparticle formation (post-functionalization), the density of the hydrophilic moieties on the surface of a chromophoric hybrid nanoparticle are increased by surface modifications because the hybrid nanoparticles are already formed and the hydrophilic moieties do not adversely affect the formation, stability, internal structure, and fluorescence brightness of the polarization-sensitive nanoparticles, but can provide certain properties such as reducing nonspecific interactions by PEG groups, and/or generating high surface zeta potential by highly charged species and/or creating zwitterionic surfaces by zwitterionic moieties.

In some aspects, this disclosure provides functionalized chromophoric polymers that include hydrophobic functional groups. The hydrophobic functional groups include but not limit to those used for click chemistry, such as alkyne, strained alkyne, azide, diene, alkene, cyclooctyne, and phosphine groups. The density of the hydrophobic functional groups are varied from 0% to 100%. In certain embodiments, the density of the hydrophobic functional groups are about 100%, less than about 100%, less than about 90%, less than about 80%, less than about 70%, less than about 60%, less than about 50%, less than about 40%, less than about 30%, less than about 20%, less than about 10%, less than about 5%, less than about 1%, or lower. In some aspects, the density of functionalizing with hydrophobic functional groups does not adversely affect the collapse of the polymer chain into a hybrid nanoparticle form, and/or does not adversely affect the stability of the formed chromophoric polarization-sensitive nanoparticles, and/or does not adversely loosen the compact internal structure, and/or does not adversely reduce fluorescence brightness, and/or does not adversely increase nonspecific labeling. In certain embodiments, the hydrophobic functional groups are directly linked to biologically relevant molecules described further herein (e.g., antibodies) or be converted to hydrophilic functional groups that can link to biologically relevant molecules or be converted to other hydrophilic moieties for certain properties after the formation of a chromophoric polymer hybrid nanoparticle.

In another case, the functionalized chromophoric polymers can include hydrophobic chromophoric polymers, physically mixed or chemically cross-linked with another one or more chromophoric polymers with hydrophilic functional groups. The hydrophobic chromophoric polymers may not include a hydrophilic functional group, but may have hydrophobic functional groups (e.g., those used for click chemistry, including but not limited to alkyne, strained alkyne, azide, diene, alkene, cyclooctyne, and phosphine groups). In certain embodiments, the surface of the chromophoric polarization-sensitive nanoparticles are functionalized by one or more chromophoric polymers comprising hydrophilic functional groups, which are introduced into either the terminal groups of the main chain of the polymer or the side chains of the polymer. In these embodiments, the density of the functionalization in the functionalized chromophoric polymer are varied from 0% to 100%, but the blending ratio of the functionalized chromophoric polymers to the hydrophobic polymers should be sufficiently low so that the functionalization does not adversely affect the collapse of the polymer chain into a hybrid nanoparticle form, and/or does not adversely affect the stability of the formed chromophoric polarization-sensitive nanoparticles, and/or does not adversely loosen the compact internal structure, and/or does not adversely reduce fluorescence brightness, and/or does not adversely increase nonspecific labeling.

In some aspects, the functionalized chromophoric polymers comprise one or more functionalized chromophoric polymers that are chemically cross-linked with each other prior to particle formation and also comprise surface functional groups for bioconjugation. In this case, the functional groups are introduced into either the terminal groups of the main chain of the polymer or the side chains of the polymer. The density of the functionalization in the functionalized chromophoric polymers are varied from 0% to 100% to form chromophoric polarization-sensitive nanoparticles with chemically cross-linked structure, where the chemical cross-linking, even at high density of functionalization, can assist the collapse of the polymer chain into a hybrid nanoparticle form, form compact internal structure, keep good stability and fluorescence brightness of the formed chromophoric polarization-sensitive nanoparticles.

Electrons, holes, or electronic energy, are conducted along the conjugated structure of the conjugated polymer. In some aspects, a large portion of the polymer backbone is conjugated. In some aspects, the entire polymer backbone are conjugated. In some aspects, the polymer can include conjugated structures in their side chains or termini. In some aspects, the conjugated polymer can have conducting properties, e.g., the polymer can conduct electricity. In some aspects, the conjugated polymer can have semiconducting properties, e.g., the polymers can exhibit a direct band gap, leading to an efficient absorption or emission at the band edge. In some aspects, the chromophoric polarization-sensitive nanoparticles are described as hybrid nanoparticles including at least one condensed (or collapsed) conjugated polymer (e.g., semiconducting polymer) to form the hybrid nanoparticle structure.

A polymer, or a hybrid nanoparticle comprising the polymer, is conjugated to another moiety with properties useful for therapy, diagnosis, imaging, or research. For example, a polymer or a hybrid nanoparticle is conjugated to an additional moiety through a linker. The linker is hydrophilic or hydrophobic. Non-limiting examples of linkers include a chemical bond, a small molecule, such as an amino acid, a functional group, such as an ester, and amide, a carbamate, an ether, an alkylene group, an alkenylene group, and alkynylene group, or an arylene group, or a polymer, such as a polyether, a polyester, a polyamide, a polycarbamate, a polyaryl, a polystyrene, or a polyolefin. In some aspects, the linker is polyethylene glycol or polystyrene polyethylene glycol.

In some aspects, the polymer is conjugated to a hydrophilic moiety, for example, a hydrophilic functional group. Non-limiting examples of hydrophilic functional groups include carboxyl groups, hydroxyl groups, amino groups, amido groups, sulfhydryl groups, sulfate groups phosphate groups, and any hydrogen bond donor or acceptor.

The polymer are conjugated to a reactive moiety, for example, an acid anhydride, an acid halide, a nucleophile, an electrophile, an electron donor, an electron acceptor, an olefin, an alkyne, an acidic group, a basic group, an oxidizing group, a reducing group, an electron transfer agent, or a photochemically-reactive species. Non-limiting examples of acid anhydrides include maleic anhydride and succinic anhydride, either of which being substituted or unsubstituted.

In some aspects, methods, compositions and kits are provided for the use of chromophoric polarization-sensitive nanoparticles that have been functionalized. According to the present disclosure, chromophoric polarization-sensitive nanoparticles are functionalized in any manner that renders them suitable for further modification, e.g., bioconjugation, or for subsequent use in the detection of proteins or peptides. For example, a functional group are linked (e.g., covalently bonded) to the backbone, the side chain, or one of the terminal units of a chromophoric polymer. In some aspects, a monovalent polymer hybrid nanoparticle can include a single polymer molecule that includes only one functional group, e.g., at one of two terminal units of the single linear polymer molecule. A bivalent polymer hybrid nanoparticle can include a single polymer molecule that includes two functional groups, e.g., at each of the two terminal units of the single linear polymer molecule. A trivalent polymer hybrid nanoparticle can include a single polymer molecule that includes three functional groups, e.g., attachment of functional groups only to the three terminal units of a three-arm branched polymer. Similarly, branched polymer are used in preparing other multivalent polarization-sensitive nanoparticles, e.g., that have functional groups attached at the terminal units of four-arm, five-arm, six-arm, and branched polymers with higher numbers of branches.

Monovalent, Bivalent, or Multivalent Functionalized Polymers and Hybrid Nanoparticles Functional groups described herein are included in the chromophoric polymers in a variety of ways. For example, a functional group are linked (e.g., covalently bonded) to the backbone, the side chain, or one of the terminal units of a chromophoric polymer. As described further herein, a monovalent polymer hybrid nanoparticle can include a single polymer molecule that includes only one functional group, e.g., at one of two terminal units of the single linear polymer molecule. A bivalent polymer hybrid nanoparticle can include a single polymer molecule that includes two functional groups, e.g., at each of the two terminal units of the single linear polymer molecule. A trivalent polymer hybrid nanoparticle can include a single polymer molecule that includes three functional groups, e.g., attachment of functional groups only to the three terminal units of a three-arm branched polymer. Similarly, branched polymer are used in preparing other multivalent polarization-sensitive nanoparticles, e.g., that have functional groups attached at the terminal units of four-arm, five-arm, six-arm, and branched polymers with higher numbers of branches.

In some aspects, advantages can arise from polarization-sensitive nanoparticles that include a single polymer molecule having at least one functional group at a terminal unit. In some aspects, advantages can arise from polarization-sensitive nanoparticles that include more than one polymer molecule having at least one functional group at a terminal unit. For example, the attachment of only one functional group to a terminal unit of a chromophoric polymer is well controlled in polymer synthesis. For example, a chemical unit comprising a functional group can serve as a polymerization initiator as well as a growth catalyst in polymer synthesis, and in this way each polymer molecule includes just one functional group at the terminus. Attachment of functional groups only to the two terminal units of a linear chromophoric polymer is well controlled in polymer synthesis. For example, a chemical unit comprising a functional group is used as a capping agent to terminate the polymer growth in polymer synthesis, thereby resulting in each linear polymer molecule including only two functional group in the two terminal units. Similarly, the attachment of functional groups for multivalent polarization-sensitive nanoparticles is well controlled in polymer synthesis, e.g., functional groups can only be added to the three terminal units of a three-arm branched polymer.

In certain embodiments, addition of functional groups to polymer terminal units is compared to polymers, in which the functional groups are randomly positioned along the backbone. For example, the number of functional groups in a polymer by side-chain functionalization or backbone functionalization is difficult to produce polymers having a precise number of functional groups. Instead, the number of functional groups on the polymers usually follows a distribution. In certain embodiments, the functional group in the terminal units is also advantageous to the side chains in other embodiments. As compared to side-chain and backbone functionalization, functionalization of the terminal units does not have as much affect on the collapse of the polymer to form polarization-sensitive nanoparticles. Also, the terminal functional groups are more accessible to an aqueous environment for bioconjugation, whereas the side-chain functional groups are embedded inside the polymer hybrid nanoparticle and unavailable for bioconjugation.

In one case, the chromophoric polymer hybrid nanoparticle comprises only one chromophoric polymer molecule that is linked with one functional group (e.g., R). Such a chromophoric polymer hybrid nanoparticle is a monovalent single-molecule hybrid nanoparticle that may provide unique properties such as monodispersed size, and uniform fluorescence brightness. The functional group can be covalently linked to backbone, side chain, or one of the terminating units of the chromophoric polymer. The functional group are any of the groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof. In general, any other functional groups that are suitable for bioconjugation are used. Such functional groups could be found by one of ordinary skill in the art, for example in Bioconjugate Techniques (Academic Press, New York, 1996 or later versions), the content of which is herein incorporated by reference in its entirety for all purposes. Chromophoric polymer comprising one functional group can be synthesized by many approaches. For example, a chemical unit comprising a functional group can serve as a polymerization initiator as well as a growth catalyst in polymer synthesis, and in this way each polymer molecule is finally terminated by just one functional group.

In another case, the chromophoric polymer hybrid nanoparticle comprises more than one chromophoric polymer molecule that is linked with one functional group (e.g., R). Such a chromophoric polymer hybrid nanoparticle is a monovalent single-molecule hybrid nanoparticle that may provide unique properties such as monodispersed size, and uniform fluorescence brightness. The functional group is covalently linked to backbone, side chain, or one of the terminating units of the chromophoric polymer. The functional group can be any of the groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof. In general, any other functional groups that are suitable for bioconjugation are used. Such functional groups could be found by one of ordinary skill in the art, for example in Bioconjugate Techniques (Academic Press, New York, 1996 or later versions), the content of which is herein incorporated by reference in its entirety for all purposes. Chromophoric polymer comprising one functional group is synthesized by many approaches. For example, a chemical unit comprising a functional group can serve as a polymerization initiator as well as a growth catalyst in polymer synthesis, and in this way each polymer molecule is finally terminated by just one functional group.

In some aspects, the chromophoric polarization-sensitive nanoparticles can include one polymer molecule with two functional groups (e.g., $R^1$ and $R^2$). Such a chromophoric polymer hybrid nanoparticle is bivalent single-molecule hybrid nanoparticle that may provide unique properties such as monodispersed size, and uniform fluorescence brightness, and conjugation to two different types of biomolecules. The two functional groups are covalently linked to the backbone, side chains, and/or the terminating units of the chromophoric polymer. In certain aspects, the chromophoric polymer hybrid nanoparticle comprises one linear polymer molecule with two terminating functional groups. Such a chromophoric polymer hybrid nanoparticle is a bivalent single-molecule hybrid nanoparticle that is, e.g., useful in certain applications such as for forming polarized fluorescent bioconjugates, or assembling the hybrid nanoparticles into one-dimensional structures. The two functional groups $R^1$ and $R^2$ are the same, or they are different. The functional groups are any of the groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and any combination thereof. In general, any other functional groups that allow bioconjugation are used. Such functional groups could be found by one of ordinary skill in the art, for example in Bioconjugate Techniques (Academic Press, New York, 1996 or later versions) the content of which is herein incorporated by reference in its entirety for all purposes.

In some aspects, the chromophoric polarization-sensitive nanoparticles can include more than one polymer molecule with two functional groups (e.g., $R^1$ and $R^2$). Such a chromophoric polymer hybrid nanoparticle is bivalent single-molecule hybrid nanoparticle that may provide unique properties such as monodispersed size, and uniform fluorescence brightness, and conjugation to two different types of biomolecules. The two functional groups are covalently linked to the backbone, side chains, and/or the terminating units of the chromophoric polymer. In certain aspects, the chromophoric polymer hybrid nanoparticle comprises one linear polymer molecule with two terminating functional groups. Such a chromophoric polymer hybrid nanoparticle is a bivalent single-molecule hybrid nanoparticle that is, e.g., useful in certain applications such as for forming polarized fluorescent bioconjugates, or assembling the hybrid nanoparticles into one-dimensional structures. The two functional groups $R^1$ and $R^2$ are the same, or they are different. The functional groups are any of the groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and any combination thereof. In general, any other functional groups that allow bioconjugation are used. Such functional groups could be found by one of ordinary skill in the art, for example in Bioconjugate Techniques (Academic Press, New York, 1996 or later versions) the content of which is herein incorporated by reference in its entirety for all purposes.

In another case, the chromophoric polymer hybrid nanoparticle comprises one polymer molecule with three hydrophilic functional groups (e.g., $R^1$, $R^2$, and $R^3$). Such a chromophoric polymer hybrid nanoparticle is trivalent single-molecule hybrid nanoparticle that may provide unique properties such as monodispersed size, and uniform fluorescence brightness. The three functional groups are covalently linked to the backbone, side chains, and/or the terminating units of the chromophoric polymer. The three functional groups (e.g., $R^1$, $R^2$, and $R^3$) are the same, or they are different. The functional groups are any of the groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and any combination thereof. In general, any other functional groups that allow bioconjugation are used. Such functional groups could be found by one of ordinary skill in the art, for example in Bioconjugate Techniques (Academic Press, New York, 1996 or later versions) the content of which is herein incorporated by reference in its entirety for all purposes. Such a single-molecule hybrid nanoparticle is trivalent, but has well-controlled functional groups (determined by the number of backbone branches) that are useful for certain applications such as polarized fluorescent bioconjugates, or directed hybrid nanoparticle assembly.

In another case, the chromophoric polymer hybrid nanoparticle comprises more than one polymer molecule with three hydrophilic functional groups (e.g., $R^1$, $R^2$, and $R^3$). Such a chromophoric polymer hybrid nanoparticle is trivalent single-molecule hybrid nanoparticle that may provide unique properties such as monodispersed size, and uniform fluorescence brightness. The three functional groups are covalently linked to the backbone, side chains, and/or the terminating units of the chromophoric polymer. The three functional groups (e.g., $R^1$, $R^2$, and $R^3$) are the same, or they are different. The functional groups are any of the groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and any combination thereof. In general, any other functional groups that allow bioconjugation are used. Such functional groups could be found by one of ordinary skill in the art, for example in Bioconjugate Techniques (Academic Press, New York, 1996 or later versions) the content of which is herein incorporated by reference in its entirety for all purposes. Such a single-molecule hybrid nanoparticle is trivalent, but has well-controlled functional groups (determined by the number of backbone branches) that are useful for certain applications such as polarized fluorescent bioconjugates, or directed hybrid nanoparticle assembly.

In some aspects, the chromophoric polarization-sensitive nanoparticles can include one polymer molecule with four functional groups, or five functional groups, or six functional groups, or more functional groups. Such a chromophoric polymer hybrid nanoparticle is multivalent single-molecule hybrid nanoparticle that can provide unique properties such as monodispersed size, uniform fluorescence brightness, or bioconjugation capability. The functional groups are covalently linked to the backbone, side chains, and/or the terminating units of the chromophoric polymer. In certain aspects, the chromophoric polymer hybrid nanoparticle comprises single molecule of four-arm branched polymer, five-arm branched polymer, six-arm branched polymer etc. where each arm contains one functional group. The functional groups are any of the groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and any combination thereof. In general, any other functional groups that are suitable for bioconjugation are used. Such functional groups could be found by one of ordinary skill in the art, for example in Bioconjugate Techniques (Academic Press, New York, 1996 or later versions) the content of which is herein incorporated by reference in its entirety for all purposes. The functional groups are the same, or they are different. Such a single-molecule hybrid nanoparticle is multivalent, but has well-controlled functional groups (pre-defined by the number of backbone branches) that are useful for certain applications such as polarized fluorescent bioconjugates, or directed hybrid nanoparticle assembly, or bioconjugation.

In some aspects, the chromophoric polarization-sensitive nanoparticles can include more than one polymer molecule with four functional groups, or five functional groups, or six functional groups, or more functional groups. Such a chromophoric polymer hybrid nanoparticle is multivalent single-molecule hybrid nanoparticle that can provide unique properties such as monodispersed size, uniform fluorescence brightness, or bioconjugation capability. The functional groups are covalently linked to the backbone, side chains, and/or the terminating units of the chromophoric polymer. In certain aspects, the chromophoric polymer hybrid nanoparticle comprises single molecule of four-arm branched polymer, five-arm branched polymer, six-arm branched polymer etc. where each arm contains one functional group. The functional groups are any of the groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and any combination thereof. In general, any other functional groups that are suitable for bioconjugation are used. Such functional groups could be found by one of ordinary skill in the art, for example in Bioconjugate Techniques (Academic Press, New York, 1996 or later versions) the content of which is herein incorporated by reference in its entirety for all purposes. The functional groups are the same, or they are different. Such a single-molecule hybrid nanoparticle is multivalent, but has well-controlled functional groups (pre-defined by the number of backbone branches) that are useful for certain applications such as polarized fluorescent bioconjugates, or directed hybrid nanoparticle assembly, or bioconjugation.

In some aspects, the chromophoric polarization-sensitive nanoparticles can include a functionalized multi-molecule chromophoric polymer hybrid nanoparticle that is modified to form a monovalent hybrid nanoparticle. Functionalized chromophoric hybrid nanoparticle is prepared by using chromophoric polymer molecules bearing functional groups (such as PDHF-COOH). The functional groups are covalently linked to the backbone, side chain, and/or the terminating unit of the chromophoric polymer. Alternatively, the chromophoric polymer hybrid nanoparticle is functionalized through a functionalization agent. Functionalization agents and method are known, for example, see, U.S. Provisional Patent Application Ser. No. 61/259,611, the contents of which are herein incorporated by reference in their entirety for all purposes. The functional group are any of the groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and any combination thereof. In general, any other functional groups that are suitable for bioconjugation are used. Such functional groups could be found by one of ordinary skill in the art, for example in Bioconjugate Techniques (Academic Press, New York, 1996 or later versions) the content of which is herein incorporated by reference in its entirety for all purposes.

Bioconjugates of Hybrid Nanoparticles

In some aspects, the present disclosure provides a bioconjugate that can include a functionalized chromophoric polymer hybrid nanoparticle as described above and a biomolecule, wherein the biomolecule is attached to the polymer hybrid nanoparticle either directly or indirectly by the functional groups. The bioconjugates can also include functionalized chromophoric polarization-sensitive nanoparticles as described above, associated with biological particle such as virus, bacteria, cells, biological or synthetic vesicles such as liposomes. The functionalized chromophoric polarization-sensitive nanoparticles can include one or more functional groups that are formed from the chromophoric polymer with one or two terminating functional groups, or low density side-chain functional groups.

In certain embodiments, the present disclosure provides a bioconjugate comprising a monovalent chromophoric polymer hybrid nanoparticle as described above and a biomolecule, wherein the biomolecule is attached to the polymer hybrid nanoparticle either directly or indirectly by the functional group. The bioconjugates also comprise monovalent chromophoric polymer hybrid nanoparticle as described above, associated with biological particle such as virus, bacteria, cells, biological or synthetic vesicles such as liposomes. The term "biomolecule" is used to describe a synthetic or naturally occurring protein, glycoprotein, peptide, amino acid, metabolite, drug, toxin, nuclear acid, nucleotide, carbohydrate, sugar, lipid, fatty acid and the like. Desirably, the biomolecule is attached to the functional group of monovalent chromophoric polymer hybrid nanoparticle via a covalent bond. For example, if the functional group of the polymer hybrid nanoparticle is a carboxyl group, a protein biomolecule are directly attached to the polymer hybrid nanoparticle by cross-linking the carboxyl group with an amine group of the protein molecule.

As used herein, the term "cross-linking agent" is used to describe a compound or moiety that is capable of forming a chemical bond between molecular groups on similar or dissimilar molecules so as to covalently bond together the molecules. Examples of common cross-linking agents are known in the art. See, for example, Bioconjugate Techniques (Academic Press, New York, 1996 or later versions) the content of which is herein incorporated by reference in its entirety for all purposes. Indirect attachment of the biomolecule to monovalent chromophoric polarization-sensitive nanoparticles can occur through the use of "linker" molecule, for example, avidin, streptavidin, neutravidin, biotin or a like molecule.

In various embodiments, the polarization-sensitive nanoparticles of the present disclosure are bioconjugated to facilitate the detection of proteins or peptides. In some aspects, methods, compositions and kits are provided for the use of chromophoric polarization-sensitive nanoparticles conjugated to biomolecules, such as for example, functionalization of chromophoric polarization-sensitive nanoparticles wherein the biomolecule is attached to the chromophoric polymer hybrid nanoparticle either directly or indirectly by functional groups.

The term "biomolecule" is used to describe a synthetic or naturally occurring protein, glycoprotein, peptide, amino acid, metabolite, drug, toxin, nuclear acid, nucleotide, carbohydrate, sugar, lipid, fatty acid and the like. Chromophoric polarization-sensitive nanoparticles conjugated to biomolecules are sometimes referred to herein as "bioconjugates." Bioconjugates can also include functionalized chromophoric polarization-sensitive nanoparticles associated with biological particles such as viruses, bacteria, cells, and naturally occurring or synthetic vesicles such as liposomes. The functionalized chromophoric polarization-sensitive nanoparticles can include one or more functional groups that are formed from the chromophoric polymer with one or two terminating functional groups, or low density side-chain functional groups.

In certain embodiments, the bioconjugates comprise a monovalent chromophoric polymer hybrid nanoparticle and a biomolecule, wherein the biomolecule is attached to the polymer hybrid nanoparticle either directly or indirectly by a functional group. The bioconjugates can also comprise monovalent chromophoric polarization-sensitive nanoparticles associated with biological particles such as viruses, bacteria, cells, and naturally occurring or synthetic vesicles such as liposomes.

In some aspects of the present disclosure, the biomolecule is attached to the functional group of a monovalent chromophoric polymer hybrid nanoparticle via a covalent bond. For example, if the functional group of the polymer hybrid nanoparticle is a carboxyl group, a protein biomolecule are directly attached to the polymer hybrid nanoparticle by cross-linking the carboxyl group with an amine group of the protein molecule.

In some aspects, the polymers are conjugated to a biomolecule, for example, a peptide, protein, an aptamer, an antibody, an enzyme, carbohydrate, nucleic acid, deoxyribonucleic acid, ribonucleic acid, or lipid. In some aspects, a chromophoric polymer hybrid nanoparticle is conjugated to a small molecule, a drug, a biomimetic, a pharmaceutical compound, an isotope, a radioisotope, or a chemical. In some aspects, a polymer or hybrid nanoparticle is conjugated to streptavidin. In some aspects, a polymer or hybrid nanoparticle is conjugated to polyethylene glycol (PEG). In some aspects, a polymer or hybrid nanoparticle is conjugated to biotin, or indirectly linked to biotin through streptavidin. In some aspects, a polymer or hybrid nanoparticle is conjugated to a tag such as hemagglutanin (HA), vesicular stomatitis virus (VSV), glutathione S-transferase (GST), histadine, more than one histadine, six histadines (6×His) or c-myc.

In some aspects, methods, compositions and kits are provided for analysis of a target molecule (e.g., a protein) using polarization-sensitive nanoparticles conjugated to biomolecules that specifically bind to the target.

In some aspects, fluorescent chromophoric polarization-sensitive nanoparticles are conjugated to one or more molecules that provide a function or other benefit, including without limitation, binding affinity for a target molecule.

In some aspects, the target molecule is a protein of interest, and the biomolecule conjugated to a chromophoric polymer hybrid nanoparticle is a primary antibody that specifically binds to the target protein.

In other embodiments, the target molecule is a protein of interest bound to a primary antibody for said protein, and the biomolecule conjugated to a chromophoric polymer hybrid nanoparticle is a secondary antibody that specifically binds to the primary antibody.

As used herein, the term "biotin" refers to any one of a variety of biotin derivatives and analogs that are effective in avidin binding. Suitable biotin moieties include those moieties that enable the biotinylated peptide fragment to be isolated by avidin and related avidin proteins. Representative biotin moieties include biotin derivatives such as iminobiotin, biocytin, and caproylamidobiotin, and biotin analogs such as desthiobiotin and biotin sulfone.

As used herein, the term "avidin" refers to any biotin-binding protein other than an immunoglobulin that binds biotin including both natural proteins and recombinant and genetically engineered proteins. The term includes the two common biotin-binding proteins known as "egg white" or "avian" avidin and "streptavidin." Egg white or avian avidin, commonly referred to simply as avidin, is a protein that is a constituent of egg white and forms a noncovalent complex with biotin. Streptavidin is an avidin protein isolated from the actinobacterium *Streptomyces avidinii* and also forms a noncovalent complex with biotin. Other bacterial sources of biotin binding proteins are also known. Both egg white avidin and streptavidin are tetrameric proteins in which the biotin binding sites are arranged in pairs on opposite faces of the avidin molecule. The term also refers to avidin derivatives including succinyl avidin, ferritin avidin, enzyme avidin, and crosslinked avidin.

In some aspects, fluorescent chromophoric polarization-sensitive nanoparticles are conjugated to one or more molecules that alter other properties of the chromophoric polarization-sensitive nanoparticles, such as their size, fluorescence, hydrophobicity, non-specific binding or adsorption properties, and the like.

In some aspects, conjugation of biomolecules to chromophoric polarization-sensitive nanoparticles can include attachment of a functional group, including but not limited to attachment of carboxyl groups to chromophoric polarization-sensitive nanoparticles. In some aspects, carboxyl groups are reacted to N-hydroxysuccinimide (NHS) in the presence of a carbodiimide such as 1-ethyl-3-[3-dimethylaminopropyl]carbodiimide hydrochloride (EDC) to produce amine-reactive esters of carboxylate groups for crosslinking with primary amine groups present on certain biomolecules.

In some aspects, carboxylated chromophoric polarization-sensitive nanoparticles are conjugated to a biomolecule, such as a protein, by mixing of the chromophoric polarization-sensitive nanoparticles and the biomolecules, e.g., in a HEPES buffer (20 mM, pH=7.4) solution containing 0.1% PEG (MW3350). Formation of a peptide bond between the carboxyl groups on chromophoric polarization-sensitive nanoparticles and the amine groups of the biomolecule are catalyzed by EDC. However, due to the intrinsically hydrophobic nature of the chromophoric polarization-sensitive nanoparticles, biomolecules tend to nonspecifically adsorb onto the particle surface. In some aspects, Triton X-100 and/or bovine serum albumin (BSA) are introduced to reduce non-specific adsorption of a biomolecule onto the surface of a chromophoric polymer hybrid nanoparticle.

In some aspects, a polymer hybrid nanoparticle is conjugated to one or more of a plurality of labels. For example, the polymer hybrid nanoparticle are conjugated to a labeling agent, such as a fluorescent labels (e.g., fluorescent dyes). In certain embodiments, the fluorescent label can have emission characteristics that are desired for a particular application. For example, the fluorescent label are a fluorescent dye that has a emission wavelength maximum between a range of 500 nm to 1100 nm, between a range of 600 nm to 1000 nm, between a range of 600 to 800 nm, between a range of 650 nm to 850 nm, or between a range of 700 nm to 800 nm. For another example, the fluorescent label are a fluorescent dye that has a emission wavelength maximum between a range of about 500 nm to about 1100 nm, between a range of about 600 nm to about 1000 nm, between a range of about 600 nm to about 800 nm, between a range of about 650 nm to about 850 nm, or between a range of about 700 nm to about 800 nm. One of ordinary skill in the art will appreciate the various dyes that are used as detectable labels and that have the emission characteristics above.

Non-limiting examples of fluorescent dyes that could be used as a conjugating molecule in the present disclosure include rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, and thiorhodamine, cyanine, indocarbocyanine, oxacarbocyanine, thiacarbocyanine, merocyanine, a cyanine dye (e.g., cyanine 2, cyanine 3, cyanine 3.5, cyanine 5, cyanine 5.5, cyanine 7), oxadiazole derivatives, pyridyloxazole, nitrobenzoxadiazole, benzoxadiazole, pyrene derivatives, cascade blue, oxazine derivatives, Nile red, Nile blue, cresyl violet, oxazine 170, acridine derivatives, proflavin, acridine orange, acridine yellow, arylmethine derivatives, xanthene dyes, sulfonated xanthenes dyes, Alexa Fluors (e.g., Alexa Fluor 594, Alexa Fluor 633, Alexa Fluor 647, Alexa Fluor 700), auramine, crystal violet, malachite green, tetrapyrrole derivatives, porphyrin, phtalocyanine, and bilirubin. In some aspects, the dyes are near-infrared dyes including, e.g., Cy5.5, IRdye 800, DyLight 750 or indocyanine green (ICG). In some aspects, near infrared dyes can include a cyanine dye (e.g., cyanine 2, cyanine 3, cyanine 3.5, cyanine 5, cyanine 5.5, cyanine 7). In certain embodiments, the detectable label can include xanthene dyes or sulfonated xanthenes dyes, such as Alexa Fluors (e.g., Alexa Fluor 594, Alexa Fluor 633, Alexa Fluor 647, Alexa Fluor 700).

In some aspects, polarization-sensitive nanoparticles are conjugated to peptides, in various aspects the peptides can be conjugated to detectable labels. The detectable labels are fluorescent labels (e.g., fluorescent dyes). In certain embodiments, the fluorescent label can have emission characteristics that are desired for a particular application. For example, the fluorescent label are a fluorescent dye that has a emission wavelength maximum between a range of 500 nm to 1100 nm, between a range of 600 nm to 1000 nm, between a range of 600 to 800 nm, between a range of 650 nm to 850 nm, or between a range of 700 nm to 800 nm. For another example, the fluorescent label are a fluorescent dye that has a emission wavelength maximum between a range of about 500 nm to about 1100 nm, between a range of about 600 nm to about 1000 nm, between a range of about 600 nm to about 800 nm, between a range of about 650 nm to about 850 nm, or between a range of about 700 nm to about 800 nm. One of ordinary skill in the art will appreciate the various dyes that are used as detectable labels and that have the emission characteristics above.

Non-limiting examples of fluorescent dyes that could be used as a conjugating molecule in the present disclosure include rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, and thiorhodamine, cyanine, indocarbocyanine, oxacarbocyanine, thiacarbocyanine, merocyanine, a cyanine dye (e.g., cyanine 2, cyanine 3, cyanine 3.5, cyanine 5, cyanine 5.5, cyanine 7), oxadiazole derivatives, pyridyloxazole, nitrobenzoxadiazole, benzoxadiazole, pyrene derivatives, cascade blue, oxazine derivatives, Nile red, Nile blue, cresyl violet, oxazine 170, acridine derivatives, proflavin, acridine orange, acridine yellow, arylmethine derivatives, xanthene dyes, sulfonated xanthenes dyes, Alexa Fluors (e.g., Alexa Fluor 594, Alexa Fluor 633, Alexa Fluor 647, Alexa Fluor 700), auramine, crystal violet, malachite green, tetrapyrrole derivatives, porphyrin, phtalocyanine, and bilirubin. In some aspects, the dyes are near-infrared dyes including, e.g., Cy5.5, IRdye 800, DyLight 750 or indocyanine green (ICG). In some aspects, near infrared dyes can include a cyanine dye (e.g., cyanine 2, cyanine 3, cyanine 3.5, cyanine 5, cyanine 5.5, cyanine 7). In certain embodiments, the detectable label can include xanthene dyes or sulfonated xanthenes dyes, such as Alexa Fluors (e.g., Alexa Fluor 594, Alexa Fluor 633, Alexa Fluor 647, Alexa Fluor 700). If an antibody to the dye could be found the conjugated dyes could be used both as a tracking, detecting or visualizing marker and as a retrieval handle.

The peptides in the libraries of the present disclosure are conjugated to biotin. In addition of extension of half-life, biotin could also act as an affinity handle for retrieval of the peptides from tissues or other locations. In one case, the peptides are conjugated, e.g., to a biotinidase resistant biotin with a PEG linker (e.g., NHS-dPEG4-Biotinidase resistant biotin). In some aspects, fluorescent biotin conjugates that can act both as a detectable label and an affinity handle are used. Non-limiting examples of commercially available fluorescent biotin conjugates include Atto 425-Biotin, Atto 488-Biotin, Atto 520-Biotin, Atto-550 Biotin, Atto 565-Biotin, Atto 590-Biotin, Atto 610-Biotin, Atto 620-Biotin, Atto 655-Biotin, Atto 680-Biotin, Atto 700-Biotin, Atto 725-Biotin, Atto 740-Biotin, fluorescein biotin, biotin-4-fluorescein, biotin-(5-fluorescein) conjugate, and biotin-B-phycoerythrin, alexa fluor 488 biocytin, alexa flour 546, alexa fluor 549, lucifer yellow cadaverine biotin-X, Lucifer yellow biocytin, Oregon green 488 biocytin, biotin-rhodamine and tetramethylrhodamine biocytin. In some other examples, the conjugates could include chemiluminescent compounds, colloidal metals, luminescent compounds, enzymes, radioisotopes, and paramagnetic labels.

In addition to the examples described herein, in some aspects other strategies and methods for conjugation of biomolecules to chromophoric polarization-sensitive nanoparticles are used, including those disclosed, e.g., in WO2011/057295 and WO2013/101902. Other strategies and methods for conjugation of biomolecules to chromophoric polarization-sensitive nanoparticles are found by one of ordinary skill in the art, for example in Bioconjugate Techniques (Academic Press, New York, 1996 or later versions).

Methods for Making Hybrid Nanoparticles

The chromophoric polarization-sensitive nanoparticles used herein are formed by any method known in the art for collapsing polymers, including without limitation, methods relying on precipitation, methods relying on the formation of emulsions (e.g., mini or micro emulsion), and methods relying on condensation.

As provided herein, the chromophoric polarization-sensitive nanoparticles are made using a variety of methods. For example, described herein are methods involving precipitation of the polymers to form the polarization-sensitive nanoparticles. It will be appreciated the myriad ways of forming polarization-sensitive nanoparticles, which can also include, e.g., emulsion-based techniques. Similarly, one of ordinary skill in the art will appreciate the variety of methods described herein with respect to functionalizing the polarization-sensitive nanoparticles by, e.g., pre- and post-functionalization with functional groups, such as hydrophobic functional groups, hydrophilic functional groups, or a combination thereof.

In some aspects, chromophoric polarization-sensitive nanoparticles are formed by precipitation. This technique involves the rapid addition (e.g., facilitated by sonication or vigorous stirring) of a dilute chromophoric polymer solution (e.g., chromophoric polymer dissolved in an organic solvent) into an excess volume of non-solvent (but miscible with the organic solvent), such as water or another physiologically relevant aqueous solution. For example, in some of the procedures described herein, the chromophoric polymer are first dissolved into an organic solvent where the solubility is good (good solvent), such as THF (tetrahydrofuran), after which the dissolved polymer in THF is added to an excess volume of water or buffer solution, which is a poor solvent for the hydrophobic chromophoric polymers but which is miscible with the good solvent (THF). The resulting mixture is sonicated or vigorously stirred to assist the formation of chromophoric polarization-sensitive nanoparticles, then the organic solvent is removed to leave behind well dispersed chromophoric hybrid nanoparticles. In using this procedure, the chromophoric polymer should be sufficiently hydrophobic to dissolve into the organic solvent (e.g., THF). The introduction of a high density of hydrophilic functional groups on side chains for coupling to biomolecules or high density of hydrophilic side chains will make the resulting polymer, in a fashion similar or identical to the behavior of polyelectrolytes, insoluble or poorly soluble in an organic solvent (e.g., THF).

In some aspects, a solution of blended polymers are mixed into a solution of THF and quickly injected into water, in various aspects using high sonication power to precipitate the hybrid nanoparticles. In various aspects, any hydrophobic polymers, for example a semiconducting polymer such as PFBT, are isolated in the core of the hybrid nanoparticle. The THF are removed from the hybrid nanoparticles using a combination of heat and addition of nitrogen through a bubbling procedure.

In some aspects, methods, compositions and kits are provided for the use of chromophoric polarization-sensitive nanoparticles formed by other methods, including but not limited to various methods based on emulsions (e.g., mini or micro emulsion) or precipitations or condensations. Other polymers having hydrophobic functional groups are employed, in which the hydrophobic functional groups do not affect the collapse and stability of the chromophoric polymer hybrid nanoparticle. The hydrophobic functional groups on the surface of the hybrid nanoparticles can then be converted to hydrophilic functional groups (e.g., by post-functionalization) for bioconjugation or directly link the hydrophobic functional groups to biomolecules. This latter approach can work particularly well using functional groups that are both hydrophobic and clickable (i.e., chemical reactions that fall within the framework of click chemistry), including but not limited to alkyne, strained alkyne, azide, diene, alkene, cyclooctyne, and phosphine groups.

In one case, the present disclosure provides a method for making a rationally functionalized single-chain chromophoric hybrid nanoparticle having a defined number of reactive functional groups on its surface, the method comprising the steps of: (a) collapsing a homogenous population of semiconducting polymers conjugated to one or more reactive functional group in an aqueous environment to form a chromophoric hybrid nanoparticle comprising a plurality of reactive functional groups; (b) attaching the hybrid nanoparticle to a solid phase at a single point by forming a covalent bond between a reactive functional group on the hybrid nanoparticle and the solid phase; (c) washing the hybrid nanoparticle in an organic solvent to disrupt the structure of the hybrid nanoparticle and to retain only the polymer conjugated to the solid surface; (d) washing the attached polymer back into an aqueous environment to collapse the polymer into a single-chain chromophoric hybrid nanoparticle; and (e) cleaving the bond between the solid phase and the reactive functional group to release the single-chain chromophoric hybrid nanoparticle from the solid phase. In some aspects, the step of cleaving the bond maintains a reactive functional group on the surface of the hybrid nanoparticle. In certain embodiments, the step of cleaving the bond modifies the reactive functional group, generating a different reactive functional group on the surface of the hybrid nanoparticle.

In another case, the present disclosure provides a method for making a monovalent chromophoric hybrid nanoparticle having a single reactive functional group on its surface, the method comprising the steps of: (a) collapsing a semiconducting polymer conjugated to one or more reactive functional groups in an aqueous environment to form a chromophoric hybrid nanoparticle comprising a plurality of reactive functional groups; (b) attaching the hybrid nanoparticle to a solid phase at a single point by forming a covalent bond between a reactive functional group on the hybrid nanoparticle and the solid phase; (c) treating the hybrid nanoparticle to remove all of the unbound reactive functional groups from the surface of the hybrid nanoparticle; and (d) cleaving the bond between the solid phase and the reactive functional group to release the chromophoric hybrid nanoparticle from the solid phase. In some aspects, the step of cleaving the bond maintains a reactive functional group on the surface of the hybrid nanoparticle. In certain embodiments, the step of cleaving the bond modifies the reactive functional group, generating a different reactive functional group on the surface of the hybrid nanoparticle.

For single polymer molecules, collapse into a single polymer hybrid nanoparticle can be facilitated, e.g., with low polymer concentrations where polymers are spatially distributed in solution such that only intramolecular collapse occurs, rather than intermolecular collapse with another polymer molecule. Dilute solutions for single polymer hybrid nanoparticle formation can range from less than about 1000 ppm, less than about 500 ppm, less than about 100 ppm, less than about 50 ppm, less than about 20 ppm, less than about 10 ppm, less than about 5 ppm, less than about 1 ppm, or less. An example first step of the methods herein is to synthesize chromophoric polymer molecule bearing functional groups, such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and combinations thereof. In general, any other functional groups that allow bioconjugation are used. Such functional groups could be found by one of ordinary skill in the art, for example in Bioconjugate Techniques (Academic Press, New York, 1996 or later versions) the content of which is herein incorporated by reference in its entirety for all purposes. A functional group can be created with covalent bonding to the backbone, side chain, or terminating unit of the chromophoric polymer. In the second step, the functionalized chromophoric polymer is used as a precursor for preparing single-molecule hybrid nanoparticle by using the solvent mixing method as shown in Example 1. In one case, the single-molecule hybrid nanoparticle could be monovalent (e.g., with only one functional group available for bioconjugation) when each polymer precursor molecule has just one functional group. In other embodiments, the single-molecule hybrid nanoparticle could be bivalent, or multivalent when each polymer precursor molecule has two, or more functional groups, which are useful for certain applications.

In some aspects, any functionalized multi-molecule chromophoric polymer hybrid nanoparticle can be modified to form a single-molecule polymer hybrid nanoparticle that are monovalent, bivalent, or multivalent. The modification is to remove some polymer molecules from the hybrid nanoparticle, but leave only one molecule that may have just one functional group, two or more functional groups. In one case, an engineered surface can be used to facilitate the modification. The engineered surface may have certain functional groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and combinations thereof. In general, any other functional groups that are suitable for bioconjugation are used. Such functional groups could be found by one of ordinary skill in the art, for example in Bioconjugate Techniques (Academic Press, New York, 1996 or later versions) the content of which is herein incorporated by reference in its entirety for all purposes. The surface can be a flat surface such as a coverslip or a curved surface from any particles. The surfaces are silica, metal, semiconducting, silicon, and different polymer surfaces. The functionalized multi-molecule chromophoric polymer hybrid nanoparticle described above is attached to the surface by only one chromophoric polymer molecule via any stable physical or chemical association. All the free molecules (except the one associated with the surface) in the chromophoric polymer hybrid nanoparticle are removed, such as by washing the surface with an organic solvent, so that only the molecule associated with the surface is retained. Then the single-molecule chromophoric hybrid nanoparticle can be released from the surface by any physical or chemical methods. The resulting single-molecule hybrid nanoparticle could be monovalent, bivalent, or multivalent, depending on the number of functional groups in the original polymer molecule. The functional groups on the surface or in the polymers include but not limit to those used for click chemistry, such as alkyne, strained alkyne, azide, diene, alkene, cyclooctyne, and phosphine groups.

In some aspects, monovalent chromophoric polarization-sensitive nanoparticles are prepared by modifying any functionalized multivalent chromophoric polarization-sensitive nanoparticles to monovalent hybrid nanoparticles. The original functionalized multivalent polymer hybrid nanoparticle may comprise one or more chromophoric polymer molecules. The original functionalized polymer hybrid nanoparticle may also comprise chromophoric polymer, physically mixed or chemically cross-linked with other components including, e.g., fluorescent dye, inorganic luminescent materials, magnetic materials, metal materials, which can have additional functionalities such as magnetic functions, plasmon resonance functions, and the like.

This case includes a two-step process: the first step is to prepare functionalized chromophoric polarization-sensitive nanoparticles bearing functional groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and combinations thereof. In general, any other functional groups that allow bioconjugation are used. Such functional groups could be found by one of ordinary skill in the art, for example in Bioconjugate Techniques (Academic Press, New York, 1996 or later versions) the content of which is herein incorporated by reference in its entirety for all purposes. The chromophoric polarization-sensitive nanoparticles are functionalized by attaching any organic molecule, such as by any stable physical or chemical association, to the chromophoric polarization-sensitive nanoparticles. The functionalization molecule is attached to the chromophoric polarization-sensitive nanoparticles by physical association or chemical bonding, and provides surface functional groups on chromophoric polymer hybrid nanoparticle. Preferably, the functionalization molecule is a polymer, which may or may not be chromophoric. Methods for preparing functionalized multivalent hybrid nanoparticles are known, for example, see, U.S. Provisional Patent Application Ser. No. 61/259,611, the contents of which are herein incorporated by reference in their entirety for all purposes.

The second step is to modify the functionalized multivalent chromophoric polymer hybrid nanoparticle to monovalent polymer hybrid nanoparticle. The modification is to passivate or remove the majority of functional groups, but leave only one active functional group. In one case, an engineered surface can be used to facilitate the modification. The engineered surface may have certain functional groups such as carboxylic acid or salts thereof, amino, mercapto, azido, alkyne, phosphine, cyclooctyne, aldehyde, hydroxyl, carbonyl, sulfate, sulfonate, phosphate, cyanate, ester, succinimidyl ester, substituted derivatives thereof, and combinations thereof. The surface can be a flat surface such as a coverslip or a curved surface from any particles. The surfaces are silica, metal, semiconducting, silicon, and different polymer surfaces. The engineered surface can be a flat surface such as a coverslip or a curved surface from any particles. In some case, the polarization-sensitive nanoparticles are attached to the surface by click chemistry. The functional groups on the surface or in the polymer molecules include but not limit to those used for click chemistry, such as alkyne, strained alkyne, azide, diene, alkene, cyclooctyne, and phosphine groups. The PFBT hybrid nanoparticles are cleaved after surface passivation to form monovalent hybrid nanoparticles. The original functionalized multivalent chromophoric hybrid nanoparticle described above is attached to the surface by only one functional group via any stable physical or chemical association. All the free functional groups (except the one connected to the surface) on the chromophoric hybrid nanoparticle are passivated or removed. Then the chromophoric hybrid nanoparticle can be released from the surface by any physical or chemical method and the modified chromophoric hybrid nanoparticle would have only one functional group, which could be the original one or a different one.

As taught in U.S. Provisional Patent Application Ser. No. 61/259,611, in one case, the functionalized hybrid nanoparticle can contain a polystyrene based comb-like polymer. Non limiting examples of polystyrene based comb-like polymers include, polystyrene graft acrylic acid, polystyrene graft ethylene oxide functionalized with carboxy, polystyrene graft ethylene oxide functionalized with amine, polystyrene graft ethylene oxide functionalized with thiol, polystyrene graft ethylene oxide functionalized with succinimidyl ester, polystyrene graft ethylene oxide functionalized with azide, polystyrene graft ethylene oxide functionalized with alkyne, polystyrene graft ethylene oxide functionalized with cyclooctyne, polystyrene graft ethylene oxide functionalized with ester, phosphine, polystyrene graft butyl alcohol, and the like.

In another case, the functionalized hybrid nanoparticle can contain a poly(methyl methacrylate) based comb-like polymers. Non-limiting examples of poly(methyl methacrylate) based comb-like polymers include, poly(methyl methacrylate) graft acrylic acid, poly(methyl methacrylate) graft ethylene oxide functionalized with carboxy, poly(methyl methacrylate) graft ethylene oxide functionalized with amine, poly(methyl methacrylate) graft ethylene oxide functionalized with thiol, poly(methyl methacrylate) graft ethylene oxide functionalized with succinimidyl ester, poly(methyl methacrylate) graft ethylene oxide functionalized with azide, poly(methyl methacrylate) graft ethylene oxide functionalized with alkyne, poly(methyl methacrylate) graft ethylene oxide functionalized with cyclooctyne, poly(methyl methacrylate) graft ethylene oxide functionalized with ester, poly(methyl methacrylate) graft ethylene oxide functionalized with phosphine, and the like.

In yet another case, the functionalized hybrid nanoparticle can contain a comb-like polymer comprising carboxyl, amine, thiol, ester, succinimidyl ester, azide, alkyne, cyclooctyne, or phosphine groups.

Likewise, in one case, the functionalized hybrid nanoparticle can contain a polymer functionalized on the terminal monomeric unit, for example with a carboxyl, amine, thiol, ester, succinimidyl ester, azide, alkyne, cyclooctyne, phosphine, or similar functional group. Examples of polymers that are used include, without limitation, poly(meth)acrylate polymers, polyacrylamide polymers, polyisobutylene, polydiene, polyphenylene, polyethylene, poly(ethylene glycol), polylactide, polystyrene, polysiloxane, poly(vinyl pyridine), poly(vinylpyrrolidone), polyurethane, a block copolymer thereof, a random or alternating copolymer thereof, and the like.

Although the present disclosure provides for forming hybrid nanoparticles comprising semiconducting polymers, non-semiconducting polymers, a blend of semiconducting polymers at various weights, ratios and parameters described herein, an exemplary hybrid nanoparticle may comprise two matrix polymers, P70 and PS-PEG-COOH in addition to a semiconducting polymer, such as, PFBT. In some aspects, a hybrid nanoparticle with two matrix polymers, both of which are amphiphilic polymers, may result in a small hybrid nanoparticle with the high sensitivity to excitation polarization and high polarized emission.

Characteristics of Hybrid Nanoparticles

Hybrid nanoparticles of the present disclosure may have any number of characteristics. The characteristics described herein are not limiting of the potential characteristics that a hybrid nanoparticle may have. Characteristics of hybrid nanoparticles include shape, solubility, critical dimension, mass, mass ratios, anisotropy, quantum yield, absorption, emission, quenching, brightness and the like.

Hybrid nanoparticles of the disclosure, or fragments or chemical precursors thereof, are soluble or insoluble in various solvents. Types of solvents include, for example, polar solvents, non-polar solvents, aqueous solvents, non-aqueous solvents, ionic liquids, organic solvents, and polymeric solvents. Non-limiting examples of solvents include: water; tetrahydrofuran (THF); morpholine; N-methylmorpholine; methanol (MeOH); ethanol (EtOH); propanol (PrOH); isopropanol (iPrOH); t-butanol (tBuOH); acetic acid (AcOH); ethylene glycol; propylene glycol; methyl acetate (MeOAc); ethyl acetate (EtOAc); ether ($Et_2O$); methyl-tert-butyl ether (MTBE); dimethoxyethane (DME); glyme; diglyme; tetraglyme; methylene chloride ($CH_2Cl_2$); chloroform ($CHCl_3$); carbon tetrachloride ($CCl_4$); 1,1-dichloroethane ($CHCl_2CH_3$); 1,2-dichloroethane ($CH_2ClCH_2Cl$); carbon disulfide ($CS_2$); dimethyl sulfoxide (DMSO); dimethylformamide (DMF); acetone (MeAc); 2-butanone (EtAc); pentane, hexane, hexanes, cyclohexane; benzene; toluene; xylene; xylenes; and pyridine.

Hybrid nanoparticles of the disclosure, or fragments or chemical precursors thereof, are physically associated or chemically linked with polyethylene glycol (PEG) groups. A PEG group can include, for example, about 2, about 4, about 6, about 8, about 10, about 20, about 30, about 40, about 50, about 60, about 70, about 80, about 90, about 100, about 150, about 200, about 250, about 300, about 350, about 400, about 450, about 500, about 550, about 600, about 650, about 700, about 750, about 800, about 850, about 900, about 950, about 1000, about 1250, about 1500, about 1750, about 2000, about 2250, about 2500, about 2750, about 3000, about 3250, about 3500, about 3750, about 4000, about 4250, about 4500, about 4750, or about 5000 ethylene glycol subunits. One or more ethylene glycol submits are modified with any substituent described herein, for example, hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, haloalkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, urethane groups, and ester groups.

Hybrid nanoparticles of the disclosure, or fragments or chemical precursors thereof, can have at least one critical dimension. In some aspects, the critical dimension of the chromophoric polymer hybrid nanoparticle used is 200 nm or less. In some aspects, the critical dimension of the chromophoric polymer hybrid nanoparticle used is 180 nm or less. In some aspects, the critical dimension is 170 nm or less. In some aspects, the critical dimension is 160 nm or less. In some aspects, the critical dimension is 150 nm or less. In some aspects, the critical dimension is 155 nm or less. In some aspects, the critical dimension is 150 nm or less. In some aspects, the critical dimension is 145 nm or less. In some aspects, the critical dimension is 140 nm or less. In some aspects, the critical dimension is 135 nm or less. In some aspects, the critical dimension is 130 nm or less. In some aspects, the critical dimension is 125 nm or less. In some aspects, the critical dimension is 120 nm or less. In some aspects, the critical dimension is 115 nm or less. In some aspects, the critical dimension is 110 nm or less. In some aspects, the critical dimension is 105 nm or less. In some aspects, the critical dimension is 100 nm or less. In some aspects, the critical dimension is 95 nm or less. In some aspects, the critical dimension is 90 nm or less. In some aspects, the critical dimension is 85 nm or less. In some aspects, the critical dimension is 80 nm or less. In some aspects, the critical dimension is 75 nm or less. In some aspects, the critical dimension is 70 nm or less. In some aspects, the critical dimension is 65 nm or less. In some aspects, the critical dimension is 60 nm or less. In some aspects, the critical dimension is 55 nm or less. In some aspects, the critical dimension is 50 nm or less. In some aspects, the critical dimension is 45 nm or less. In some aspects, the critical dimension is 40 nm or less. In some aspects, the critical dimension is 35 nm or less. In some aspects, the critical dimension is 30 nm or less. In some aspects, the critical dimension is 25 nm or less. In some aspects, the critical dimension is 20 nm or less. In some aspects, the critical dimension is 15 nm or less. In some aspects, the critical dimension is 10 nm or less. In some aspects, the critical dimension is 5 nm or less.

In some aspects, the critical dimension of the chromophoric polymer hybrid nanoparticle used is 200 nm or greater. In some aspects, the critical dimension of the chromophoric polymer hybrid nanoparticle used is 180 or greater. In some aspects, the critical dimension is 170 nm or greater. In some aspects, the critical dimension is 160 nm or greater. In some aspects, the critical dimension is 150 nm or greater. In some aspects, the critical dimension is 155 nm or greater. In some aspects, the critical dimension is 150 nm or greater. In some aspects, the critical dimension is 145 nm or greater. In some aspects, the critical dimension is 140 nm or greater. In some aspects, the critical dimension is 135 nm or greater. In some aspects, the critical dimension is 130 nm or greater. In some aspects, the critical dimension is 125 nm or greater. In some aspects, the critical dimension is 120 nm or greater. In some aspects, the critical dimension is 115 nm or greater. In some aspects, the critical dimension is 110 nm or greater. In some aspects, the critical dimension is 105 nm or greater. In some aspects, the critical dimension is 100 nm or greater. In some aspects, the critical dimension is 95 nm or greater. In some aspects, the critical dimension is 90 nm or greater. In some aspects, the critical dimension is 85 nm or greater. In some aspects, the critical dimension is 80 nm or greater. In some aspects, the critical dimension is 75 nm or greater. In some aspects, the critical dimension is 70 nm or greater. In some aspects, the critical dimension is 65 nm or greater. In some aspects, the critical dimension is 60 nm or greater. In some aspects, the critical dimension is 55 nm or greater. In some aspects, the critical dimension is 50 nm or greater. In some aspects, the critical dimension is 45 nm or greater. In some aspects, the critical dimension is 40 nm or greater. In some aspects, the critical dimension is 35 nm or greater. In some aspects, the critical dimension is 30 nm or greater. In some aspects, the critical dimension is 25 nm or greater. In some aspects, the critical dimension is 20 nm or greater. In some aspects, the critical dimension is 15 nm or greater. In some aspects, the critical dimension is 10 nm or greater. In some aspects, the critical dimension is 5 nm or greater.

In some aspects, the critical dimension of the chromophoric polymer hybrid nanoparticle used is about 200 nm. In some aspects, the critical dimension of the chromophoric polymer hybrid nanoparticle used is about 180 nm. In some aspects, the critical dimension is about 170 nm. In some aspects, the critical dimension is about 160 nm. In some aspects, the critical dimension is about 155 nm. In some aspects, the critical dimension is about 150 nm. In some aspects, the critical dimension is about 145 nm. In some aspects, the critical dimension is about 140 nm. In some aspects, the critical dimension is about 135 nm. In some aspects, the critical dimension is about 130 nm. In some aspects, the critical dimension is about 125 nm. In some aspects, the critical dimension is about 120 nm. In some aspects, the critical dimension is about 115 nm. In some aspects, the critical dimension is about 110 nm. In some aspects, the critical dimension is about 105 nm. In some aspects, the critical dimension is about 100 nm. In some aspects, the critical dimension is about 95 nm. In some aspects, the critical dimension is about 90 nm. In some aspects, the critical dimension is about 85. In some aspects, the critical dimension is about 80 nm. In some aspects, the critical dimension is about 75 nm. In some aspects, the critical dimension is about 70 nm. In some aspects, the critical dimension is about 65 nm. In some aspects, the critical dimension is about 60 nm. In some aspects, the critical dimension is about 55 nm. In some aspects, the critical dimension is about 50 nm. In some aspects, the critical dimension is about 45 nm. In some aspects, the critical dimension is about 40 nm. In some aspects, the critical dimension is about 35 nm. In some aspects, the critical dimension is about 30 nm. In some aspects, the critical dimension is about 25 nm. In some aspects, the critical dimension is about 20 nm. In some aspects, the critical dimension is about 15 nm. In some aspects, the critical dimension is about 10 nm. In some aspects, the critical dimension is about 5 nm.

In some aspects, the chromophoric polymer hybrid nanoparticle used has a critical dimension greater than 1 nm and less than 1000 nm. In some aspects, the chromophoric polymer hybrid nanoparticle used has a critical dimension greater than 10 nm and less than 1000 nm. In some aspects, the chromophoric polymer hybrid nanoparticle used has a critical dimension greater than 20 nm and less than 1000 nm. In some aspects, the chromophoric polymer hybrid nanoparticle used has a critical dimension greater than 30 nm and less than 1000 nm. In some aspects, the chromophoric polymer hybrid nanoparticle used has a critical dimension greater than 40 nm and less than 1000 nm. In some aspects, the chromophoric polymer hybrid nanoparticle used has a critical dimension greater than 50 nm and less than 1000 nm. In some aspects, the chromophoric polymer hybrid nanoparticle used has a critical dimension greater than 1 nm and less than 100 nm. In some aspects, the chromophoric polymer hybrid nanoparticle used has a critical dimension greater than 1 nm and less than 90 nm. In some aspects, the chromophoric polymer hybrid nanoparticle used has a critical dimension greater than 1 nm and less than 80 nm. In some aspects, the chromophoric polymer hybrid nanoparticle used has a critical dimension greater than 1 nm and less than 70 nm. In some aspects, the chromophoric polymer hybrid nanoparticle used has a critical dimension greater than 1 nm and less than 60 nm. In some aspects, the chromophoric polymer hybrid nanoparticle used has a critical dimension greater than 1 nm and less than 50 nm. In some aspects, the chromophoric polymer hybrid nanoparticle used has a critical dimension greater than 1 nm and less than 40 nm. In some aspects, the chromophoric polymer hybrid nanoparticle used has a critical dimension greater than 1 nm and less than 30 nm. In some aspects, the chromophoric polymer hybrid nanoparticle used has a critical dimension greater than 1 nm and less than 20 nm. In some aspects, the chromophoric polymer hybrid nanoparticle used has a critical dimension greater than 1 nm and less than 10 nm.

In some aspects, the chromophoric polymer hybrid nanoparticle used has a critical dimension of about greater than about 1 nm and less than about 1000 nm. In some aspects, the chromophoric polymer hybrid nanoparticle used has a critical dimension of about greater than about 10 nm and less than about 1000 nm. In some aspects, the chromophoric polymer hybrid nanoparticle used has a critical dimension of about greater than about 20 nm and less than about 1000 nm. In some aspects, the chromophoric polymer hybrid nanoparticle used has a critical dimension of about greater than about 30 nm and less than about 1000 nm. In some aspects, the chromophoric polymer hybrid nanoparticle used has a critical dimension of about greater than about 40 nm and less than about 1000 nm. In some aspects, the chromophoric polymer hybrid nanoparticle used has a critical dimension of about greater than about 50 nm and less than about 1000 nm. In some aspects, the chromophoric polymer hybrid nanoparticle used has a critical dimension of about greater than about 1 nm and less than about 100 nm. In some aspects, the chromophoric polymer hybrid nanoparticle used has a critical dimension of about greater than about 1 nm and less than about 90 nm. In some aspects, the chromophoric polymer hybrid nanoparticle used has a critical dimension of about greater than about 1 nm and less than about 80 nm. In some aspects, the chromophoric polymer hybrid nanoparticle used has a critical dimension of about greater than about 1 nm and less than about 70 nm. In some aspects, the chromophoric polymer hybrid nanoparticle used has a critical dimension of about greater than about 1 nm and less than about 60 nm. In some aspects, the chromophoric polymer hybrid nanoparticle used has a critical dimension of about greater than about 1 nm and less than about 50 nm. In some aspects, the chromophoric polymer hybrid nanoparticle used has a critical dimension of about greater than about 1 nm and less than about 40 nm. In some aspects, the chromophoric polymer hybrid nanoparticle used has a critical dimension of about greater than about 1 nm and less than about 30 nm. In some aspects, the chromophoric polymer hybrid nanoparticle used has a critical dimension of about greater than about 1 nm and less than about 20 nm. In some aspects, the chromophoric polymer hybrid nanoparticle used has a critical dimension of about greater than about 1 nm and less than about 10 nm.

The possible shape of the hybrid nanoparticle is essentially unlimited. However, in certain embodiments, the shape is selected from a sphere, a cylinder, an ellipsoid, a polyhedron, a prism, a rod, and a wire. The shape of the hybrid nanoparticle can contribute to the detection properties, as will be appreciated by those of skill in the art (e.g., nano-rods may have different optical properties than nano-spheres).

The nano-scale size of the hybrid nanoparticle is essential in order to bypass issues presented by large particle sizes. For example, when attaching hybrid nanoparticles to a target molecule (e.g., a protein) for photoluminescence imaging, relatively large particles have more surface area available for non-specific binding to molecules other than the target, or adsorption to a surface.

The provided hybrid nanoparticles are optimized for use as photo-luminescent reporters that are attached to a target molecule as part of an analysis method, system or kit. The hybrid nanoparticles should be easily detectable using photoluminescence and should have specificity for their target molecules.

The optical properties, such as absorption wavelength, for a given chromophoric polymer hybrid nanoparticle are tuned by modifying its composition and geometry. Semiconducting polymers have been developed with absorption wavelengths ranging from UV to infrared, including the entire visible spectrum. In some aspects, chromophoric polarization-sensitive nanoparticles having a peak absorption wavelength between 200 nm and 300 nm, 250 nm and 350 nm, 300 nm and 400 nm, 350 nm and 450 nm, between 400 nm and 500 nm, 450 nm and 550 nm, 500 nm and 600 nm, 550 nm and 650 nm, 600 nm and 700 nm, 650 nm and 750 nm, 700 nm and 800 nm, 750 nm and 850 nm, 800 nm and 900 nm, 850 nm and 950 nm, or 900 nm and 1000 nm are used.

In other embodiments, chromophoric polarization-sensitive nanoparticles having a peak absorption wavelength between about 200 nm and about 300 nm, about 250 nm and about 350 nm, about 300 nm and about 400 nm, about 350 nm and about 450 nm, between about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm are used.

Semiconducting polymers have been developed with emission wavelengths ranging from UV to infrared, including the entire visible spectrum. In some aspects, chromophoric polarization-sensitive nanoparticles having a peak emission wavelength between 200 nm and 300 nm, 250 nm and 350 nm, 300 nm and 400 nm, 350 nm and 450 nm, 400 nm and 500 nm, 450 nm and 550 nm, 500 nm and 600 nm, 550 nm and 650 nm, 600 nm and 700 nm, 650 nm and 750 nm, 700 nm and 800 nm, 750 nm and 850 nm, 800 nm and 900 nm, 850 nm and 950 nm, 900 nm and 1000 nm, 950 nm and 1050 nm, 1000 nm and 1100 nm, 1150 nm and 1250 nm, or 1200 nm and 1300 nm are used.

In other embodiments, chromophoric polarization-sensitive nanoparticles having a peak emission wavelength between about 200 nm and about 300 nm, about 250 nm and about 350 nm, about 300 nm and about 400 nm, about 350 nm and about 450 nm, about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, about 900 nm and about 1000 nm, about 950 nm and about 1050 nm, about 1000 nm and about 1100 nm, about 1150 nm and about 1250 nm, or about 1200 nm and about 1300 nm are used.

In some aspects, the methods, compositions and kits provided will make use of chromophoric polarization-sensitive nanoparticles with emissions. Emissions are advantageous for certain applications, including but not limited to multiplexing applications. The emission wavelength of the polarization-sensitive nanoparticles can vary from ultraviolet to near infrared region. The full width at half maximum (FWHM) of the emission band is less than 7.0 nm. In some aspects, the FWHM is less than 6.5 nm. In some aspects, the FWHM is less than 6.0 nm. In some aspects, the FWHM is less than 5.5 nm. In some aspects, the FWHM is less than 5.0 nm. In some aspects, the FWHM is less than 4.5 nm. In some aspects, the FWHM is less than 4.0 nm. In some aspects, the FWHM is less than 3.5 nm. In some aspects, the FWHM is less than 3.0 nm. In some aspects, the FWHM is less than 2.5 nm. In some aspects, the FWHM is less than 2.0 nm. In some aspects, the FWHM is less than 1.0 nm. In some aspects, the FWHM of the polarization-sensitive nanoparticles described herein can range between 0.5 nm to 7.0 nm, from 1.0 nm to 6.0 nm, from 2.0 nm to 5.0 nm, or from 3.0 nm to 4.5 nm.

In other embodiments, the methods, compositions and kits provided will make use of chromophoric polarization-sensitive nanoparticles with emissions which are advantageous for certain applications, including but not limited to multiplexing applications. The emission wavelength of the polarization-sensitive nanoparticles can vary from ultraviolet to near infrared region. The full width at half maximum (FWHM) of the emission band is less than 7.0 nm. In some aspects, the FWHM is less than about 6.5 nm. In some aspects, the FWHM is less than about 6.0 nm. In some aspects, the FWHM is less than about 5.5 nm. In some aspects, the FWHM is less than about 5.0 nm. In some aspects, the FWHM is less than about 4.5 nm. In some aspects, the FWHM is less than about 4.0 nm. In some aspects, the FWHM is less than about 3.5 nm. In some aspects, the FWHM is less than about 3.0 nm. In some aspects, the FWHM is less than about 2.5 nm. In some aspects, the FWHM is less than about 2.0 nm. In some aspects, the FWHM is less than about 1.0 nm. In some aspects, the FWHM of the polarization-sensitive nanoparticles described herein can range between about 0.5 nm to about 7.0 nm, from about 1.0 nm to about 6.0 nm, from about 2.0 nm to about 5.0 nm, or from about 3.0 nm to about 4.5 nm.

In some aspects, the FHWM may change after functionalization. In an exemplary case, the FHWM is 1.5 nm before functionalization and 3.7 nm after functionalization.

In some aspects, the emissive polymers for making chromophoric polarization-sensitive nanoparticles include boron-dipyrromethene (4,4-difluoro-4-bora-3a,4a-diaza-s-indacene, BODIPY) and or their derivatives, and/or other boron-containing monomers and their derivatives, as monomers. BODIPY and other boron containing monomers and their derivatives include but are not limited to their alkyl derivatives, aryl derivatives, alkyne derivatives, aromatic derivatives, alkoxide derivatives, aza derivatives, BODIPY extended and other BODIPY derivatives. The emissive polymers can also include any other monomers. The BODIPY-based-monomers are energy acceptors and other monomers are energy donors so that the final chromophoric polarization-sensitive nanoparticles can exhibit emissions. The narrowband emissive chromophoric polymers in good solvents may exhibit broad emissions or narrow emissions. A comprehensive description of chromophoric polarization-sensitive nanoparticles with emissions, including BODIPY and other boron containing monomers and their derivatives, is described in WO2013/101902, which is herein incorporated by reference in its entirety.

In various aspects, hybrid nanoparticles are small, for example having a given diameter and a given width. In some aspects, the diameter can be a mean diameter, for example of 7.5 nm. In other embodiments, the mean diameter can be 3 nm, 3.5 nm, 4 nm, 4.5 nm. 5 nm, 5.5 nm, 6 nm, 6.5 nm, 7 nm, 7.5 nm, 8 nm, 8.5 nm, 9 nm, 9.5 nm or 10 nm. The mean diameter can be about 3 nm, 3.5 nm, 4 nm, 4.5 nm. 5 nm, 5.5 nm, 6 nm, 6.5 nm, 7 nm, 7.5 nm, 8 nm, 8.5 nm, 9 nm, 9.5 nm or 10 nm. The mean diameter can be greater than 3 nm, 3.5 nm, 4 nm, 4.5 nm. 5 nm, 5.5 nm, 6 nm, 6.5 nm, 7 nm, 7.5 nm, 8 nm, 8.5 nm, 9 nm, 9.5 nm or 10 nm. The mean diameter can be less than 3 nm, 3.5 nm, 4 nm, 4.5 nm. 5 nm, 5.5 nm, 6 nm, 6.5 nm, 7 nm, 7.5 nm, 8 nm, 8.5 nm, 9 nm, 9.5 nm or 10 nm. In some aspects, the width can be a peak width, for example, of 1.5 nm. In other embodiments, the peak width can be 0.5 nm, 1 nm, 1.5 nm, 2 nm, 2.5 nm, 3 nm, 3.5 nm, 4 nm, 4.5 nm or 5 nm. In other embodiments, the peak width are greater than 0.5 nm, 1 nm, 1.5 nm, 2 nm, 2.5 nm, 3 nm, 3.5 nm, 4 nm, 4.5 nm or 5 nm. In other embodiments, the peak width can be less than 0.5 nm, 1 nm, 1.5 nm, 2 nm, 2.5 nm, 3 nm, 3.5 nm, 4 nm, 4.5 nm or 5 nm. In other embodiments, the peak width are about 0.5 nm, 1 nm, 1.5 nm, 2 nm, 2.5 nm, 3 nm, 3.5 nm, 4 nm, 4.5 nm or 5 nm. In various aspects, the diameter and width may change before and after functionalization. For example, before functionalization, the diameter can be greater than, less than or about 3 nm, 3.5 nm, 4 nm, 4.5 nm. 5 nm, 5.5 nm, 6 nm, 6.5 nm, 7 nm, 7.5 nm, 8 nm, 8.5 nm, 9 nm, 9.5 nm or 10 nm whereas after functionalization, the diameter can be greater than, less than or about 7 nm, 7.5 nm, 8 nm, 8.5 nm, 9 nm, 9.5 nm, 10 nm, 10.5 nm, 11 nm, 11.5 nm, 12 nm, 12.5 nm, 13 nm, 13.5 nm, 14.5 nm, or 15 nm. In an exemplary case, the diameter can be 7.5 nm before functionalization and 12.0 nm after functionalization.

Hybrid nanoparticles may have a zeta potential, for example, which varies in different buffers. In some aspects, the zeta potential of a hybrid nanoparticle can be low, for example, −28 mV in 20 mM HEPES buffer at pH 7.2. In other embodiments, the zeta potential are −40 mV, −39 mV, −38 mV, −37 mV, −36 mV, −35 mV, −34 mV, −33 mV, −32 mV, −31 mV, −30 mV, −29 mV, −28 mV, −27 mV, −26 mV, −25 mV, −24 mV, −23 mV, −22 mV, −21 mV, −20 mV, −19 mV, −18 mV, −17 mV, −16 mV, −15 mV, −14 mV, −13 mV, −12 mV, −11 mV or −10 mV in different buffers at various pHs. In other embodiments, the zeta potential are greater than −40 mV, −39 mV, −38 mV, −37 mV, −36 mV, −35 mV, −34 mV, −33 mV, −32 mV, −31 mV, −30 mV, −29 mV, −28 mV, −27 mV, −26 mV, −25 mV, −24 mV, −23 mV, −22 mV, −21 mV, −20 mV, −19 mV, −18 mV, −17 mV, −16 mV, −15 mV, −14 mV, −13 mV, −12 mV, −11 mV or −10 mV in different buffers at various pHs. In other embodiments, the zeta potential are less than −40 mV, −39 mV, −38 mV, −37 mV, −36 mV, −35 mV, −34 mV, −33 mV, −32 mV, −31 mV, −30 mV, −29 mV, −28 mV, −27 mV, −26 mV, −25 mV, −24 mV, −23 mV, −22 mV, −21 mV, −20 mV, −19 mV, −18 mV, −17 mV, −16 mV, −15 mV, −14 mV, −13 mV, −12 mV, −11 mV or −10 mV in different buffers at various pHs. In other embodiments, the zeta potential are about −40 mV, −39 mV, −38 mV, −37 mV, −36 mV, −35 mV, −34 mV, −33 mV, −32 mV, −31 mV, −30 mV, −29 mV, −28 mV, −27 mV, −26 mV, −25 mV, −24 mV, −23 mV, −22 mV, −21 mV, −20 mV, −19 mV, −18 mV, −17 mV, −16 mV, −15 mV, −14 mV, −13 mV, −12 mV, −11 mV or −10 mV in different buffers at various pHs.

Hybrid nanoparticles may have a given mass which differs based on the number of polymers in each hybrid nanoparticle. In some aspects, hybrid nanoparticles comprising a single semiconducting polymer may have a mass of 200 kDa in an exemplary case. In other embodiments, hybrid nanoparticles may have a mass of 500 kDakDa, 450 kDa, 400 kDa, 350 kDa, 300 kDa, 275 kDa, 250 kDa, 225 kDa, 200 kDa, 175 kDa, 150 kDa, 125 kDa, 100 kDa, 90 kDa, 80 kDa, 70 kDa, 60 kDa, 50 kDa, 40 kDa, 30 kDa, 20 kDa, 10 or 5 kDa. In other embodiments, hybrid nanoparticles may have a mass of greater than 500 kDa, 450 kDa, 400 kDa, 350 kDa, 300 kDa, 275 kDa, 250 kDa, 225 kDa, 200 kDa, 175 kDa, 150 kDa, 125 kDa, 100 kDa, 90 kDa, 80 kDa, 70 kDa, 60 kDa, 50 kDa, 40 kDa, 30 kDa, 20 kDa, 10 or 5 kDa. In other embodiments, hybrid nanoparticles may have a mass of less than 500 kDa, 450 kDa, 400 kDa, 350 kDa, 300 kDa, 275 kDa, 250 kDa, 225 kDa, 200 kDa, 175 kDa, 150 kDa, 125 kDa, 100 kDa, 90 kDa, 80 kDa, 70 kDa, 60 kDa, 50 kDa, 40 kDa, 30 kDa, 20 kDa, 10 or 5 kDa. In other embodiments, hybrid nanoparticles may have a mass of about 500 kDa, 450 kDa, 400 kDa, 350 kDa, 300 kDa, 275 kDa, 250 kDa, 225 kDa, 200 kDa, 175 kDa, 150 kDa, 125 kDa, 100 kDa, 90 kDa, 80 kDa, 70 kDa, 60 kDa, 50 kDa, 40 kDa, 30 kDa, 20 kDa, 10 or 5 kDa.

Hybrid nanoparticles may have a large intensity dependence on the polarization of light used for excitation. In some aspects, the polarization of light for excitation can be determined using $\lambda/2$ waveplates. For example, $I_\parallel:I_\perp$ excitation polarization ratio of intensities of 100:1, are measured. In some aspects, the ratio of intensities are 90:1, 80:1, 70:1, 60:1, 50:1, 40:1, 30:1, 20:1, 10:1 or 5:1. For example, hybrid nanoparticles are adsorbed to the surface of a glass channel, in some aspects, a cleaned, APTES-coated glass channel. In various aspects the channel are filled, for example, with water.

In various aspects, more than one method can be used with polarization determination. In some aspects, a method may include fixed excitation polarization while the polymer hybrid nanoparticle sample can be manually rotated, for example, using a rotation stage. In some aspects, the intensity of emission measured in $I_\parallel$ and $I_\perp$ channels as the stage rotated are anti-correlated. In other embodiments, the intensity of emission measured in $I_\parallel$ and $I_\perp$ channels as the stage rotated are correlated. In other embodiments, the intensity of emission measured in $I_\parallel$ and $I_\perp$ channels as the stage rotated may not be anti-correlated. In other embodiments, the intensity of emission measured in $I_\parallel$ and $I_\perp$ channels as the stage rotated are anti-correlated. In some aspects, the orientation of the emission dipole of each polymer hybrid nanoparticle is random. In another case, the method may include placement of a λ/2 waveplate in a rotating mount in the excitation path. In this case, the rotating mount can be moved while the sample remains stationary.

In certain aspects, the critical dimension is 20 nm or less. In further aspects, the critical dimension is 1 nm to 100 nm, 1 nm to 75 nm, 1 nm to 50 nm, 5 nm to 100 nm, 5 nm to 75 nm, 5 nm to 50 nm, 5 nm to 40 nm, 5 nm to 30 nm, 5 nm to 20 nm, 10 nm to 100 nm, 10 nm to 75 nm, 10 nm to 50 nm, 10 nm to 40 nm, 10 nm to 30 nm, or 10 nm to 20 nm. In various aspects, the critical dimension is a hydrodynamic diameter.

In some aspects, the polarization-sensitive nanoparticle is formed using nanoprecipitation.

In some aspects, the polarization-sensitive nanoparticles are fluorescent. In further aspects, the polarization-sensitive nanoparticle is capable of emitting polarized light when illuminated with polarized light.

In various aspects, the polarization-sensitive nanoparticle is fluorescence anisotropic. In some aspects, the polarization-sensitive nanoparticle has a fluorescence anisotropy of 0.01 to 1.00, 0.01 to 0.90, 0.01 to 0.80, 0.01 to 0.07, 0.02 to 1.00, 0.02 to 0.90, 0.02 to 0.80, 0.02 to 0.70, 0.03 to 1.00, 0.03 to 0.90, 0.03 to 0.80, 0.03 to 0.70, 0.05 to 1.00, 0.05 to 0.90, 0.05 to 0.80, 0.05 to 0.70, 0.10 to 1.00, 0.10 to 0.90, 0.10 to 0.80, 0.10 to 0.70, 0.20 to 1.00, 0.20 to 0.90, 0.20 to 0.80, 0.20 to 0.70, 0.50 to 1.00, 0.50 to 0.90, 0.50 to 0.80, 0.50 to 0.70, 0.60 to 1.00, 0.60 to 0.90, 0.60 to 0.80, or 0.60 to 0.70.

In some aspects, the polarization-sensitive nanoparticles have a fluorescence emission peak in the range of 400 nm to 900 nm, a fluorescence emission peak in the range of 500 nm to 600 nm, a fluorescence emission peak in the range of 600 nm to 700 nm, or a fluorescence emission peak in the range of 700 nm to 800 nm.

In certain aspects, the polarization-sensitive nanoparticle has a FWHM of the fluorescence emission peak of less than 100 nm, a FWHM of the fluorescence emission peak of less than 90 nm, a FWHM of the fluorescence emission peak of less than 80 nm, a FWHM of the fluorescence emission peak of less than 70 nm, a FWHM of the fluorescence emission peak of less than 60 nm, a FWHM of the fluorescence emission peak of less than 50 nm, a FWHM of the fluorescence emission peak of less than 40 nm, a FWHM of the fluorescence emission peak of less than 30 nm, a FWHM of the fluorescence emission peak of less than 20 nm, a FWHM of the fluorescence emission peak of less than 15 nm, a FWHM of the fluorescence emission peak of less than 10 nm, or a FWHM of the fluorescence emission peak of less than 5 nm.

In some aspects, the polarization-sensitive nanoparticle has a quantum yield of 0.10 to 1.00, the polarization-sensitive nanoparticle has a quantum yield of 0.10 to 0.90, the polarization-sensitive nanoparticle has a quantum yield of 0.10 to 0.75, the polarization-sensitive nanoparticle has a quantum yield of 0.10 to 0.50, the polarization-sensitive nanoparticle has a quantum yield of 0.25 to 1.00, the polarization-sensitive nanoparticle has a quantum yield of 0.25 to 0.90, the polarization-sensitive nanoparticle has a quantum yield of 0.25 to 0.75, the polarization-sensitive nanoparticle has a quantum yield of 0.25 to 0.50, the polarization-sensitive nanoparticle has a quantum yield of 0.50 to 1.00, the polarization-sensitive nanoparticle has a quantum yield of 0.50 to 0.90, the polarization-sensitive nanoparticle has a quantum yield of 0.50 to 0.75, the polarization-sensitive nanoparticle has a quantum yield of greater than 0.25, the polarization-sensitive nanoparticle has a quantum yield of greater than 0.50, the polarization-sensitive nanoparticle has a quantum yield of greater than 0.75, or the polarization-sensitive nanoparticle has a quantum yield of greater than 0.90.

In some aspects, the polarization-sensitive nanoparticle comprises one fluorescent polymer chain per polarization-sensitive nanoparticle. In further aspects, the polarization-sensitive nanoparticles comprise a plurality of fluorescent polymer chains per polarization-sensitive nanoparticle.

In some aspects, the first matrix polymer and the second matrix polymer together comprise a matrix. In certain aspects, the chromophoric polymer is immobilized within the matrix. In certain aspects, the mass ratio of the chromophoric polymer to the matrix is 0.01 to 0.50, the mass ratio of the chromophoric polymer to the matrix is 0.01 to 0.40, the mass ratio of the chromophoric polymer to the matrix is 0.01 to 0.35, the mass ratio of the chromophoric polymer to the matrix is 0.01 to 0.30, the mass ratio of the chromophoric polymer to the matrix is 0.01 to 0.25, the mass ratio of the chromophoric polymer to the matrix is 0.01 to 0.20, the mass ratio of the chromophoric polymer to the matrix is 0.01 to 0.15, the mass ratio of the chromophoric polymer to the matrix is 0.01 to 0.10, the mass ratio of the chromophoric polymer to the matrix is 0.01 to 0.05, the mass ratio of the chromophoric polymer to the matrix is 0.02 to 0.50, the mass ratio of the chromophoric polymer to the matrix is 0.02 to 0.40, the mass ratio of the chromophoric polymer to the matrix is 0.02 to 0.35, the mass ratio of the chromophoric polymer to the matrix is 0.02 to 0.30, the mass ratio of the chromophoric polymer to the matrix is 0.02 to 0.25, the mass ratio of the chromophoric polymer to the matrix is 0.02 to 0.20, the mass ratio of the chromophoric polymer to the matrix is 0.02 to 0.15, the mass ratio of the chromophoric polymer to the matrix is 0.02 to 0.10, the mass ratio of the chromophoric polymer to the matrix is 0.02 to 0.05, the mass ratio of the chromophoric polymer to the matrix is 0.03 to 0.50, the mass ratio of the chromophoric polymer to the matrix is 0.03 to 0.40, the mass ratio of the chromophoric polymer to the matrix is 0.03 to 0.35, the mass ratio of the chromophoric polymer to the matrix is 0.03 to 0.30, the mass ratio of the chromophoric polymer to the matrix is 0.03 to 0.25, the mass ratio of the chromophoric polymer to the matrix is 0.03 to 0.20, the mass ratio of the chromophoric polymer to the matrix is 0.03 to 0.15, the mass ratio of the chromophoric polymer to the matrix is 0.03 to 0.10, the mass ratio of the chromophoric polymer to the matrix is 0.03 to 0.05, the mass ratio of the chromophoric polymer to the matrix is 0.04 to 0.50, the mass ratio of the chromophoric polymer to the matrix is 0.04 to 0.40, the mass ratio of the chromophoric polymer to the matrix is 0.04 to 0.35, the mass ratio of the chromophoric polymer to the matrix is 0.04 to 0.30, the mass ratio of the chromophoric polymer to the matrix is 0.04 to 0.25, the mass ratio of the chromophoric polymer to the matrix is 0.04 to 0.20, the mass ratio of the chromophoric polymer to the matrix is 0.04 to 0.15, the mass ratio of the chromophoric polymer to the matrix is 0.04 to 0.10, the mass ratio of the chromophoric polymer to the matrix is 0.04 to 0.05, the mass ratio of the chromophoric polymer to the matrix is 0.05 to 0.50, the mass ratio of the chromophoric polymer to the matrix is 0.05 to 0.40, the mass ratio of the chromophoric polymer to the matrix is 0.05 to 0.35, the mass ratio of the chromophoric polymer to the matrix is 0.05 to 0.30, the mass ratio of the chromophoric polymer to the matrix is 0.05 to 0.25, the mass ratio of the chromophoric polymer to the matrix is 0.05 to 0.20, the mass ratio of the chromophoric polymer to the matrix is 0.05 to 0.15, the mass ratio of the chromophoric polymer to the matrix is 0.05 to 0.10, or the mass ratio of the chromophoric polymer to the matrix is 0.05 to 0.05.

Applications

Chromophoric polarization-sensitive nanoparticles are useful for many detection and/or imaging applications. The detection and/or imaging applications may include single-cell labeling, multi-cell labeling, tissue labeling, organ labeling, in vitro labeling, and in vivo labeling. The detection and/or imaging of cells may include molecules expressed by the cells, such as, extracellular molecules or intracellular molecules. The detection and/or imaging may include molecules attached to the cells such as proteins, sugars, particulates.

In various aspects, the present disclosure provides particles comprising a polarization-sensitive nanoparticle of the present disclosure, wherein the particle is a quantum dot, a gold nanoparticle or an iron nanoparticle.

In various aspects, the present disclosure provides compositions comprising a plurality of the polarization-sensitive nanoparticles of the present disclosure in a solution, wherein the composition is a monodispersion. In some aspects, the solution is aqueous.

In various aspects, the present disclosure provides methods of analyzing a target, the method comprising binding any one of the polarization-sensitive nanoparticles of the present disclosure to the target; illuminating the nanoparticle with electromagnetic radiation sufficient to produce a florescence signal; and detecting the fluorescence signal.

In some aspects, the electromagnetic radiation is polarized.

In various aspects, the present disclosure provides methods of analyzing a target, the method comprising binding any one of the polarization-sensitive nanoparticles of the present disclosure to the target; illuminating the nanoparticle with polarized electromagnetic radiation sufficient to produce a florescence signal; and detecting the fluorescence signal.

In some aspects, the methods further comprise detecting a change in the fluorescence signal while analyzing the target. In some aspects, the methods further comprise detecting the position of the target from the fluorescence signal. In some aspects, the methods further comprise detecting the presence or absence of the target from the presence or absence of a fluorescence signal. In some aspects, the methods further comprise In some aspects, the methods further comprise detecting the orientation of the target from the change in the fluorescence signal. In some aspects, the methods further comprise imaging a target. In some aspects, the methods further comprise detecting a change in position of the polarization-sensitive nanoparticle from the change in the polarization-sensitive nanoparticle's fluorescence signal. In some aspects, the methods further comprise determining the orientation of the target from the change in position of the polarization-sensitive nanoparticle.

In certain aspects, the polarization-sensitive nanoparticle and the target are both in a solution. In further aspects, the solution is aqueous. In some aspects, a plurality of nanoparticles are bound to the target.

In further aspects, the target is a biomolecule. In some aspects, the target is a biomarker. In further aspects, the target is selected from an antibody, an antigen, a cell, a nucleic acid, an enzyme, a substrate for an enzyme, a protein, a lipid, a carbohydrate, a therapeutic agent, or a combination thereof.

In some aspects, a plurality of targets are simultaneously analyzed in parallel.

Certain embodiments of the present disclosure relate to chromophoric polarization-sensitive nanoparticles and their biomolecular conjugates for a variety of applications, including but not limited to flow cytometry, fluorescence activated sorting, immunofluorescence, immunohistochemistry, fluorescence multiplexing, single molecule imaging, single particle tracking, protein folding, protein rotational dynamics, DNA and gene analysis, protein analysis, metabolite analysis, lipid analysis, FRET based sensors, high throughput screening, cellular imaging, in vivo imaging, bioorthogonal labeling, click reactions, fluorescence-based biological assays such as immunoassays and enzyme-based assays (e.g., ELISA), western blot, and a variety of fluorescence techniques in biological assays and measurements.

The chromophoric polarization-sensitive nanoparticles described herein are used in a wide variety of applications including, medical diagnostics, medical prognostics, biological research, and water and soil testing. Similarly, the chromophoric polarization-sensitive nanoparticles are used to detect a wide variety of analytes, such as cells, microbes, bacteria, viruses, proteins, peptides, carbohydrates, nucleic acids or portions thereof.

This disclosure provides methods for using chromophoric polarization-sensitive nanoparticles to label and detect analytes within a sample such as a mixed sample. In some aspects, the sample can be a fluid sample. The fluid sample can be a biological fluid sample, for example a blood sample, plasma sample, saliva sample, urine sample, lymph sample, or spinal fluid sample. In some aspects, the sample can be an environmental fluid sample, for example from a lake, river, ocean, pond, stream, spring, marsh, or reservoir. In other embodiments, the sample are a water sample, for example from a desalinization plant, water treatment plant, reservoir, spring, stream, glacial water flow, water tower, or other water source that are contemplated as a source of potable water.

In some aspects, a molecule expressed by an analyte such as a cell is detected with the chromophoric polarization-sensitive nanoparticles provided herein. For example, cells are contacted with an agent (e.g., antibody) that recognizes a molecule (e.g, cell surface marker, intracellular marker, etc.). In some aspects provided herein, the agent is modified so that it can bind to or connect to a binding partner that is connected to a chromophoric polymer hybrid nanoparticle. For example, the agent can be modified by conjugating the agent to biotin or streptavidin. In some specific examples, the agent is conjugated to biotin so that the agent is capable of recognizing a streptavidin molecule that is conjugated to a chromophoric polymer hybrid nanoparticle. Such chromophoric polarization-sensitive nanoparticles are useful in a wide variety of applications, including cellular imaging studies or a fluid sample containing an analyte.

The analyte in the fluid sample is a cell, protein, protein complex, nucleic acid, nucleoprotein complex, carbohydrate, metabolite, catabolite, and the like. In some aspects, the analyte is a cell. Non-limiting examples of cells include: mammalian cells, human cells, non-human mammalian cells, eukaryotic cells, prokaryotic cells, animal cells, insect cells, bacteria cells, microbial cells, fungal cells, amphibian cells and fish cells. The cells can originate from a variety of tissues including but not limited to: neural crest tissue, endodermal tissue, ectodermal tissue, mesodermal tissue, and mesenchymal tissue. Cell types may include but are not limited to: breast cells, brain cells, neural cells, pancreatic cells, liver cells, gall bladder cells, gastrointestinal cells, stomach cells, kidney cells, cells of the reproductive system, heart cells, skin cells, colon cells, urethral cells, endodermal cells, muscle cells, fibroblasts, adipocytes, tumor cells, cancer cells, virally-infected cells, bacterial infected cells, stem cells, dividing cells, apoptotic cells, necrotic cells, blood cells, white blood cells, and stromal cells.

The sample is contacted with an agent suitable for labeling the analyte. In some aspects, the agent are an antibody, an antibody fragment, a peptide, a Fab fragment, an Fc fragment, a light chain, a heavy chain, an immunoglobin, or an immunoglobin fragment. In some aspects, the agent is a peptide or a small molecule. In some aspects, the agent is modified. The modification to the agent may include a chemical modification, an enzymatic modification, linkage of a hydrophilic functional group, a hydrophobic functional group and/or a reactive moiety.

The methods provided herein may include incubation periods. For example, the chromophoric polarization-sensitive nanoparticles are incubated with the agents (such as antibodies); the agents (including agents conjugated to chromophoric polarization-sensitive nanoparticles) are incubated with the analytes (e.g., cells). The incubation period may last for a length of time that is less than or equal to 100 hours, 75 hours, 60 hours, 50 hours, 24 hours, 20 hours, 15 hours, 10 hours, 5 hours, 3 hours, 2 hours, or 1 hour. In some aspects, the incubation period is greater than 5 minutes, 10 minutes, 30 minutes, 1 hour, 2 hours, 5 hours, 10 hours, 24 hours, 30 hours, 50 hours, 60 hours, 75 hours or 100 hours. In some aspects, the incubation period is 5 minutes, 10 minutes, 30 minutes, 1 hour, 2 hours, 5 hours, 10 hours, 24 hours, 30 hours, 50 hours, 60 hours, 75 hours or 100 hours. In some aspects, the incubation period is about 5 minutes, 10 minutes, 30 minutes, 1 hour, 2 hours, 5 hours, 10 hours, 24 hours, 30 hours, 50 hours, 60 hours, 75 hours or 100 hours.

In some aspects, the cell may express an antigen, for example, that are detected by the agent. For example, an agent can be an antibody. The antibody can be EpCAM which is expressed on some cancerous cells, including MCF-7 cells. Other examples of antibodies that are conjugated to a chromophoric polymer hybrid nanoparticle include but are not limited to the pan-cytokeratin antibody A45B/B3, AE1/AE3, or CAM5.2 (pan-cytokeratin antibodies that recognize Cytokeratin 8 (CK8), Cytokeratin 18 (CK18), or Cytokeratin 19 (CK19) and ones against: breast cancer antigen NY-BR-1 (also known as B726P, ANKRD30A, Ankyrin repeat domain 30A); B305D isoform A or C (B305D-A ro B305D-C; also known as antigen B305D); Hermes antigen (also known as Antigen CD44, PGP1); E-cadherin (also known as Uvomorulin, Cadherin-1, CDH1); Carcino-embryonic antigen (CEA; also known as CEACAMS or Carcino-embryonic antigen-related cell adhesion molecule 5); β-Human chorionic gonahybrid nanoparticleophin (β-HCG; also known as CGB, chronic gonahybrid nanoparticlerophin, β polypeptide); Cathepsin-D (also known as CTSD); Neuropeptide Y receptor Y3 (also known as NPY3R; Lipopolysaccharide-associated protein3, LAP3, Fusion; chemokine (CXC motif, receptor 4); CXCR4); Oncogene ERBB1 (also known as c-erbB-1, Epidermal growth factor receptor, EGFR); Her-2 Neu (also known as c-erbB-2 or ERBB2); GABA receptor A, pi ($\pi$) polypeptide (also known as GABARAP, GABA-A receptor, pi ($\pi$) polypeptide (GABA A($\pi$), γ-Aminobutyric acid type A receptor pi ($\pi$) subunit), or GABRP); ppGalNac-T(6) (also known as β-1-4-N-acetyl-galactosaminyl-transferase 6, GalNActransferase 6, GalNAcT6, UDP-N-acetyl-d-galactosamine:polypeptide N-acetylgalactosaminyltransferase 6, or GALNT6); CK7 (also known as Cytokeratin 7, Sarcolectin, SCL, Keratin 7, or KRT7); CK8 (also known as Cytokeratin 8, Keratin 8, or KRT8); CK18 (also known as Cytokeratin 18, Keratin 18, or KRT18); CK19 (also known as Cytokeratin 19, Keratin 19, or KRT19); CK20 (also known as Cytokeratin 20, Keratin 20, or KRT20); Mage (also known as Melanoma antigen family A subtypes or MAGE-A subtypes); Mage3 (also known as Melanoma antigen family A 3, or MAGA3); Hepatocyte growth factor receptor (also known as HGFR, Renal cell carninoma papillary 2, RCC P2, Protooncogene met, or MET); Mucin-1 (also known as MUC1, Carcinoma Antigen 15.3, (CA15.3), Carcinoma Antigen 27.29 (CA 27.29); CD227 antigen, Episialin, Epithelial Membrane Antigen (EMA), Polymorphic Epithelial Mucin (PEM), Peanut-reactive urinary mucin (PUM), Tumor-associated glycoprotein 12 (TAG12)); Gross Cystic Disease Fluid Protein (also known as GCDFP-15, Prolactin-induced protein, PIP); Urokinase receptor (also known as uPR, CD87 antigen, Plasminogen activator receptor urokinase-type, PLAUR); PTHrP (parathyrold hormone-related proteins; also known as PTHLH); BS106 (also known as B511S, small breast epithelial mucin, or SBEM); Prostatein-like Lipophilin B (LPB, LPHB; also known as Antigen BU101, Secretoglobin family 1-D member 2, SCGB1-D2); Mammaglobin 2 (MGB2; also known as Mammaglobin B, MGBB, Lacryglobin (LGB) Lipophilin C (LPC, LPHC), Secretoglobin family 2A member 1, or SCGB2A1); Mammaglobin (MGB; also known as Mammaglobin 1, MGB1, Mammaglobin A, MGBA, Secretoglobin family 2A member 2, or SCGB2A2); Mammary serine protease inhibitor (Maspin, also known as Serine (or cystein) proteinase inhibitor clade B (ovalbumin) member 5, or SERPINB5); Prostate epithelium-specific Ets transcription factor (PDEF; also known as Sterile alpha motif pointed domain-containing ets transcription factor, or SPDEF); Tumor-associated calcium signal transducer 1 (also known as Colorectal carcinoma antigen CO17-1A, Epithelial Glycoprotein 2 (EGP2), Epithelial glycoprotein 40 kDa (EGP40), Epithelial Cell Adhesion Molecule (EpCAM), Epithelial-specific antigen (ESA), Gastrointestinal tumor-associated antigen 733-2 (GA733-2), KS1/4 antigen, Membrane component of chromosome 4 surface marker 1 (M4S1), MK-1 antigen, MIC18 antigen, TROP-1 antigen, or TACSTD1); Telomerase reverse transcriptase (also known as Telomerase catalytic subunit, or TERT); Trefoil Factor 1 (also known as Breast Cancer Estrogen-Inducible Sequence, BCEI, Gastrointestinal Trefoil Protein, GTF, pS2 protein, or TFF1); folate; or Trefoil Factor 3 (also known as Intestinal Trefoil Factor, ITF, p1.B; or TFF3).

In some aspects, a sample containing analytes are prepared for labeling. At any stage of a method provided herein, the analytes (e.g., cells) are incubated with a blocking buffer to prevent or reduce non-specific binding of the agent. In some aspects, non-specific binding are measured, e.g., by percentage, fold, change, of non-specific binding, relative to another compound. For example, the fold of non-specific binding can be less than 1 fold, 2 fold, 3 fold, 4 fold, 5 fold, 6 fold, 7 fold, 8 fold, 9 fold or 10 fold. For example, the fold of non-specific binding are 1 fold, 2 fold, 3 fold, 4 fold, 5 fold, 6 fold, 7 fold, 8 fold, 9 fold or 10 fold. For example, the fold of non-specific binding can be about 1 fold, 2 fold, 3 fold, 4 fold, 5 fold, 6 fold, 7 fold, 8 fold, 9 fold or 10 fold.

At any stage of a method provided herein, the analytes (e.g., cells) are washed with a suitable buffer solution. The cells are concentrated by any method known in the art, including but not limited to centrifugation or filtration. In some aspects, the analytes (e.g., cells) are not concentrated as part of a method provided herein. In some aspects, the method may include fixing the cells with a fixative. In other embodiments, the method may not include fixing the cells with a fixative. In some aspects, the method may include permeablizing the cells with an agent suitable for permeabilization. In other embodiments, preparation of the cells may not include permeablizing the cells with an agent suitable for permeabilization.

The present disclosure provides the use of chromophoric polarization-sensitive nanoparticles for the detection of proteins and peptides. In some aspects, the present disclosure relates to the use of bioconjugated chromophoric polarization-sensitive nanoparticles for use in Western blotting assays, including separation and detection of the proteins or peptides of interest. According to various embodiments of the present disclosure, the proteins or peptides are separated by chromatography, filtration, capillary electrophoresis, precipitation, liquid or other extraction methods, immunoprecipitation, or a combination thereof. In certain embodiments, other protein detection assays are performed using chromophoric polarization-sensitive nanoparticles, including, but not limited to, immunostaining, spectrophotometry, enzyme-based assays (e.g., ELISA), and combinations thereof.

The present disclosure can be used in association with any assay that includes the detection of a protein or peptide analyte using chromophoric polarization-sensitive nanoparticles. In various embodiments, the protein or peptide are separated from a mixture before detection. The present methods are used with an immunological method (e.g., an ELISA assay, an RIA assay, an ELI-Spot assay, a flow cytometry assay, an immunohistochemistry assay, a immunostaining, a Western blot analysis, and a protein chip assay), a physical method (e.g., one- or two-dimensional gel electrophoresis assays, a capillary electrophoresis assay, a FRET assay, a chromatographic assay, or a dye-detection assay, a spectrophotometry assay, a precipitation method), or a combination thereof.

In various embodiments, prior to detection using chromophoric polarization-sensitive nanoparticles of the present disclosure, proteins or peptides are separated by a chromatography method, a filtration method, a capillary electrophoresis method, a gel electrophoresis method, a liquid extraction method, a precipitation method, or an immunoprecipitation method. Further, the chromatography method can be reverse phase chromatography. In various embodiments, a plurality of assays can be performed in parallel to improve analysis throughput.

In various embodiments, the present disclosure provides methods for detecting proteins or peptides, the method comprising: separating the proteins or peptides from a mixture; contacting the separated proteins or peptides with a solution comprising a polymer hybrid nanoparticle conjugated to a biomolecule specific to at least some of the separated proteins or peptides; and detecting at least one signal from the polarization-sensitive nanoparticles, the at least one signal corresponding to the separated proteins or peptides. In some aspects, the present methods quantitate proteins or peptides.

In some aspects, the separating the proteins or peptides comprises a chromatography method, a filtration method, a capillary electrophoresis method, a gel electrophoresis method, a liquid extraction method, a precipitation method, an immunoprecipitation method, or a combination thereof.

In some aspects, the polymer hybrid nanoparticle comprises a polymer selected from a semiconducting polymer, a non-semiconducting polymer, or a combination thereof.

In some aspects, the polymer hybrid nanoparticle comprises a polymer selected from a poly((meth)acrylic acid)-based polymer, a polydiene-based polymer, a poly(ethylene oxide)-based polymer, a polyisobutylene-based polymer, a polystyrene-based polymer, a polysiloxane-based polymer, a poly(ferrocenyldimethylsilane)-based polymer, a poly(2-vinyl naphthalene)-based polymer, a poly(vinyl pyridine)-based polymer, a poly(N-methyl vinyl pyridinium iodide)-based polymer, or a poly(vinyl pyrrolidone)-based polymer.

In some aspects, the present disclosure provides for detection of proteins or peptides in conjunction with a Western blot assay. Western blotting is a protein analysis method in which proteins are separated by mass and/or length, typically using sodium dodecyl sulfate-polyacrylamide gel electrophoresis (SDS-PAGE), then transferred onto a membrane composed of, e.g., nitrocellulose or a fluoropolymer such as polyvinylidene fluoride (PVDF), and visualized using a labelling procedure. In the present disclosure, chromophoric polarization-sensitive nanoparticles are shown to provide detection of protein at quantities as low as 50 picograms using Western blot analysis (see e.g., Example 5).

In other embodiments, methods are provided for ultra-sensitive fluorescence imaging of molecules using chromophoric polarization-sensitive nanoparticles in a hybrid nanoparticle blot assay. In a hybrid nanoparticle blot assay, the proteins or peptides to be detected are not first separated. Instead, an un-separated sample is applied directly on a membrane as a hybrid nanoparticle and visualized using a labelling procedure. In the present disclosure, chromophoric polarization-sensitive nanoparticles are shown to provide detection of protein at quantities lower than two picograms using hybrid nanoparticle blot analysis.

Proteins or peptides are collected from a tissue, cell, or fluid sample by methods can include, but are not limited to, freezing and thawing, sonication, homogenization by high pressure, filtration, permeabilization, and centrifugation. In some aspects, a collected protein or peptide can also undergo one or more isolation or purification steps prior to analysis.

In some aspects, analyses can be performed on a sample that contains a heterogeneous mix of different proteins. In other embodiments, analyses can be performed on a purified protein.

In some aspects, a sample is separated prior to analysis, such as by gel electrophoresis or another method suitable for separating a sample. In some aspects, proteins or peptides are separated based on their mass and/or charge prior to analysis.

In some aspects, chromophoric polarization-sensitive nanoparticles are suspended in a liquid, and this liquid is brought into physical contact with a sample, the sample being either suspended in a second liquid or disposed on a surface. In some aspects, the sample is disposed on a surface which comprises a membrane.

In some aspects, chromophoric polarization-sensitive nanoparticles are disposed on a surface, and this surface is brought into physical contact with a sample, the sample being suspended in a liquid. In some aspects, the surface on which chromophoric polarization-sensitive nanoparticles are disposed comprises a membrane.

In some aspects, an immunoprecipitation assay is performed, in which chromophoric polarization-sensitive nanoparticles are disposed on a surface and brought into physical contact with a protein sample suspended in a liquid. According to this case, contact between the protein sample and the corresponding chromophoric polymer hybrid nanoparticle causes the protein to adhere to the surface via the binding chromophoric polymer hybrid nanoparticle.

In various embodiments, the presently described chromophoric polarization-sensitive nanoparticles will emit fluorescence when properly induced by an excitation source. In certain embodiments, the quantity of chromophoric polarization-sensitive nanoparticles present are determined and subsequently correlated with the quantity of a given analyte of interest, such as e.g., a protein of interest. Thus, the presently described methods utilize an excitation light source to induce chromophoric polymer hybrid nanoparticle fluorescence, which can then be measured and correlated with sample concentration. In various embodiments, electromagnetic radiation (e.g., infrared radiation, visible light, or ultraviolet radiation) is used to trigger electromagnetic emission from chromophoric polarization-sensitive nanoparticles, and the emitted signal are used to assess the amount of target molecule present in a sample. In some aspects, the source of electromagnetic radiation can comprise a laser, LED, lamp, spectral filter or multichroic mirror. In some aspects, the light excitation source can be a component of a gel imaging apparatus, a microscope, or other suitable apparatus. The chemical and physical properties of a given chromophoric polymer hybrid nanoparticle can be adjusted in order to tune the excitation and emission wavelengths, among other optical properties.

In some aspects, the peak wavelength of electromagnetic radiation that induces excitation of a chromophoric polymer hybrid nanoparticle is between about 200 nm and about 300 nm, about 250 nm and about 350 nm, about 300 nm and about 400 nm, about 350 nm and about 450 nm, between about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm. In some aspects more than one excitation spectrum can be experienced by a sample, such as in multiplex analyses.

In some aspects, the peak wavelength of electromagnetic radiation that induces excitation of a chromophoric polymer hybrid nanoparticle is between 200 nm and 300 nm, 250 nm and 350 nm, 300 nm and 400 nm, 350 nm and 450 nm, between 400 nm and 500 nm, 450 nm and 550 nm, 500 nm and 600 nm, 550 nm and 650 nm, 600 nm and 700 nm, 650 nm and 750 nm, 700 nm and 800 nm, 750 nm and 850 nm, 800 nm and 900 nm, 850 nm and 950 nm, or 900 nm and 1000 nm. In some aspects more than one excitation spectrum can be experienced by a sample, such as in multiplex analyses.

In some aspects, the peak wavelength of the detected signal is between about 200 nm and about 300 nm, about 250 nm and about 350 nm, about 300 nm and about 400 nm, about 350 nm and about 450 nm, between about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, about 900 nm and about 1000 nm, about 950 nm and about 1050 nm, about 1000 nm and about 1100 nm, about 1050 nm and about 1150 nm, about 1100 nm and about 1200 nm, about 1150 nm and about 1250 nm, or about 1200 nm and about 1300 nm.

In some aspects, the peak wavelength of the detected signal is between 200 nm and 300 nm, 250 nm and 350 nm, 300 nm and 400 nm, 350 nm and 450 nm, between 400 nm and 500 nm, 450 nm and 550 nm, 500 nm and 600 nm, 550 nm and 650 nm, 600 nm and 700 nm, 650 nm and 750 nm, 700 nm and 800 nm, 750 nm and 850 nm, 800 nm and 900 nm, 850 nm and 950 nm, 900 nm and 1000 nm, 950 nm and 1050 nm, 1000 nm and 1100 nm, 1050 nm and 1150 nm, 1100 nm and 1200 nm, 1150 nm and 1250 nm, or 1200 nm and 1300 nm.

In some aspects, the assay is sensitive enough to detect less than 500 picograms, less than 400 picograms, less than 300 picograms, less than 200 picograms, less than 100 picograms, less than 50 picograms, less than 40 picograms, less than 30 picograms, less than 20 picograms, less than 10 picograms, less than five picograms, less than four picograms, less than three picograms, less than two picograms, or less than one picogram of a target molecule, such as a protein.

In some aspects, the assay is sensitive enough to detect about 500 picograms, about 400 picograms, about 300 picograms, about 200 picograms, about 100 picograms, about 50 picograms, about 40 picograms, about 30 picograms, about 20 picograms, about 10 picograms, about five picograms, about four picograms, about three picograms, about two picograms, or about one picogram of a target molecule, such as a protein.

In some aspects, the assay is sensitive enough to detect 500 picograms, 400 picograms, 300 picograms, 200 picograms, 100 picograms, 50 picograms, 40 picograms, 30 picograms, 20 picograms, 10 picograms, five picograms, four picograms, three picograms, two picograms, or one picogram of a target molecule, such as a protein.

Among many advantages, such as improved detection sensitivity and photo-stability, the present disclosure includes methods that do not require any additional equipment or time compared to the conventional procedure with traditional fluorescent probes.

As used herein, "specificity" refers to a conjugated chromophoric polymer hybrid nanoparticle having greater binding affinity for its target than it has for other components it is in physical contact with. A conjugated chromophoric polymer hybrid nanoparticle is specific for its target if the equilibrium constant for the conjugated chromophoric polymer hybrid nanoparticle and its target is greater than the average of the equilibrium constants for the conjugated chromophoric polymer hybrid nanoparticle and the other components it is in physical contact with. Greater specificity indicates a greater binding affinity for the target relative to other components, and this yields improvements in detection sensitivity in assays for a target. Advantageously, the present methods exhibit very high specificity for the target molecules of the present disclosure, such as, e.g., proteins or peptides.

In some aspects, the use of conjugated chromophoric polarization-sensitive nanoparticles improves detection sensitivity because of the relatively low levels of non-specific adsorption to surfaces by those chromophoric polarization-sensitive nanoparticles, e.g., to membranes on which a sample is disposed. In certain embodiments, non-specific adsorption is minimized by using a blocking agent, which is any agent that blocks non-specific binding that is capable of interfering with the accurate detection of target proteins or peptides with chromophoric polarization-sensitive nanoparticles. For example, blocking agents advantageously block non-specific adsorption of chromophoric polarization-sensitive nanoparticles and/or biomolecules onto surfaces that the chromophoric polarization-sensitive nanoparticles and/or biomolecules can come into physical contact with.

In certain embodiments, the detecting comprises detecting picogram quantities of the separated proteins. In further embodiments, the detecting comprises detecting less than two picograms of the separated proteins. In certain embodiments, the method further comprises exciting the polymer hybrid nanoparticle with a source of electromagnetic radiation. In some aspects, the source of electromagnetic radiation comprises a laser, a lamp, an LED, or a combination thereof. In further embodiments, the electromagnetic radiation passes through a spectral filter, a multichroic mirror, or a combination thereof, before exciting the polymer hybrid nanoparticle.

In some aspects, the peak wavelength of electromagnetic radiation exciting the sample is between about 200 nm and about 300 nm, about 250 nm and about 350 nm, about 300 nm and about 400 nm, about 350 nm and about 450 nm, between about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm. In some aspects, two or more peak wavelengths of electromagnetic radiation excite the sample.

In some aspects, the peak wavelength of electromagnetic radiation exciting the sample is between 200 nm and 300 nm, 250 nm and 350 nm, 300 nm and 400 nm, 350 nm and 450 nm, between 400 nm and 500 nm, 450 nm and 550 nm, 500 nm and 600 nm, 550 nm and 650 nm, 600 nm and 700 nm, 650 nm and 750 nm, 700 nm and 800 nm, 750 nm and 850 nm, 800 nm and 900 nm, 850 nm and 950 nm, or 900 nm and 1000 nm.

The disclosure provides for methods that are used to detect analytes in a sample, particularly to detect a chromophoric polymer hybrid nanoparticle provided herein. The analytes are labeled with chromophoric polarization-sensitive nanoparticles; or, in some aspects, the analytes are labeled with a combination of chromophoric polarization-sensitive nanoparticles and other labeling agents such as fluorophores. In some aspects, labeled analytes from a sample are analyzed for the presence of a chromophoric polymer hybrid nanoparticle. In some aspects, a flow cytometer are used to detect chromophoric polarization-sensitive nanoparticles (e.g., FACS Canto II). In some aspects, the flow cytometer are equipped with a laser (e.g., 405 nm). In some aspects, the chromophoric polarization-sensitive nanoparticles are detected using a laser (e.g., 405 nm) and detection channels for fluorescence emission with filters (e.g., 502 nm long-pass and a 510/50 nm band-pass filter).

In some aspects, the scattered light and fluorescence emission are detected by photomultiplier tube arrays. In some aspects, the data acquired from flow cytometry experiments are analyzed using software (e.g., FlowJo).

In some aspects, fluorescence microscopy can be used to detect the chromophoric polarization-sensitive nanoparticles. For example, a fluorescent microscope equipped with a camera can be used to image cells. The microscope can be a confocal microscope (e.g., Zeiss LSM 510). The chromophoric polarization-sensitive nanoparticles are excited by laser (e.g., a 405-nm diode laser or a 488-nm argon laser). In some aspects, cells are imaged such as by using glass-bottomed culture dishes.

While preferred embodiments of the present disclosure have been shown and described herein, it is to be understood that the disclosure is not limited to the particular embodiments of the disclosure described below, as variations of the particular embodiments are made and still fall within the scope of the appended claims. It is also to be understood that the terminology employed is for the purpose of describing particular embodiments of the disclosure, and is not intended to be limiting. Instead, the scope of the present disclosure is established by the appended claims. In this specification and the appended claims, the singular forms "a," "an" and "the" include plural reference unless the context clearly dictates otherwise.

The particulars shown herein are by way of example and for purposes of illustrative discussion of the preferred embodiments of the present disclosure only and are presented in the cause of providing what is believed to be the most useful and readily understood description of the principles and conceptual embodiments of various embodiments of the disclosure. In this regard, no attempt is made to show structural details of the disclosure in more detail than is necessary for the fundamental understanding of the disclosure, the description taken with the drawings and/or examples making apparent to those skilled in the art how the several forms of the disclosure are embodied in practice.

EXAMPLES

The following examples are put forth so as to provide those of ordinary skill in the art with a complete disclosure and description of how to make and use the present disclosure and are not intended to limit the scope of what is regarded as the disclosure nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Preparation and Use of Hybrid Semiconducting Polymer Nanoparticles

This example describes the preparation and use of hybrid semiconducting polymer nanoparticles that distinguish movement of a portion of protein from and/or towards a different portion of the same protein.

Materials

Poly[(9,9-dioctylfluorenyl-2,7-diyl)-alt-co-(1,4-benzo-(2,1',3)-thiadiazole)] (PFBT, 10 kDa MW, polydispersity index (PDI) 2.3) was purchased from American Dye Source, Inc. (Quebec, Canada). Polystyrene-graft-poly(ethylene oxide) functionalized with carboxyl groups (PS-PEG-COOH, main chain MW 8,500, graft chain MW 1,200, total chain MW 21,700, PDI 1.25) was purchased from Polymer Source Inc (Quebec, Canada). Dimethyl sulfoxide (DMSO), casein, adenosine 5'-triphosphate magnesium salt (MgATP), 4-(2-Hydroxyethyl)piperazine-1-ethanesulfonic acid, N-(2-Hydroxyethyl)piperazine-N'-(2-ethanesulfonic acid) (HEPES), (3-aminopropyl)triethoxysilane (APTES), poly(ethylene glycol) (PEG), and tetrahydrofuran (THF) were purchased from Sigma-Aldrich (St. Louis, Mo.). 1-ethyl-3-(3-dimethylaminopropyl)carbodiimide) was purchased from Invitrogen (Carlsbad, Calif.). 30% Hydrogen peroxide was purchased from JT Baker (Mansfield, Mass.). Ultrapure water (Milli-Q) was produced by a Milli-Q water production unit; this production unit and ammonium hydroxide were purchased from EMD Millipore (Billerica, Mass.). Tubulin protein, biotinylated tubulin, fluorescent HiLyte 488 tubulin, paclitaxel ("Taxol"), guanosine-5'-triphosphate (GTP), and General Tubulin Buffer (GTB) were purchased from Cytoskeleton Inc. (Denver, Colo.). Full length kinesin motor proteins of two varieties, fruit fly kinesin and *Escherichia coli*, were kindly provided by the Wordeman lab at the University of Washington. All chemicals were used as-is unless stated otherwise.

P70 Polymer Synthesis

The copolymer was synthesized by grafting hydrophobic dodecylamine onto the hydrophilic poly(isobutylene-alt-maleic anhydride) (Mw~6,000) backbone through spontaneous amide linkage, which converts one maleic anhydride into one corresponding amide and one free carboxylic acid. 0.5 g (0.083 mmol) of poly(isobutylene-alt-maleic anhydride) was dispersed in 20 mL of anhydrous THF in a 100-mL round flask. 0.43 g (2.32 mmol) dodecylamine dissolved in 40 mL of anhydrous THF was quickly injected to the polymer solution and kept at 60° C. with vigorous stirring. After 3 hours, the reaction mixture was concentrated to one third of the original volume under a reduced pressure. The concentrated solution was further refluxed overnight at 60° C. The solvent was then slowly evaporated until the polymer was completely dry to obtain a pale yellow solid. The final product yield was ~0.88 g, 95%. $^1$H NMR (500 MHz, CDCl$_3$): δ=4.368-4.339 (br s, 2H), 3.74 (s, 2H), 2.516-2.483 (br s, 2H), 2.282-2.251 (br s, 2H), 1.848 (s, 2H), 1.264 (s, 22H), 0.879 (s, 9H).

Semiconducting Polymer Hybrid Nanoparticle Formation

Polarization-sensitive nanoparticles were formed by a nanoprecipitation technique. THF solutions with 20 µL of 10 mg/mL P70, 25 µL of 10 mg/mL PS-PEG-COOH, and 1 µL of 10 mg/mL PFBT were mixed with 5 mL of THF and the resulting solution was sonicated for 1 minute. Following sonication, the THF solution was quickly added to 10 mL of Milli-Q water under high sonication power. The polymer is insoluble in water and quickly formed polarization-sensitive nanoparticles. The THF was then removed by heating the solution to 85° C. and bubbling nitrogen gas through the solution for 2 hours. Following removal of THF, the hybrid nanoparticles were filtered through a 0.2-µm filter.

Preparation of Polarization-Sensitive Nanoparticles

Figure 2:
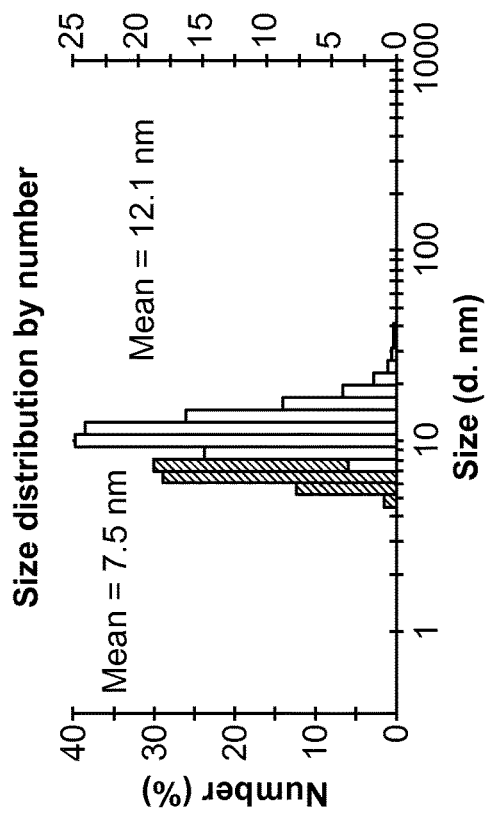
FIG. 2 depicts the bulk fluorescence and properties of polarization-sensitive nanoparticles according to an aspect of the present disclosure, including (A) the absorption and emission epectra of polymer nanoparticles, (B) the number-averaged nanoparticle hydrodynamic diameters before functionalization (hashed) and after functionalization (unhashed).
Figure 2:
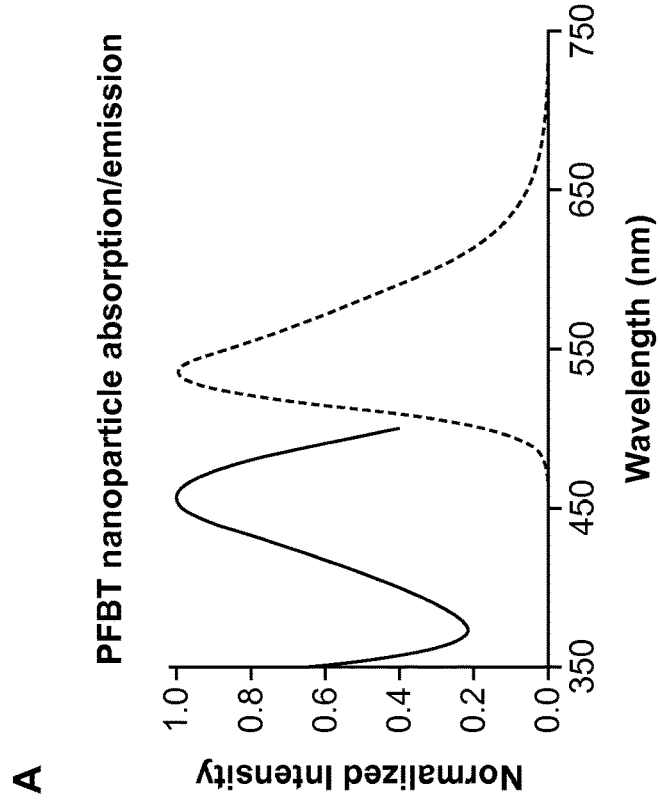
Figure 6:
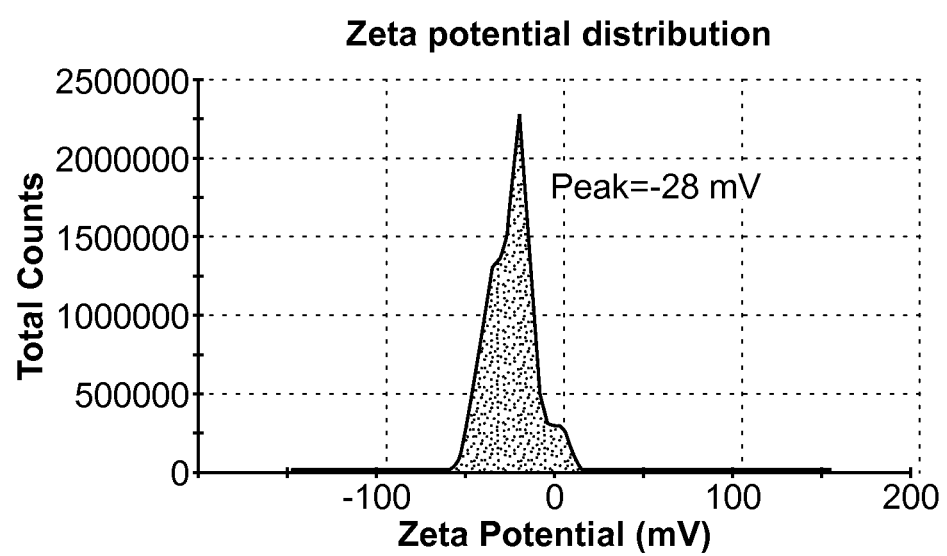
FIG. 6 demonstrates the zeta potential of bioconjugated polarization-sensitive nanoparticles according to an aspect of the present disclosure.

FIG. 1 shows the strategy used for preparing polarization-sensitive fluorescent hybrid nanoparticles. Nanoprecipitation of the hydrophobic fluorescent polymer Poly[(9,9-dioctylfluorenyl-2,7-diyl)-alt-co-(1,4-benzo-(2,1',3)-thiadiazole)] (PFBT), along with matrix polymers P70 (see FIG. 1 for chemical formula) and polystyrene-graft-poly(ethylene oxide) functionalized with carboxyl groups (PS-PEG-COOH), formed small fluorescent hybrid nanoparticles with a mean diameter of 7.5 nm and a peak width of 1.5 nm. The absorption/emission spectra of the hybrid nanoparticles are shown in FIG. 2A, part (A) depicts the absorption and emission spectra of polarization-sensitive nanoparticles and part (B) shows the number-averaged hybrid nanoparticle hydrodynamic diameter before functionalization. The hybrid nanoparticles were functionalized with streptavidin to facilitate binding to biomolecules. FIG. 6 shows the hybrid nanoparticles had a relatively low zeta potential of −28 mV in 20 mM HEPES buffer at pH 7.2. To prevent aggregation and nonspecific adsorption, the hybrid nanoparticles were also functionalized with polyethylene glycol (PEG). Dynamic light scattering (DLS) measurements showed an increase in average polymer hybrid nanoparticle hydrodynamic diameter before and after bioconjugation from 7.46 nm to 12.07 nm (FIG. 2B) with peak FWHM of 1.46 and 3.72 nm, respectively. The resulting functionalized hybrid nanoparticles were found to be quite monodisperse and their size measurement remained stable for months at 4° C.

Figure 7:
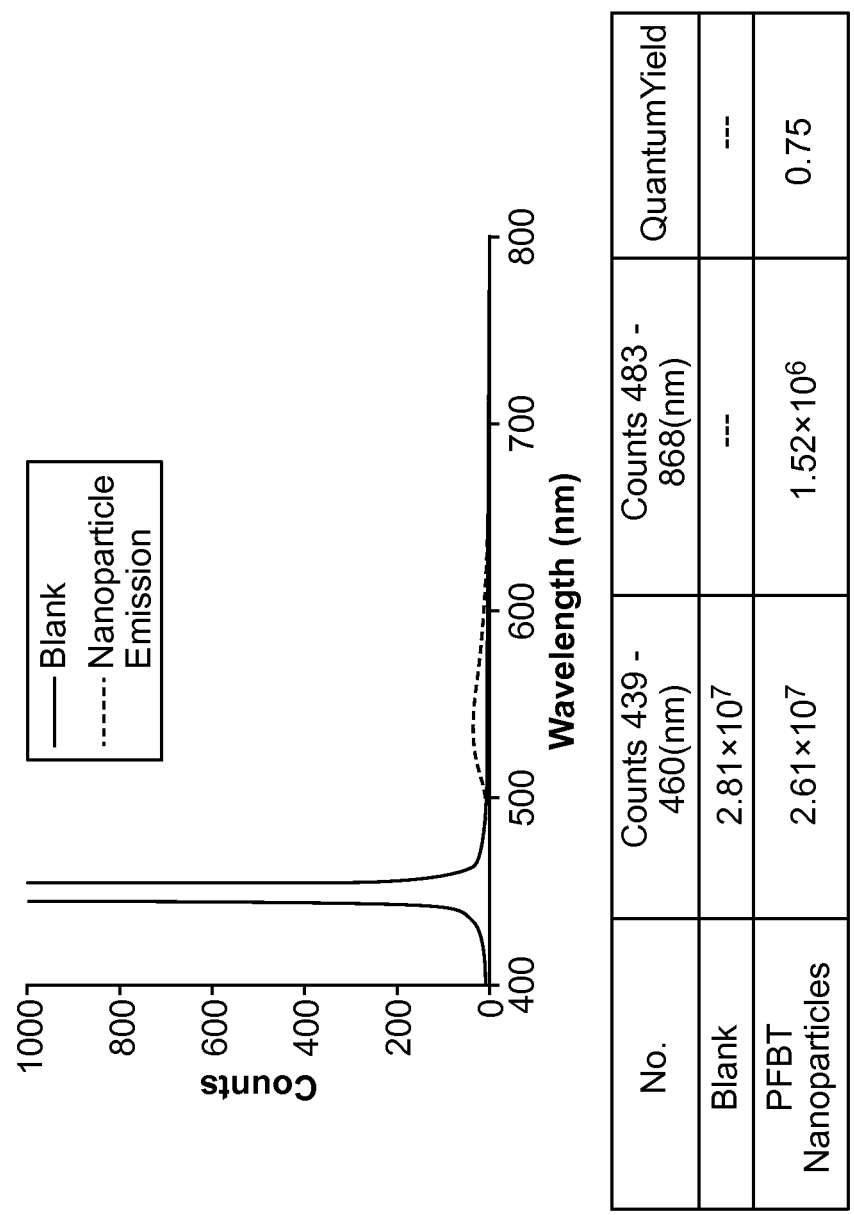
FIG. 7 demonstrates the quantum yield of polarization-sensitive nanoparticles according to an aspect of the present disclosure.
Figure 8:
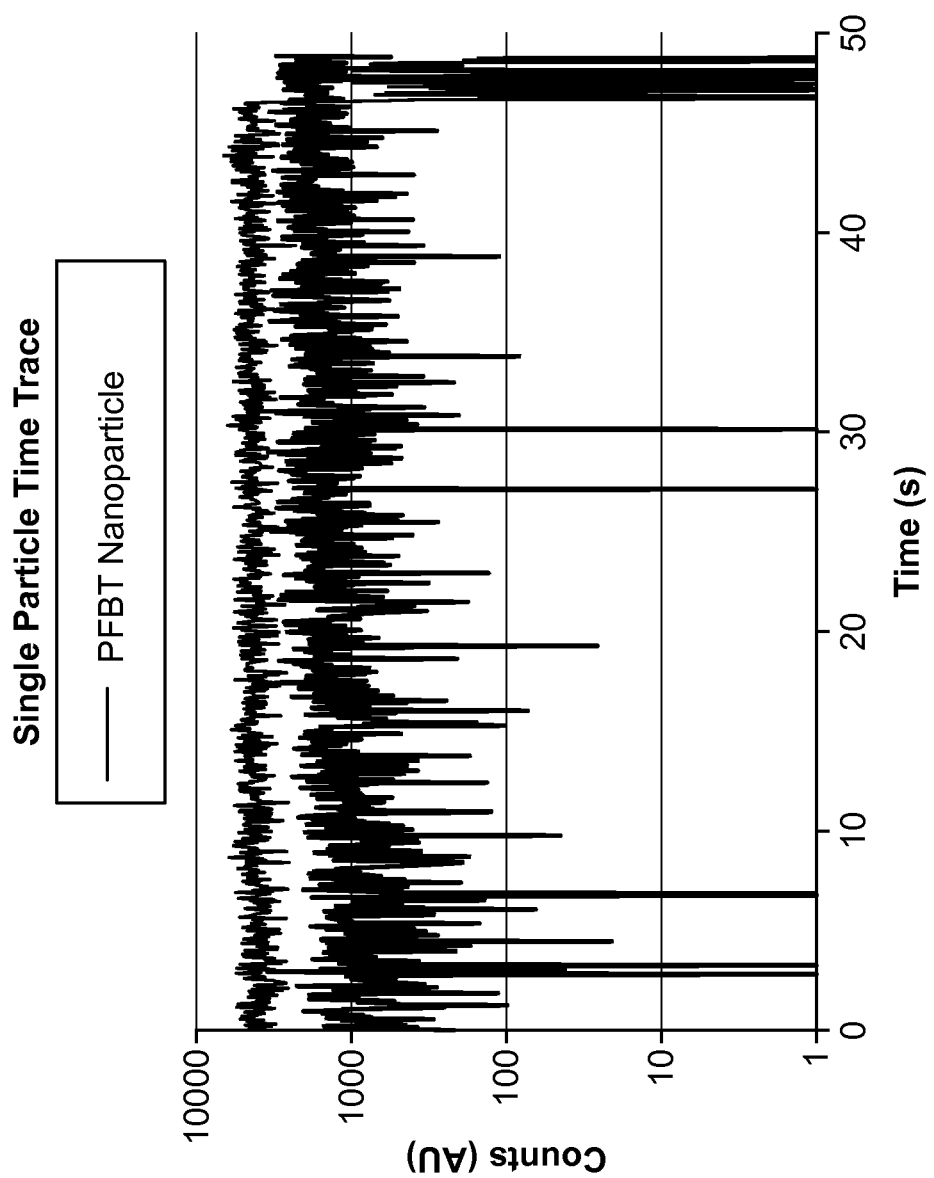
FIG. 8 is an intensity time trace of a single polymer hybrid nanoparticle and a single quantum hybrid nanoparticle according to an aspect of the present disclosure.

The mass of single polarization-sensitive nanoparticles was estimated to be 200 kDA by differential centrifugation with a 1.5 M sucrose pillow. An 8-nm diameter polymer hybrid nanoparticle with a density of 1.1 g/cm3 would weigh approximately 200 kDa. With a mass ratio of fluorescent polymer of ~1-5% and a molecular weight of 10 kDa, each polarization-sensitive nanoparticles contained around 1 PFBT chain per hybrid nanoparticle. This low mass ratio of fluorescent polymer differentiated these hybrid nanoparticles from previous hybrid nanoparticles, which generally contained at least 50% polymer by mass and, in various aspects, up to 100% (Wu, C.; Chiu, D. T. Angew. Chem. Int. Edit. 2013, 52, 3086-3109; Rong, Y.; Wu, C.; Yu, J.; Zhang, X.; Ye, F.; Zeigler, M.; Gallina, M. E.; Wu, I.-C.; Zhang, Y.; Chan, Y.-H. et al. ACS Nano. 2013, 7, 376-384). Poisson statistics predict that some of the hybrid nanoparticles contained no fluorescent polymer, but the presence of the non-fluorescing hybrid nanoparticles did not seem to affect the other hybrid nanoparticles. Although the lower mass ratio of PFBT may decrease the brightness of the polarization-sensitive nanoparticles in comparison to hybrid nanoparticles, it has other photophysical benefits. The polarization-sensitive nanoparticles were found to have a quantum yield of 0.75 (FIG. 7), which was even greater than the quantum yield of PFBT in THF solution (see Wu, C.; Chiu, D. T. Angew. Chem. Int. Edit. 2013, 52, 3086-3109; Wu, C.; Schneider, T.; Zeigler, M.; Yu, J.; Schiro, P. G.; Burnham, D. R.; McNeill, J.; Chiu, D. T. J. Am. Chem. Soc. 2010, 132, 15410-15417 which demonstrates nanoparticles that contained 80% PFBT and exhibited a quantum yield of 0.3). The high quantum yield was likely caused by the minimization of quenching by interchain aggregation (Nguyen, T.-Q.; Doan, V.; Schwartz, B. J. J. Chem. Phys. 1999, 110, 4068-4078; Jakubiak, R.; Collison, C. J.; Wan, W. C.; Rothberg, L. J. J. Phys. Chem. A. 1999, 103, 2394-2398) as well as reduced collisional quenching of photoluminescence by the solvent (Yu, J.; Hu, D.; Barbara, P. F. Science. 2000, 289, 1327-1330) due to the presence of the amphiphilic polymers protecting the hydrophobic fluorescent polymer from the aqueous environment. The polarization-sensitive nanoparticles were photostable, and brightness was nearly identical to quantum dots when excited with 488-nm light (FIGS. 8 and 9). Also, these low mass ratio polarization-sensitive nanoparticles had a high intensity dependence on the polarization of incident light.

Polymer Dot Bioconjugation

Polarization-sensitive nanoparticles were covalently bound to streptavidin in order to provide a convenient way to link hybrid nanoparticles with other biomolecules or structures of interest. 4 mL of hybrid nanoparticle solution with 0.1% PEG was mixed with 240 µL of streptavidin solution (1 mg/mL), and then 80 µL of freshly prepared EDC (5 mg/mL) was added to the solution. This was mixed for 4 hours by magnetic stirring at room temperature. After 4 hours, amine-terminated PEG was added along with an additional 80 µL of EDC in order to cap any remaining carboxylic acid groups on the surface of the hybrid nanoparticles and to reduce nonspecific binding. The reaction was allowed to continue for another 2 hours and then quenched with 80 µL of a 10 wt % BSA solution. The hybrid nanoparticles were then concentrated using a 100,000 MW cut-off centrifuge tube and purified on a size-exclusion column. The resulting streptavidin-and-PEG-functionalized hybrid nanoparticles are stable for several months if refrigerated at 4° C.

Microtubule Preparation

Microtubules were polymerized from tubulin by mixing 10 µL GTB with 9 µL of 10 mg/mL tubulin, 1 µL 10 mg/mL biotinylated tubulin, 2 µL anhydrous DMSO, and 0.5 µL GTP. The solution was placed in a 37° C. water bath and taxol was added to a final concentration of 2 µM, 20 µM, and 200 µM at 0, 10, and 20 minutes, respectively. Polymerization was continued for 60 minutes and the microtubules were shortened by pipetting the microtubule repeatedly before use. Fluorescently labeled microtubules, used as a control, were prepared by replacing the biotinylated tubulin with HiLyte 488 tubulin and polymerizing the tubulin as described herein.

Polarization Sensitivity

The polarization-sensitive nanoparticles showed a large intensity dependence on the polarization of light used for excitation. To demonstrate this, an optical setup with linearly polarized excitation was used. By using carefully positioned polarizers and λ/2 waveplates, a I∥:I⊥ excitation polarization ratio of intensities of 100:1 was achieved and measured after the objective. This polarized light selectively excited chromophores that have absorption dipoles aligned with the light; when the chromophores are confined to a specific orientation, the emitted light was polarized (Lakowicz, J. R. Principles of Fluorescence Spectroscopy; 3rd ed.; Springer, 2006). The emitted light was separated into its orthogonally polarized components, and the components were imaged onto an EMCCD camera. Information on the orientation changes of the polarization-sensitive nanoparticles could be deduced from the change in intensity of the polarized components of the emitted light. The setup used for separating the emission into its orthogonal polarizations has been described previously (Zeigler, M. B.; Allen, P. B.; Chiu, D. T. Biophys. J. 2011, 100, 2846-2851).

Figure 3:
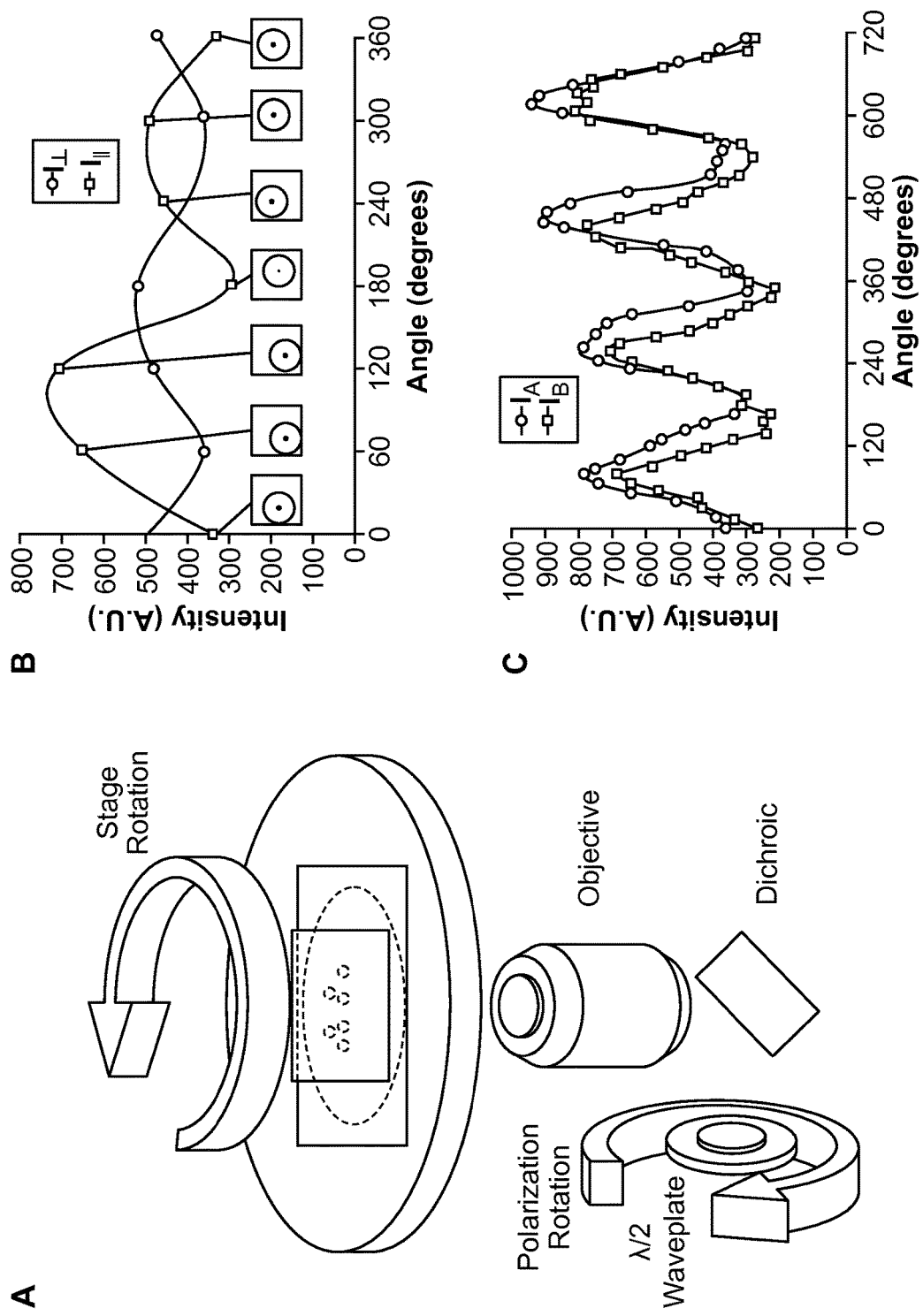
FIG. 3 shows the polarization of individual polarization-sensitive nanoparticles, including according to an aspect of the present disclosure (A) stage rotation, (B) emitted light of a single polymer nanoparticle, separated into two channels of orthogonal polarization, and (C) emitted light of a single polymer nanoparticle during rotation of the excitation polarization.

The fluorescence intensity dependence upon light polarization was monitored by two separate methods (see FIG. 3A). In part (A), a schematic showing the microscope stage and polarization-sensitive nanoparticles in a channel is shown. The polarization excitation was changed by rotation of a λ/2 plate or the stage was rotated with constant polarization. In part (B), the plot shows the emitted light of a single polymer hybrid nanoparticle, separated into two channels of orthogonal polarization. The orientation of the polymer hybrid nanoparticle was changed with respect to excitation polarization by rotating the stage while the excitation polarization was held constant. The emission shows a strong dependence upon the orientation of the single polymer hybrid nanoparticle. Inset are images taken of a single hybrid nanoparticle upon stage rotation captured by the I∥ channel. (C) The plot shows the emitted light of a single polymer hybrid nanoparticle as the excitation polarization was rotated. The correlated intensity change in orthogonally polarized emission channels, labeled IA and IB, was what would be expected from a single emitting chromophore. In both methods, polarization-sensitive nanoparticles were adsorbed to the surface of a cleaned, APTES-coated glass channel; then the channel was filled with Milli-Q water. In the first method, the excitation polarization remained fixed while the polymer hybrid nanoparticle sample was rotated manually using a rotation stage. The resulting anti-correlated intensity maxima and minima for the orthogonally polarized emitted light are shown in FIG. 3B. The intensity of emission measured in I∥ and I⊥ channels as the stage rotated was not always anti-correlated; the relationship of the intensities of the two channels depended on the orientation at which the polymer hybrid nanoparticle adsorbed to the coverslip. The orientation of the emission dipole of each polymer hybrid nanoparticle was random, so the curves for I∥ and I⊥ could be correlated as in FIG. 3C, anti-correlated, or in between correlated and anti-correlated depending on the orientation of the dipole moment with respect to the coverslip. Although the maxima and minima were present, practical issues resulting from manual repositioning of the rotation stage somewhat distorted the curves. In the second method, a λ/2 waveplate placed in a rotating mount in the excitation path was moved while the sample remained stationary. The intensity of emitted light from a single polymer hybrid nanoparticle for I∥ and I⊥ is shown in FIG. 3C. The emission from the polymer hybrid nanoparticle resembled what would be observed for a single, stationary fluorophore.

The mean molecular mass of the PFBT polymer used in the hybrid nanoparticles was 10 kDa, which corresponded to an average of 20 chromophores per polymer chain. Each fluorescent monomer was approximately 1.5 nm in length, so in order for the polymer chain to fit inside a 7-nm-diameter hybrid nanoparticle, there must be kinks in the chain. These kinks created sections of polymer chain that were local energy minima and were preferential for photon emission (Lee, J.-I.; Zyung, T.; Miller, R. D.; Kim, Y. H.; Jeoung, S. C.; Kim, D. J. Mater. Chem. 2000, 10, 1547-1550). Intrachain transfer of excitation energy to these regions allowed these polymer chains to behave similarly to a single fluorophore (Huser, T.; Yan, M.; Rothberg, L. J. Proc. Natl. Acad. Sci. USA. 2000, 97, 11187-11191). Schwartz et. al. have also shown that polarization can spontaneously increase when the excitation energy is trapped at these local minima, (Schwartz, B. J.; Nguyen, T.-Q.; Wu, J.; Tolbert, S. H. Synth. Met. 2001, 116, 35-40) which will favor polarized light emission from the polarization-sensitive nanoparticles.

Figure 4:
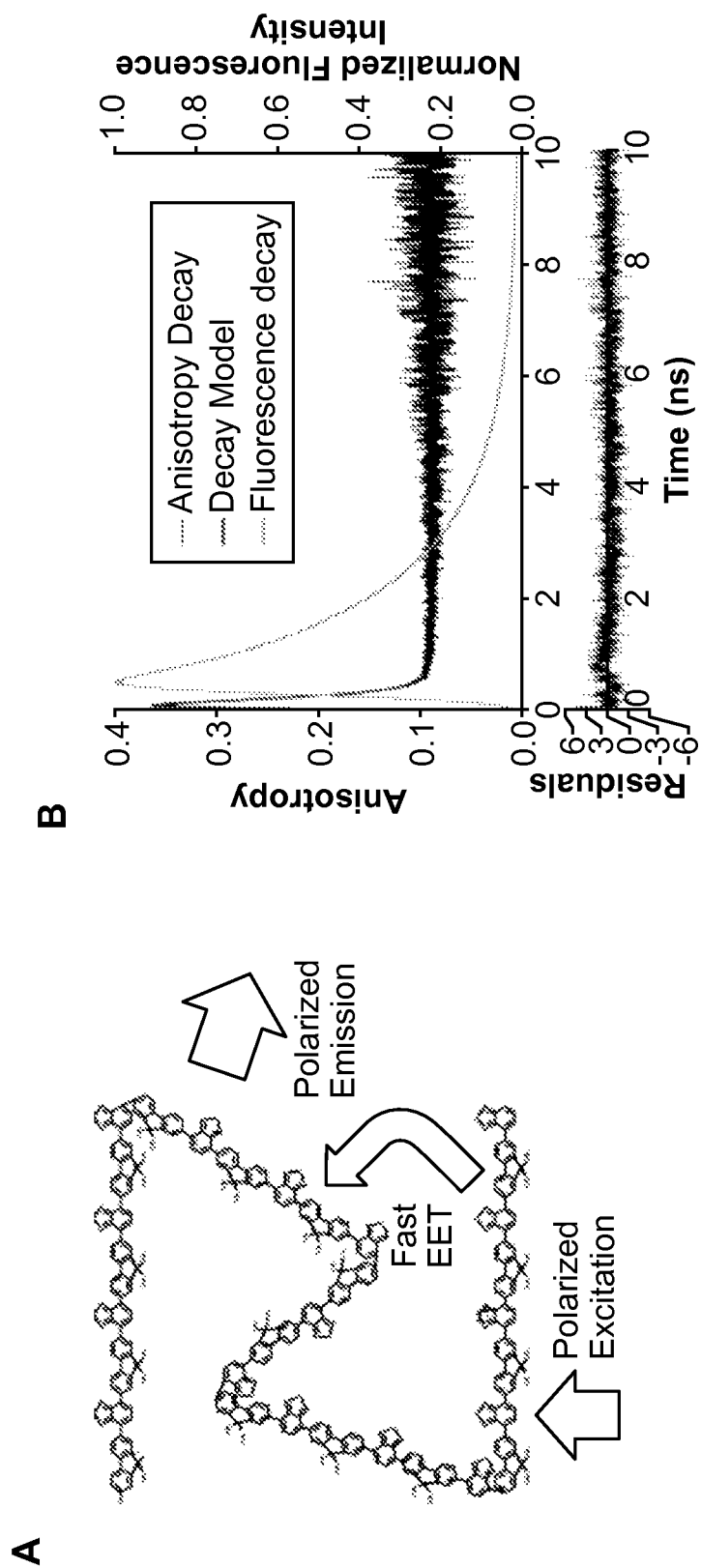
FIG. 4 shows the polarization sensitivity of a polymer hybrid nanoparticle according to an aspect of the present disclosure, including (A) intramolecular exiton transfer, (B) time-resolved fluorescence anisotropy decay overlaid with fluorescence lifetime decay of the polymer nanoparticles.

FIG. 4A is a cartoon depicting EET within the polymer hybrid nanoparticle. The PFBT polymer absorbed photons aligned with its absorption dipole and the absorbed energy was quickly transferred to the lowest energy point on the chain. The chromophore that ultimately emitted a photon may or may not have had its dipole moment aligned with the absorption dipole. This means that for individual fluorescent hybrid nanoparticles, the absorption and emission of the PFBT polymer can give information on changes in hybrid nanoparticle orientation. However, due to energy transfer, the excitation and emission polarizations are randomly oriented with respect to each other. FIG. 4B is an overlay of the time-resolved anisotropy decay and the fluorescence lifetime decay of polarization-sensitive nanoparticles in bulk aqueous solution. The high initial anisotropy of 0.36 can be due to emission from the initially excited chromophore, which was aligned with the polarized light and would be expected to be highly anisotropic. The subsequent decrease in bulk anisotropy would be caused by excitation energy transfer to a chromophore with a different emission dipole moment and little relation to the excitation polarization. Instead of decreasing to a perfectly isotropic value of 0, the fluorescence anisotropy decays to a final value of ~0.1. There are several possible explanations for this residual anisotropy: (1) this is evidence that the fluorescent polymer may maintain some preferential orientation within the polymer hybrid nanoparticle, or (2) that chemical defects in the polymer chain may prevent transfer of a portion of the energy, or (3) a percentage of the light are absorbed by the polymer's local energy minima so little further energy transfer occurs. Integration under the anisotropic decay curve revealed that 94% of photons were emitted after the lifetime of the anisotropic decay; presumably, a large majority of photons were emitted after excited energy transfer. Based on a hydrodynamic diameter of 12.1 nm, the Perrin equation was used to estimate that the rotational correlation time of the polarization-sensitive nanoparticles was 200 ns. The anisotropic decay lifetime of the polarization-sensitive nanoparticles measured in bulk aqueous solution was 170 ps, three orders of magnitude faster than the rotational correlation time and consistent with the timescale of energy transfer along the polymer backbone.

Microtubule Gliding Assay

All glass coverslips were cleaned by sonication for 30 minutes in a 2% Micro-90 solution, followed by thorough rinsing in Milli-Q water and sonication for 30 minutes in Milli-Q water. The glass was then boiled in a 3:2:1 solution of Milli-Q:$NH_4OH$:$H_2O_2$ for 60 minutes, followed by thorough rinsing with Milli-Q water before use. A channel with the approximate dimensions of 2.5 cm×1 cm×1 μm, was created using a clean glass slide attached to a 1" coverslip using double-sided sticky tape. Gliding microtubules with attached hybrid nanoparticles were visualized using a slightly modified technique previously described by Wang et al.[25] A series of five solutions, 10 μL each, were introduced to the channel and allowed to sit for 5 minutes after their introduction. Solution 1 contained GTB with 0.5 mg/mL casein. Solution 2 contained GTB with 0.2 mg/mL casein, 0.3 mM MgATP, and kinesin. Solution 3 contained GTB with 0.5 mg/mL casein, 0.3 mM MgATP, 10 μM Taxol, and 0.05 μL of the microtubule solution. Solution 4 contained GTB with 0.5 mg/mL casein, 0.3 mM MgATP, 10 μM Taxol, and 50 pM functionalized hybrid nanoparticles. Solution 5 contained GTB with 0.5 mg/mL casein, 1.5 mM MgATP, 10 μM Taxol, and an oxygen scavenging system (50 μg/mL glucose oxidase, 4 μg/mL catalase, 1% glucose, and 0.1% β-mercaptoethanol). The final solution was introduced three times to flush out the free polarization-sensitive nanoparticles.

Optical Setup

Polarized wide field illumination was accomplished using best form spherical singlet lenses, 488 nm λ/2 waveplates, and polarizers (Thorlabs, Newton, N.J.). Through careful placement of polarization optics, an $I_\parallel$:$I_\perp$ ratio of 100:1 was achieved. The 488-nm dichroic mirror was chosen for its insensitivity to polarization for reflection and transmission. Fluorescence excitation came from a Sapphire 488-nm laser (Coherent, Santa Clara, Calif.). Excitation light was filtered out using a 500-nm longpass filter. Imaging was carried out using a TE-2000 microscope (Nikon, Melville, N.Y.) and a 100×1.3 numerical aperture objective. A home-built setup described previously (Zeigler et al)[19] was used to separate the orthogonally polarized fluorescence components, and the resulting pair of images were captured on two halves of the same Cascade 512b EMCCD camera (Photometrics, Tucson, Ariz.).

Observation of Individual Surface Bound Polarization-Sensitive Nanoparticles.

Individual polarization-sensitive nanoparticles were observed by applying very dilute (1 pM) solutions of polarization-sensitive nanoparticles to (3-aminopropyl)triethoxysilane treated number 1 glass coverslips (Bellco, Vineland N.J.). The coverslips were photoetched to assist in positioning the coverslip under bright-field illumination. After five minutes, the coverslips were rinsed with Milli-Q water, dried, and made in a channel as described previously. Polarization-sensitive nanoparticles polarization sensitivity was demonstrated by filling the channel with water and inserting the channel into a rotating stage mounted on the microscope. The polarization-sensitive nanoparticles were illuminated and stage was rotated manually to visualize the selectively polarized emission of individual polarization-sensitive nanoparticles.

Characterization of Polarization-Sensitive Nanoparticles

All fluorescence spectra were taken in 20 mM HEPES buffer, pH 7.4, supplemented with 0.1% PEG. Quantum yield measurements were taken using a Hamamatsu absolute PL quantum yield measurement system (Hamamatsu, Shizuoka, Japan), excited at 450 nm with a xenon lamp. Fluorescence lifetime and time-resolved fluorescence anisotropy measurements were taken using a Pico Quant Fluo time 100 system and a 470 nm picosecond laser as per manufacturer's recommendation and analyzed using commercial Fluo Fit software (Picoquant GmbH, Berlin, Germany). Hybrid nanoparticle size and zeta potential were characterized using a Zetasizer Nano ZS (Malvern, Philadelphia, Pa.). Fluorescence spectra were taken using the Fluorolog-3 fluorospectrometer (HORIBA, JobinYvon, N.J.). Fluorescence spectra were taken in 20 mM HEPES buffer, pH 7.4, with 0.1% PEG.

Figure 5A:
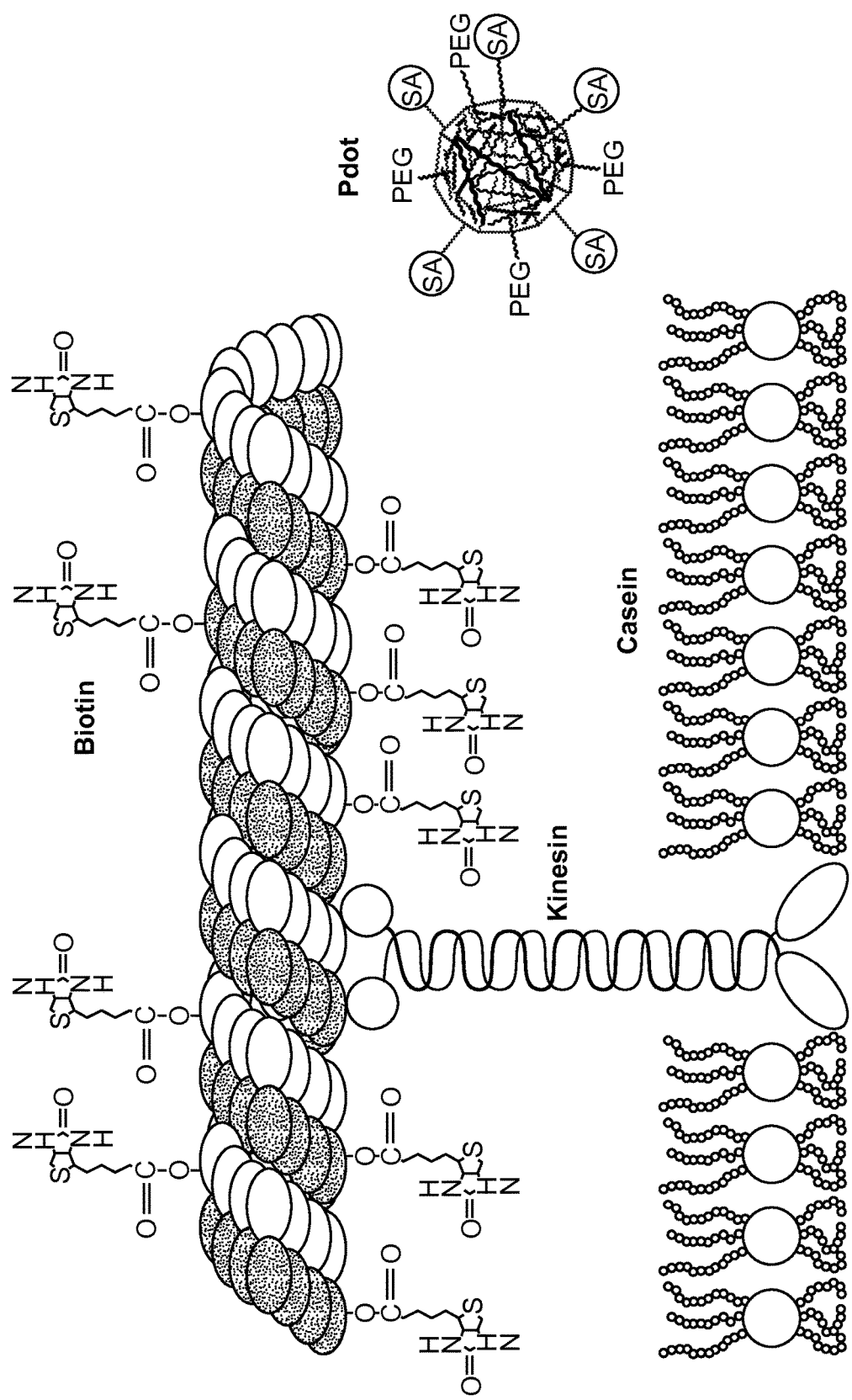
FIG. 5 shows the detection of microtubule rotation using polarization-sensitive polymer nanoparticles according to an aspect of the present disclosure, including (A) a schematic showing a gliding microtubule moved by kinesin bound to a glass substrate, (B) measured microtubule periods of rotation when microtubules are transported by two different forms of kinesin, and (C) the track of a single microtubule.

Semiconducting Polarization-Sensitive Nanoparticles as Detectors of Microtubule Orientation The small size, optical stability, chemical flexibility, and polarization sensitivity of the polarization-sensitive nanoparticles makes them good candidates for probes to detect orientation changes in proteins. Eukaryotic microtubules inside cells usually each contain 13 protofilaments comprised of repeating units of α and β tubulin; microtubules polymerized in vitro have been shown to consist of varying numbers of protofilaments. Variation away from 13 protofilaments per microtubule can create a periodic twist in the cylinder of the microtubule (Chrétien, D.; Wade, R. R. Biol. Cell. 1991, 71, 161-174; Sanghamitra, R.; Meyerhöfer, E.; Milligan, R. A.; Howard, J. J. Cell Biol. 1993, 121, 1083-1093; Wang, G.; Sun, W.; Luo, Y.; Fang, N. J. Am. Chem. Soc. 2010, 132, 16417-16422). The motor protein kinesin precesses along the protofilaments axis in the microtubule, following along with any potential periodic twist in the microtubule axis. In a microtubule gliding assay, kinesin was passively adsorbed onto a glass surface to drive microtubules labeled with polarization-sensitive nanoparticles through a channel. As the microtubules were directed by kinesin, the periodicity of the microtubule twist could be visualized using fluorescence microscopy (FIG. 5A).

The heavy chain of kinesin is approximately 70 nm long and the gliding assay was not inhibited by the presence of the 12-nm-diameter polarization-sensitive nanoparticles.

Figure 5C:
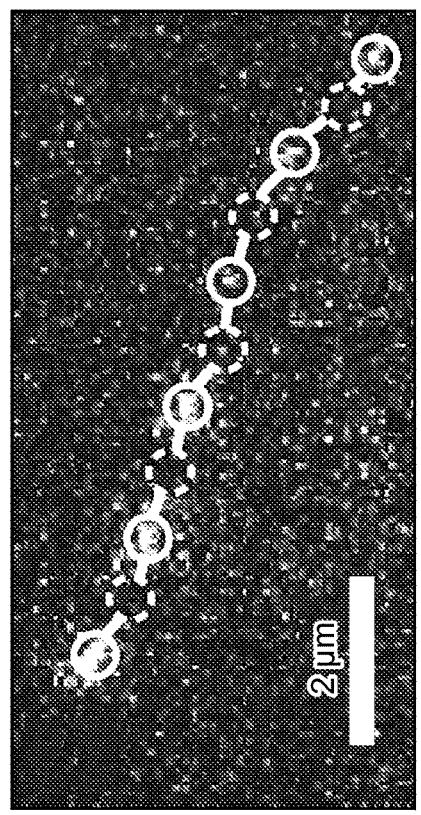
Figure 5B:
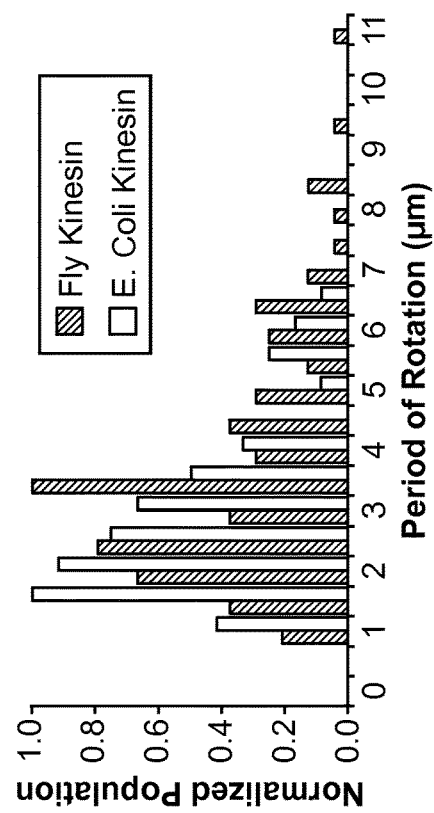

The periodicity of the microtubule twists was measured in this gliding assay using two different kinesin proteins: one fruit fly kinesin with a precession rate of 0.8 µm/s and E. coli kinesin with a precession rate of 1.2 µm/s. We measured the rate of precession of polymer-hybrid nanoparticle-labeled microtubules and microtubules containing fluorescent tubulin protein. The rates were the same for the fluorescently labeled and polymer-hybrid nanoparticle-labeled microtubules. The polarization-sensitive nanoparticles did not appear to inhibit kinesin function. The histogram of the measured microtubule twist lengths are shown in FIG. 5B, and the measured distributions in twist length remained consistent between the slower fruit fly and faster E. coli kinesin proteins. In detail, part (A) depicts a scheme showing a gliding microtubule moved by kinesin bound to a glass substrate. The polarization-sensitive nanoparticles link to biotinylated tubulin within the microtubule. Part (B) shows the measured microtubule periods of rotation when the microtubules are transported by two different forms of kinesin. There were 62 microtubules measured using E. coli kinesin and 131 measured using Drosophila kinesin along with 64 and 148 nonrotating microtubules, respectively. Part (C) depicts the track of a single microtubule with a single bound polymer hybrid nanoparticle (open circles) show local intensity maxima while dashed circles indicate the location of local intensity minima in one of the observed channels. The twists were determined by the distance between local intensity maxima of polymer hybrid nanoparticle emission, and were not counted unless at least two consecutive periods of the same length were recorded between three local intensity maxima. Also, local intensity maxima and minima had to vary by at least 50%, representing a change in hybrid nanoparticle absorption/emission dipole orientation of approximately 0.75 radians over the course of the rotation. The observed numbers of rotating microtubules bound to fruit fly and E. coli kinesins were 131 and 62, respectively. Along with polarization-sensitive nanoparticles that periodically showed bright and dark emission, a significant number of hybrid nanoparticles showed continuous emission while bound to precessing microtubules. This could be due to the observation of microtubules made of 13 protofilaments which did not have a twist or the absorption/emission dipole of the hybrid nanoparticle aligned with the microtubule. The latter case was considered unlikely, as in some cases several polarization-sensitive nanoparticles labeled a single microtubule and each microtubule with multiple labels either exhibited periodic or constant emission from all bound hybrid nanoparticles. 171 nonrotating microtubules bound to the fruit fly kinesin and 69 nonrotating microtubules bound to E. coli kinesin were observed. FIG. 5C is a trace of a microtubule labeled with a single polymer hybrid nanoparticle, showing alternating bright and dark spots as the microtubule rotates.

The microtubules were polymerized with 10% biotinylated tubulin, which allowed strong binding between streptavidin-functionalized polarization-sensitive nanoparticles and the microtubules. Because of the high density of biotinylated tubulin and the size of the polarization-sensitive nanoparticles and tubulin units, it was likely that each polymer hybrid nanoparticle was bound to the microtubule by more than one biotin/streptavidin linkage. Virtually no fast, sporadic intensity fluctuations were visible that would be evidence for single biotin/streptavidin linkages or "the propeller effect" of polarization-sensitive nanoparticles with flexible attachments to microtubules.

FIG. 8 is an intensity time trace of a single polymer hybrid nanoparticle and a single quantum hybrid nanoparticle. This PFBT hybrid nanoparticle was bound to a stationary microtubule and shows little blinking and a single photobleaching event. The hybrid nanoparticles used did show intermittent blinking when passively adsorbed to a glass coverslip, but this blinking was almost entirely extinguished when bioconjugated hybrid nanoparticles were bound to microtubules. Although the brightness of this PFBT hybrid nanoparticle was higher than the quantum hybrid nanoparticle, single-particle brightness measurements show that they have comparable average brightness.

FIG. 9 shows the single particle brightness histogram comparing polarization-sensitive nanoparticles and Qhybrid nanoparticle 525. Mean brightness was 3035±424 (n=178) and 3020±492 (n=179) for polarization-sensitive nanoparticles and 525 nm emission quantum hybrid nanoparticles, respectively.

What is claimed is:

1. A polarization-sensitive nanoparticle comprising:
   a semiconducting chromophoric polymer; and
   a matrix, wherein the matrix comprises:
      a first non-semiconducting matrix polymer; and
      a second non-semiconducting matrix polymer;
   wherein:
      the nanoparticle comprises a blend of the first non-semiconducting matrix polymer, the second non-semiconducting matrix polymer, and the semiconducting chromophoric polymer;
      the polarization-sensitive nanoparticle has at least one critical dimension of 1 nm to 1000 nm; and
      the percent of semiconducting chromophoric polymer mass is about 1% to 5% of the total mass of the nanoparticle.

2. The polarization-sensitive nanoparticle of claim 1, wherein the semiconducting chromophoric polymer is luminescent.

3. The polarization-sensitive nanoparticle of claim 1, wherein the semiconducting chromophoric polymer is hydrophobic.

4. The polarization-sensitive nanoparticle of claim 1, wherein the first non-semiconducting matrix polymer is an amphiphilic polymer.

5. The polarization-sensitive nanoparticle of claim 1, wherein the first non-semiconducting matrix polymer comprises a first functional group capable of conjugation.

6. The polarization-sensitive nanoparticle of claim 1, wherein the second non-semiconducting matrix polymer is an amphiphilic polymer.

7. The polarization-sensitive nanoparticle of claim 5, wherein the second non-semiconducting matrix polymer further comprises a second functional group capable of conjugation.

8. The polarization-sensitive nanoparticle of claim 1, wherein the first non-semiconducting matrix polymer and the second non-semiconducting matrix polymer are the same.

9. The polarization-sensitive nanoparticle of claim 1, wherein the polarization-sensitive nanoparticle is fluorescent.

10. The polarization-sensitive nanoparticle of claim 1, wherein the polarization-sensitive nanoparticle is conjugated to a binding moiety and wherein the binding moiety is configured to bind to a target.

11. The polarization-sensitive nanoparticle of claim 10, wherein the target is a biomolecule.

12. The polarization-sensitive nanoparticle of claim 10, wherein the target is a biomarker.

13. The polarization-sensitive nanoparticle of claim 7, wherein the first functional group, the second functional group, or a combination thereof are suitable for bioconjugation.

14. A method of analyzing a target, the method comprising:
   binding a polarization-sensitive nanoparticle to the target;
   illuminating the nanoparticle with electromagnetic radiation sufficient to produce a florescence signal; and
   detecting the fluorescence signal;
   wherein the nanoparticle comprises:
      a semiconducting chromophoric polymer; and
      a matrix, wherein the matrix comprises:
         a first non-semiconducting matrix polymer; and
         a second non-semiconducting matrix polymer;
      wherein the nanoparticle has at least one critical dimension of 1 nm to 1000 nm; and
      the percent of semiconducting chromophoric polymer mass is about 1% to 5% of the total mass of the nanoparticle.

15. The method of claim 14, wherein the electromagnetic radiation is polarized.

16. The method of claim 14, further comprising detecting a change in the fluorescence signal while analyzing the target.

17. The method of claim 14, further comprising detecting the orientation of the target from the change in the fluorescence signal.

18. The method of claim 14, further comprising imaging a target.

19. The method of claim 14, wherein the target is a biomolecule.

20. The method of claim 14, wherein the target is a biomarker.

21. The polarization-sensitive nanoparticle of claim 1, wherein the polarization-sensitive nanoparticle has a full width at half maximum of the fluorescence emission peak of less than 60 nm.

22. The polarization-sensitive nanoparticle of claim 1, wherein the semiconducting chromophoric polymer is immobilized within the matrix.

23. The polarization-sensitive nanoparticle of claim 1, wherein the nanoparticle is conjugated to an antibody, a protein, a nucleic acid, a streptavidin, a peptide, an aptamer, an enzyme, a carbohydrate, a deoxyribonucleic acid, a ribonucleic acid, or a lipid.

24. The polarization-sensitive nanoparticle of claim 14, wherein the semiconducting chromophoric polymer is immobilized within the matrix.

* * * * *